United States Patent
Sircar et al.

(10) Patent No.: US 7,342,012 B2
(45) Date of Patent: Mar. 11, 2008

(54) INHIBITORS OF $\alpha_L\beta_2$ MEDIATED CELL ADHESION

(75) Inventors: Ila Sircar, San Diego, CA (US); Paul Furth, Bonita, CA (US); Bradley R. Teegarden, San Diego, CA (US); Marshall Morningstar, San Diego, CA (US); Nicholas Smith, San Diego, CA (US); Ronald C. Griffith, Escondido, CA (US)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 224 days.

(21) Appl. No.: 11/070,335

(22) Filed: Mar. 3, 2005

(65) Prior Publication Data

US 2005/0148602 A1    Jul. 7, 2005

Related U.S. Application Data

(62) Division of application No. 10/111,110, filed as application No. PCT/US00/29273 on Oct. 19, 2000, now Pat. No. 6,897,225.

(60) Provisional application No. 60/209,847, filed on Jun. 7, 2000, provisional application No. 60/160,629, filed on Oct. 20, 1999.

(51) Int. Cl.
*C07D 487/04* (2006.01)
*A61K 31/4985* (2006.01)

(52) U.S. Cl. .................... 514/233.2; 544/117; 544/350; 514/249

(58) Field of Classification Search ................ 544/350, 544/117; 514/249, 233.2
See application file for complete search history.

(56) References Cited

FOREIGN PATENT DOCUMENTS

| AU | A-82875/87 | 6/1988 |
|---|---|---|
| WO | WO 98/39303 A1 | 9/1998 |
| WO | WO 98/58947 A1 | 12/1998 |
| WO | WO 99 010312 A1 | 3/1999 |

OTHER PUBLICATIONS

Chalmers (TiPS vol. 17, pp. 166-172 Apr. 1996).*
Dyatkin, Tetrahedron Letters, vol. 38, No. 12, pp. 2065-2066 (1997).
Kelly et al., J. Immunol., vol. 163, No. 10, pp. 5173-5177 (1999).
Bianco et al., J. Org. Chem., vol. 65, No. 7, pp. 2179-2187 (2000).
Chalmers (TiPS vol. 17, pp. 166-172 Apr. 1996).

* cited by examiner

*Primary Examiner*—Kahsay Habte
(74) *Attorney, Agent, or Firm*—Birch, Stewart, Kolasch & Birch, LLP

(57) ABSTRACT

The present invention relates to a compound of the following formula:

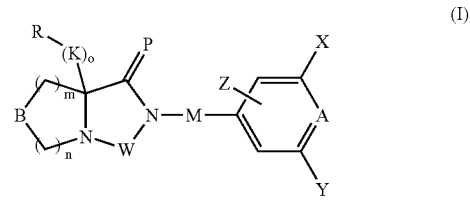

(I)

or a pharmaceutically acceptable salt thereof. Also disclosed are compositions containing the compound and methods of preparing and using the compounds. The compounds of the invention are useful in treating $\alpha_L\beta_2$ adhesion mediated conditions in a mammal.

8 Claims, No Drawings

INHIBITORS OF $\alpha_L\beta_2$ MEDIATED CELL ADHESION

This application is a Divisional of application Ser. No. 10/111,110 filed on Oct. 16, 2002 now U.S. Pat. No. 6,897,225 and for which priority is claimed under 35 U.S.C. § 120. application Ser. No. 10/111,110 is the national phase of PCT International application Ser. No. PCT/US00/29273 filed on Oct. 19, 2000 under 35 U.S.C. § 371. The entire contents of each of the above-identified applications are hereby incorporated by reference. This application also claims priority of Provisional U.S. Application Nos. 60/160,629 filed on Oct. 20, 1999 and 60/209,847 filed on Jun. 7, 2000 under 35 U.S.C. § 119.

BACKGROUND OF THE INVENTION

1. Field of the Invention

The present invention relates to small molecules that are potent inhibitors of $\alpha_L\beta_2$ mediated cell adhesion which could be useful for the treatment of inflammatory diseases.

2. Description of Related Art

The integrin family of proteins are heterodimeric receptors which are expressed on all cell types to mediate cell to cell binding and adhesion to extracellular matrix. The $\beta_2$ (CD18) integrin subfamily is comprised of 3 members, $\alpha_L\beta_2$ integrin (LFA-1, CD11a/CD18), $\alpha_M\beta_2$ integrin (Mac-1, CD11b/CD18), and gp 150 $\beta_2$ integrin ($\alpha_X\beta_2$ integrin, CD11c/CD18) that are primarily expressed on leukocytes (Sanchez-Madrid et al., J. Exp. Med., 158, 1785-1803 (1983)). $\alpha_L\beta_2$ integrin is found mostly on T and B lymphocytes, while $\alpha_M\beta_2$ integrin is present on activated neutrophils, NK cells and some myeloid cells. The $\alpha_L\beta_2$ integrin binds intracellular adhesion molecules ICAM-1, 2 and 3 found on multiple cell types such as vascular endothelial cells, dendritic cells, epithelial cells, macrophage and T lymphoblasts (Dustin et al., J. Immunology, 137, 245-254 (1986)). Recently there has been evidence presented that $\alpha_L\beta_2$ integrin binds to ICAM-4 and a novel ligand expressed in brain telencephalin. It has been shown that the I domain of the alpha chain is the major recognition site for its ligands.

$\alpha_L\beta_2$ integrin adhesion to ICAM-1 is necessary for immune responsiveness of T-lymphocytes to antigens, lymphocyte homing and circulation, and cell emigration to sites of inflammation (Springer, Ann. Rev. Physiol., 57, 827 (1995)). A dominant role of $\alpha_L\beta_2$ integrin in mediating inflammatory events is shown in several different animal models of inflammatory diseases in which antibodies to $\alpha_L\beta_2$ integrin or ICAM-1 significantly inhibit development of therapeutic end points (Rothlein et al., Kidney International, 41, 617 (1992); Iigo et al., J. Immunology, 147, 4167 (1991); Bennet et al., J. Pharmacol. and Exp. Therapeutics, 280, 988 (1997)).

Also, $\beta_2$ integrin subfamily are thought to play a critical role in several types of inflammatory disease processes by interacting with ICAMs. Support for the importance of $\beta_2$ integrin in mediating inflammatory responses has been demonstrated by the evidence that transendothelial migration in vitro is markedly inhibited by monoclonal antibodies against $\beta_2$ integrin or ICAM-1 (Smith, Can. J. Physiol. Pharmacol., 71, 76 (1993). Furthermore, blockade of $\alpha_L\beta_2$ integrin has been shown to inhibit neutrophil influx in almost every system, including skin, peritoneum, synovium, lung, kidney, and heart. As one of the primary ligands for the $\beta_2$ integrin, it would also be expected that blockade of ICAM-1 would inhibit the inflammatory response (Albelda et al., The FASEB Journal, 8, 504 (1994)).

Moreover, it has been shown that antibodies against $\alpha_L\beta_2$ integrin suppress rejection after transplantation. WO 94/04188 discloses the use of monoclonal antibodies directed against $\alpha_L\beta_2$ integrin for all transplantation's, including graft vs. host or host vs. graft diseases.

SUMMARY OF THE INVENTION

The present invention relates to a compound of the formula (I):

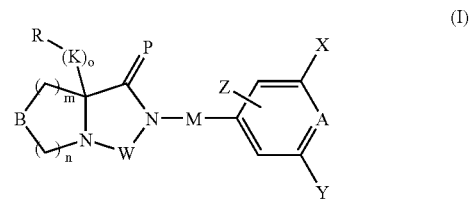

wherein

A is $=C(Z^1)-$, or $=N-$;

B is $-C(R^1)(R^2)-$, $-CH=CH-$, $-S-$, $-SO-$, $-SO_2-$, $-O-$, $-N(R^3)-$, $-N(COR^{41})-$, $-N(CSR^{41})-$, $-N(SO_2R^5)-$, $-N(R^3)CO-$, $-N(COR^{41})CO-$, $-N(CSR^{41})CO-$, or $-N(SO_2R^5)CO-$;

K is $-CH_2-$, $-CH(OH)-$, $-C(=O)-$, or $-CF_2-$;

M is a single bond, $-(CH_2)_p-$, $-C(=O)-$ or $-NH-$;

W is one of the following groups:

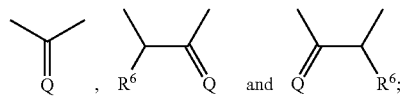

X and Y are independently H, halogen, $NO_2$, CN, $C_{1-6}$ alkylthio, $NR^3R^6$, $C_{1-6}$ alkyl optionally substituted with halogen, $C_{1-6}$ alkoxy, $COR^{42}$, aryl which may be substituted, or heteroaryl which may be substituted;

Z and $Z^1$ are independently H, OH, halogen, $NO_2$, $CF_3$, $NR^3R^6$, $NHCOR^{41}$, $C_{1-6}$ alkoxy optionally substituted with carboxyl, $C_{1-6}$ alkoxycarbonyl, or phenyl, or $COR^{42}$;

P and Q are independently O or S;

R is aryl or heteroaryl, and each may be substituted with a group selected from:
 1) halogen,
 2) OH,
 3) CN,
 4) $C_{1-6}$ alkyl optionally substituted with a group selected from a) halogen b) $OR^6$, c) $COR^{41}$, d) aryl which may be substituted, or e) $NR^3R^6$,
 5) $C_{1-6}$ alkoxy optionally substituted with a group selected from a) halogen b) $NR^3R^6$, c) aryl which may be substituted, d) heteroaryl which may be substituted, and e) non-aromatic heterocyclic group,
 6) $NO_2$,
 7) $NR^3R^6$,
 8) $NHCOR^{41}$,
 9) $NHSO_2R^5$,

10) COR$^{42}$,

11) C(=NH)NH$_2$,

12) CONHOH,

13) C$_{1-6}$ alkylthio which may be substituted with halogen,

14) C$_{1-6}$ alkylsulfinyl which may be substituted with halogen,

15) C$_{1-6}$ alkylsulfonyl which may be substituted with halogen,

16) C$_{1-3}$ alkylenedioxy optionally substituted with a) C$_{1-6}$ alkyl, b) halogen, c) aryl which may be substituted, or d) heteroaryl which may be substituted, 17) —C(=O)— (natural α-amino acid residue), wherein said natural α-amino acid residue may be esterified with C$_{1-6}$ alkyl group, 18) aryl which may be substituted, and 19) heteroaryl which may be substituted;

R$^1$ and R$^2$ are independently H, halogen, OR$^3$, OCOR$^5$, SO$_2$R$^5$, NR$^3$R$^6$, NR$^6$COR$^{41}$, NR$^6$CSR$^{41}$, NR$^6$SO$_2$R$^5$, OCONR$^3$R$^3$, N$_3$, C$_{1-6}$ alkyl which may be substituted, CN, COR$^{42}$, aryl which may be substituted, or heteroaryl which may be substituted;

or R$^1$ and R$^2$ combine with each other at the terminal thereof to form oxo, C$_{2-3}$ alkylenedioxy, or methylene substituted with carboxyl, C$_{1-6}$ alkoxycarbonyl, or CONR$^a$R$^b$;

R$^a$ and R$^b$ combine with each other at the terminals thereof to form a 3-7 membered ring together with the nitrogen atom to which they are attached, where said 3-7 membered ring may include additional heteroatoms, such as oxygen, nitrogen and sulfur and may be substituted with C$_{1-6}$ alkyl, oxo, hydroxy, C$_{1-6}$ alkoxy or NR$^6$R$^6$;

R$^3$ is H, C$_{1-6}$ alkyl which may be substituted, C$_{3-6}$ cycloalkyl, aryl which may be substituted, heteroaryl which may be substituted, or non-aromatic heterocyclic group;

R$^{41}$ is C$_{1-6}$ alkyl which may be substituted, C$_{1-6}$ alkoxy which may be substituted, aryl which may be substituted, heteroaryl which may be substituted, non-aromatic heterocyclic group which may be substituted, C$_{3-6}$ cycloalkyl, or NR$^3$R$^6$;

R$^{42}$ is H, OH, C$_{1-6}$ alkyl which may be substituted, C$_{1-6}$ alkoxy which may be substituted, aryl which may be substituted, NR$^3$R$^6$, or non-aromatic heterocyclic group which may be substituted;

R$^5$ is C$_{1-6}$ alkyl which may be substituted, or aryl which may be substituted;

R$^6$ is H or C$_{1-6}$ alkyl which may be substituted;

m is 0, 1, 2 or 3; n is 0, 1 or 2; o is 1 or 2; p is 1 or 2; or a pharmaceutically acceptable salt thereof.

DETAILED DESCRIPTION OF THE INVENTION

The desired compound of the present invention may exist in the form of optical isomers based on asymmetric atoms thereof, and the present invention also includes these optical isomers and mixtures thereof.

In an embodiment of the present invention, the steric configuration of a bond need not be fixed. The compound of the present invention may be a compound with a sole configuration or a mixture with several different configurations.

In the above formula (I), "aryl" might be a mono-, bi- or tri-cyclic aryl group such as a phenyl group, a naphthyl group, an anthryl group, a fluorenyl group.

In the above formula (I), "heteroaryl" may be a heteroatom-containing mono-, bi- or tri-cyclic aryl group. Examples of heteroaryl group may be a pyridyl group, a pyrimidinyl group, a pyridazinyl group, a pyrazinyl group, a quinolyl group, an isoquinolyl group, a quinazolinyl group, a phthalazinyl group, an imidazolyl group, an isoxazolyl group, a pyrazolyl group, an oxazolyl group, a thiazolyl group, an indolinyl group, a benzoxazolyl group, a benzothiazolyl group, a benzimidazolyl group, a benzofuryl group, a furyl group, a thienyl group, a pyrrolyl group, an oxadiazolyl group, a thiadiazolyl group, a triazolyl group, a tetrazolyl group, an oxazolyl group, an indazolyl group, an isoindolyl group, a purinyl group, a quinoxalyl group, a benzothienyl group, a benzofurazanyl group, a benzothiadiazolyl group, an imidazothiazolyl group, a dibenzofuranyl group, and an isothiazolyl group.

In the above formula (I), "non-aromatic heterocyclic group" may be a heteroatom-containing mono-, bi- or tri-cyclic non-aromatic group. Examples of non-aromatic heterocyclic group may be a pyrrolidinyl group, a piperidyl group, an imidazolidinyl group, a pyrazolidinyl group, a piperazinyl group, a quinuclidinyl group, a morpholinyl group, a homopiperidyl group, and a thiomorpholinyl group which may be oxidized.

In a preferred embodiment of the compound (I), aryl in the definition of X, Y, R$^1$, R$^2$, R$^3$, R$^{41}$, R$^{42}$ and R$^5$ is a group independently selected from phenyl and naphthyl, and heteroaryl in the definition of X, Y, R$^1$, R$^2$ and R$^{41}$ is a group independently selected from furyl, thienyl, pyrrolyl, oxazolyl, isoxazolyl, pyridyl, thiazolyl and tetrazolyl, wherein said phenyl, naphthyl, furyl, thienyl, pyrrolyl, oxazolyl, isoxazolyl, pyridyl, thiazolyl and tetrazolyl group may be substituted with 1-4 groups selected from halogen, carboxyl, C$_{1-7}$ alkanoyl, C$_{1-6}$ alkyl, C$_{1-6}$ alkoxy-carbonyl, and NR$^6$R$^6$. Non-aromatic heterocyclic group in the definition of R$^3$, R$^{41}$ and R$^{42}$ is independently a group of the formula —NR$^a$R$^b$, wherein R$^a$ and R$^b$ are the same as defined above. Examples of said —NR$^a$R$^b$ group may be morpholinyl, pyrrolidinyl, piperazinyl, and piperidyl.

In another preferred embodiment of the compound (I), aryl in the definition of R is independently selected from phenyl and naphthyl. Heteroaryl in the definition of R is independently selected from pyridyl, benzofuryl, thiazolyl, furyl, thienyl, pyrrolyl, dihydroxazolyl, isoxazolyl, benzothienyl and tetrazolyl. Non-aromatic heterocyclic group in the definition of R is independently selected from morpholinyl, piperidinyl and pyrrolidinyl.

In a more preferred embodiment of the present invention, X and Y are independently selected from:

1) halogen,

2) NO$_2$,

3) C$_{1-6}$ alkyl optionally substituted with halogen,

4) C$_{1-6}$ alkoxy group,

5) C$_{1-7}$ alkanoyl group,

6) CN, 7) carboxyl,

8) C$_{1-6}$ alkylthio,

9) NR$^3$R$^6$, 10) phenyl optionally substituted with a) C$_{1-6}$ alkyl optionally substituted with halogen, b) C$_{1-6}$ alkoxy optionally substituted with halogen, or c) CN, 11) isoxazolyl optionally substituted with C$_{1-6}$ alkyl, 12) pyrrolyl optionally substituted with C$_{1-6}$ alkoxycarbonyl or formyl, 13) pyridyl;

R is phenyl, naphthyl, pyridyl, benzofuryl or thiazolyl, and said phenyl, naphthyl, pyridyl, benzofuryl and thiazolyl may be substituted with a group selected from:
1) halogen,
2) OH,
3) CN,
4) $C_{1-6}$ alkyl optionally substituted with a group selected from a) halogen, b) $OR^6$, or c) $COR^{41}$,
5) $C_{1-6}$ alkoxy optionally substituted with a group selected from a) halogen, b) $NR^3R^6$, c) pyridyl, or d) piperidinyl,
6) $NO_2$,
7) $NR^3R^6$,
8) $NHCOR^{41}$,
9) $NHSO_2R^5$,
10) $COR^{42}$,
11) $C(=NH)NH_2$,
12) CONHOH,
13) $C_{1-6}$ alkylthio which may be substituted with halogen,
14) $C_{1-6}$ alkylsulfinyl which may be substituted with halogen,
15) $C_{1-6}$ alkylsulfonyl which may be substituted with halogen,
16) $C_{1-3}$ alkylenedioxy optionally substituted with a) $C_{1-6}$ alkyl, or b) halogen,
17) —C(=O)— (natural α-amino acid residue), wherein said natural α-amino acid is selected from aspartic acid, alanine, phenylalanine, and asparagine, and said natural α-amino acid residue may be esterified with $C_{1-6}$ alkyl group,
18) phenyl optionally substituted with a) $C_{1-6}$ alkoxy, b) $C_{1-6}$ alkyl optionally substituted with $OR^6$, $N(C_{1-6}$ alkyl$)_2$, or $COR^{42}$, c) CN, d) $COR^{42}$, e) $C_{2-7}$ alkenyl optionally substituted with $COOR^5$, f) $NR^6R^6$, g) $NO_2$, h) $NHCOR^{41}$, i) $NHSO_2R^5$, j) $N(SO_2R^5)_2$, k) $NHCONHR^5$, l) $N(CONHR^5)_2$, m) $NHCSNHR^5$, or n) pyrrolidinyl which may be substituted with $C_{1-6}$ alkyl,
19) furyl optionally substituted with CHO,
20) thienyl optionally substituted with CHO,
21) pyrrolyl optionally substituted with CHO and $C_{1-6}$ alkoxycarbonyl,
22) dihydroxazolyl optionally substituted with $C_{1-6}$ alkyl,
23) isoxazolyl optionally substituted with $C_{1-6}$ alkyl,
24) benzothienyl,
25) pyridyl,
26) tetrazolyl, and
27) thiazolyl which may be substituted with $C_{1-6}$ alkyl;

$R^1$ and $R^2$ are independently selected from H, halogen, $OR^3$, $OCOR^5$, $NR^3R^6$, $NR^6COR^{41}$, $NHCSR^{41}$, $NHSO_2R^5$, $N_3$, $COR^{42}$, or phenyl;

or $R^1$ and $R^2$ combine with each other at the terminal thereof to form oxo;

$R^3$ is
1) hydrogen,
2) $C_{1-6}$ alkyl optionally substituted with a) OH, b) phenyl optionally substituted with halogen or $C_{1-6}$ alkoxy, c) carboxyl, d) carbamoyl, e) $NR^6R^6$, f) $C_{1-6}$ alkoxycarbonyl, g) morpholinyl, h) pyridyl, i) thienyl, or j) pyrrolidinyl optionally substituted with oxo;
3) $C_{3-6}$ cycloalkyl,
4) phenyl optionally substituted with halogen,
5) pyridyl optionally substituted with $C_{1-6}$ alkyl, or
6) morpholinyl;

$R^{41}$ is
1) $C_{1-6}$ alkyl optionally substituted with a group selected from a) $NR^6R^6$, b) carboxyl, c) —$CONR^cR^d$ where $R^c$ and $R^d$ are independently selected from hydrogen and $C_{1-6}$ alkyl, or $R^c$ and $R^d$ combine with each other at the terminals thereof to form a 3-7 membered ring together with the nitrogen to which they are attached, and said 3-7 membered ring may include additional 1-3 heteroatoms, such as oxygen, nitrogen and sulfur and may be substituted with $C_{1-6}$ alkyl, oxo, hydroxy, $C_{1-6}$ alkoxy or $NR^6R^6$, d) $C_{1-6}$ alkoxycarbonylamino, e) $C_{1-6}$ alkylsulfonylamino, f) $C_{2-7}$ alkanoylamino, and g) pyridyl;
2) $C_{1-6}$ alkoxy optionally substituted with $NR^6R^6$ or phenyl;
3) $NR^3R^6$;
4) phenyl optionally substituted with a) carboxyl, b) $C_{1-6}$ alkoxycarbonyl, or c) $NR^6R^6$,
5) $C_{3-6}$ cycloalkyl,
6) isoxazolyl optionally substituted with $C_{1-6}$ alkyl,
7) pyridyl,
8) thienyl,
9) furyl,
10) phenoxy,
11) $NR^aR^b$ (for example, pyrrolidinyl which may be substituted with a hydroxyl, and morpholinyl);

$R^{42}$ is
1) H,
2) OH;
3) $C_{1-6}$ alkyl optionally substituted with $NR^6R^6$ or phenyl,
4) $C_{1-6}$ alkoxy optionally substituted with $NR^6R^6$,
5) $NR^3R^6$,
6) $NR^aR^b$ (for example, pyrrolidinyl which may be substituted with a hydroxyl, and morpholinyl), or
7) pyridyl which may be substituted with $C_{1-6}$ alkyl;

$R^5$ is $C_{1-6}$ alkyl optionally substituted with $COR^{42}$, or aryl;

$R^6$ is hydrogen or $C_{1-6}$ alkyl optionally substituted with —$N(C_{1-6}$ alkyl$)_2$.

Among the desired compounds of the present invention, a more preferred compound is represented by the following formula (I-A):

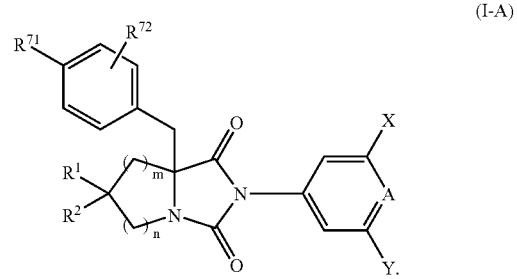

(I-A)

In the above formula (I-A), A is $=C(Z^1)$-, or $=N-$, and X and Y are independently H, halogen, $NO_2$, CN, $C_{1-6}$ alkylthio, $NR^3R^6$, or $C_{1-6}$ alkyl optionally substituted with halogen. $Z^1$ is selected from 1)H, 2) OH, 3) halogen, 4) $NR^3R^6$, 5) $NHCOR^{41}$, 6) $C_{1-6}$ alkoxy optionally substituted with a) carboxyl, b) $C_{1-6}$ alkoxycarbonyl, or c) phenyl, and 7) $COR^{42}$. $R^1$ and $R^2$ are independently H, halogen, $OR^3$, $NR^3R^6$, $NHCOR^{41}$, $NHCSR^{41}$, $NHSO_2R^5$, $N_3$, $COR^{42}$, or phenyl, or $R^1$ and $R^2$ combine with each other at the terminal thereof to form oxo. $R^{71}$ is a group selected from: 1)H, 2)OH, 3) halogen, 4) CN, 5) $C_{1-6}$ alkyl optionally substituted with halogen, $OR^6$ or $COR^{42}$, 6) $C_{1-6}$ alkoxy optionally substituted with halogen, $NR^3R^6$, pyridyl, or piperidinyl, 7) $NO_2$, 8) $NR^3R^6$, 9) $NHCOR^{41}$, 10) $NHSO_2R^5$, 11) $COR^{42}$, 12) $C(=NH)NH_2$, 13) CONHOH, 14) $C_{1-6}$ alkylthio, 15)

$C_{1-6}$ alkylsulfinyl, 16) $C_{1-6}$ alkylsulfonyl, 17) phenyl which may be substituted with a group selected from a) $C_{2-7}$ alkenyl substituted with $COOR^5$, b) $COR^{42}$, c) $C_{1-6}$ alkyl optionally substituted with $OR^6$, d) $C_{1-6}$ alkoxy and e) CN, 18) thienyl which may be substituted with CHO, 19) furyl which may be substituted with CHO, 20) tetrazolyl, 21) dihydroxazolyl, 22) pyrrolyl which may be substituted with CHO, 23) isoxazolyl substituted $C_{1-6}$ alkyl, or 24) benzothienyl. $R^{72}$ is a group selected from 1) hydrogen, 2) halogen, 3) CN, 4) $C_{1-6}$ alkyl optionally substituted with $OR^6$ or $COR^{42}$, or 5) $NO_2$, or, $R^{71}$ and $R^{72}$ combine with each other at the terminal thereof to form $C_{1-3}$ alkylenedioxy optionally substituted with halogen. m is 0, 1, or 2, and n is 0 or 1.

In a preferred compound among the compound (I-A), A is =CH— or =N—, X and Y are independently halogen, $NO_2$, $NR^3R^6$, or $C_{1-6}$ alkyl optionally substituted with halogen. One of $R^1$ and $R^2$ is H, and the other is H, OH, halogen, $NR^3R^6$, $NHCOR^{41}$, $NHCSR^{41}$, $NHSO_2R^5$, $N_3$, $COR^{42}$, or phenyl, or $R^1$ and $R^2$ combine with each other at the terminal thereof to form oxo. $R^{71}$ is a group selected from H, halogen, CN, $C_{1-6}$ alkyl optionally substituted with halogen, $C_{1-6}$ alkoxy optionally substituted with halogen, $COR^{42}$, $C_{1-6}$ alkylthio, phenyl which may be substituted with a group selected from a) $C_{2-7}$ alkenyl substituted with $COOR^5$, b) $COR^{42}$, c) $C_{1-6}$ alkyl optionally substituted with $OR^6$, d) $C_{1-6}$ alkoxy, and e) CN, thienyl which may be substituted with CHO, furyl which may be substituted with CHO, pyrrolyl which may be substituted with CHO, isoxazolyl substituted with $C_{1-6}$ alkyl. $R^{72}$ is hydrogen, or, $R^{71}$ and $R^{72}$ combine with each other at the terminal thereof to form $C_{1-3}$ alkylenedioxy substituted with halogen. m is 1, and n is 1.

In a more preferred compound among the compound (I-A), X and Y are independently halogen, and one of $R^1$ and $R^2$ is H, and the other is H, OH, $NR^3R^6$, $NHCOR^{41}$, $NHCSR^{41}$, or $COR^{42}$. $R^{41}$ is 1) $C_{1-6}$ alkyl optionally substituted with a group selected from: a) $NR^6R^6$, b) carboxyl, c) carbamoyl, d) piperazinylcarbonyl optionally substituted with $C_{1-6}$ alkyl, e) $C_{2-7}$ alkanoylamino, and f) pyridyl; 2) $C_{1-6}$ alkoxy; 3) $NR^3R^6$; 4) $C_{3-6}$ cycloalkyl; 5) pyridyl; 6) thienyl; 7) furyl or 8) pyrrolidinyl. $R^{42}$ is $NR^3R^6$ or morpholinyl. $R^{71}$ is 1) halogen, 2) CN, or 3) $C_{1-6}$ alkoxy optionally substituted with halogen, and $R^{72}$ is hydrogen.

In a further more preferred compound among the compound (I-A), X and Y are independently halogen, particularly chroline atom, and one of $R^1$ and $R^2$ is H, and the other is OH, $NHCOR^{41}$ or $COR^{42}$. $R^{41}$ is $C_{1-6}$ alkyl optionally substituted with a group selected from carboxyl, carbamoyl, and piperazinylcarbonyl substituted with $C_{1-6}$ alkyl; $NH_2$; $NH(C_{1-6}$ alkyl); pyridyl; or pyrrolidinyl. $R^{42}$ is $NH_2$, $NH(C_{1-6}$ alkyl) or morpholinyl. $R^{71}$ is $C_{1-6}$ alkoxy substituted with halogen, and $R^{72}$ is hydrogen.

Among the desired compounds of the present invention, another more preferred compound is represented by the following formula (I-B):

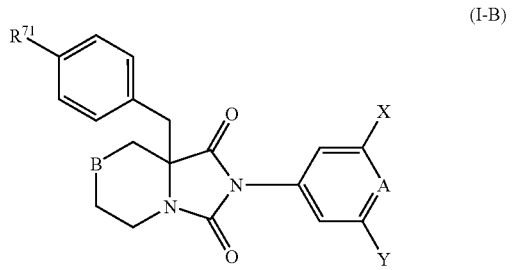

(I-B)

In the above formula (I-B), A is =CH— or =N—, B is —S—, —SO—, —$SO_2$—, —$N(R^3)$—, —$N(COR^{41})$—, —$N(CSR^{41})$—, or —$N(SO_2R^5)$—. X and Y are independently H, halogen, $NO_2$, or $C_{1-6}$ alkyl. $R^{71}$ is a group selected from 1) H, 2) halogen, 3) CN, 4) $C_{1-6}$ alkyl optionally substituted with halogen, 5) $C_{1-6}$ alkoxy optionally substituted with halogen, 6) $COR^{42}$, 7) $C_{1-6}$ alkylthio, 8) phenyl, 9) thienyl, 10) furyl, 11) pyrrolyl, 12) isoxazolyl substituted with $C_{1-6}$ alkyl, wherein said phenyl may be substituted with a group selected from a) $C_{2-7}$ alkenyl substituted with $COOR^5$, b) $COR^{42}$, c) $C_{1-6}$ alkyl optionally substituted with $OR^6$, d) $C_{1-6}$ alkoxy, and e) CN, and said thienyl, furyl and pyrrolyl may be substituted with CHO.

In a more preferred compound among the compound (I-B), B is —$N(COR^{41})$—, and X and Y are independently halogen. $R^{41}$ is 1) $C_{1-6}$ alkyl optionally substituted with a group selected from: a) $NR^6R^6$, b) carbamoyl, and d) piperazinylcarbonyl optionally substituted with $C_{1-6}$ alkyl; 2) $C_{1-6}$ alkoxy; or 3) $NR^3R^6$; and $R^{71}$ is 1) halogen, or 2) $C_{1-6}$ alkoxy optionally substituted with halogen.

Among the desired compounds of the present invention, another more preferred compound is represented by the following formula (I-C):

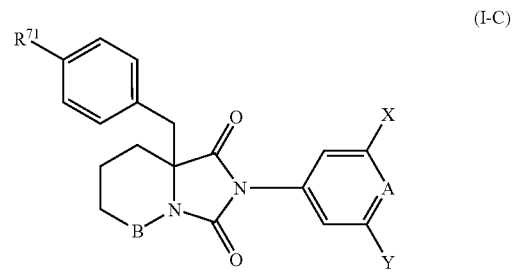

(I-C)

In the above formula (I-C), A is =CH— or =N—, B is —$N(R^3)$—, —$N(COR^{41})$—, —$N(CSR^{41})$—, or —$N(SO_2R^5)$—. X and Y are independently H, halogen, $NO_2$, or $C_{1-6}$ alkyl. $R^{71}$ is a group selected from 1) H, 2) halogen, 3) CN, 4) $C_{1-6}$ alkyl optionally substituted with halogen, 5) $C_{1-6}$ alkoxy optionally substituted with halogen, 6) $COR^{42}$, 7) $C_{1-6}$ alkylthio, 8) phenyl, 9) thienyl, 10) furyl, 11) pyrrolyl, 12) isoxazolyl substituted with $C_{1-6}$ alkyl, wherein said phenyl may be substituted with a group selected from a) $C_{2-7}$ alkenyl substituted with $COOR^5$, b) $COR^{42}$, c) $C_{1-6}$ alkyl optionally substituted with $OR^6$, d) $C_{1-6}$ alkoxy, and e) CN, and said thienyl, furyl and pyrrolyl may be substituted with CHO.

Among the desired compounds of the present invention, another more preferred compound is represented by the following formula (I-D):

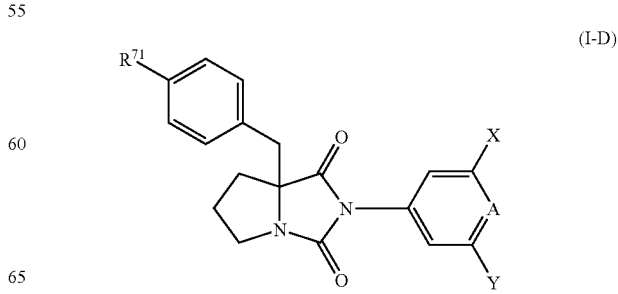

(I-D)

In the above formula (I-D), A is =CH—, or =N—. X is H or halogen, Y is 1) pyrrolyl optionally substituted with formyl, 2) phenyl optionally substituted with a) CN, b) $C_{1-6}$ alkyl optionally substituted with halogen, c) $C_{1-6}$ alkoxy optionally substituted with halogen, or 3) isoxazolyl optionally substituted with $C_{1-6}$ alkyl. $R^{71}$ is a group selected from 1) H, 2) halogen, 3) CN, 4) $C_{1-6}$ alkyl optionally substituted with halogen, 5) $C_{1-6}$ alkoxy optionally substituted with halogen, 6) $COR^{42}$, 7) $C_{1-6}$ alkylthio, 8) phenyl, 9) thienyl, 10) furyl, 11) pyrrolyl, 12) isoxazolyl substituted with $C_{1-6}$ alkyl, wherein said phenyl may be substituted with a group selected from a) $C_{2-7}$ alkenyl substituted with $COOR^5$, b) $COR^{42}$, c) $C_{1-6}$ alkyl optionally substituted with $OR^6$, d) $C_{1-6}$ alkoxy, and e) CN, and said thienyl, furyl and pyrrolyl may be substituted with CHO.

Preferred compounds of the present invetnion may be selected from the group consisting of:

(5R,7R)-5-[4-(trifluoromethoxy)benzyl]-3-(3,5-dichlorophenyl)-7-hydroxy-1,3-diazabicyclo[3.3.0]octane-2,4-dione;

(5R,7S)-5-[4-(trifluoromethoxy)benzyl]-3-(3,5-dichlorophenyl)-7-acetylamino-1,3-diazabicyclo[3.3.0]octane-2,4-dione;

(5R,7S)-5-[4-(trifluoromethoxy)benzyl]-3-(3,5-dichlorophenyl)-7-(3-carbamoylpropionylamino)-1,3-diazabicyclo[3.3.0]octane-2,4-dione;

(5R,7S)-5-[4-(trifluoromethoxy)benzyl]-3-(3,5-dichlorophenyl)-7-[3-(4-methyl-1-piperazinylcarbonyl)propionylamino]-1,3-diazabicyclo[3.3.0]octane-2,4-dione;

(5R,7S)-5-[4-(trifluoromethoxy)benzyl]-3-(3,5-dichlorophenyl)-7-nicotinoylamino-1,3-diazabicyclo[3.3.0]octane-2,4-dione;

(5R,7S)-5-[4-(trifluoromethoxy)benzyl]-3-(3,5-dichlorophenyl)-7-(1-pyrrolidinylcarbonylamino)-1,3-diazabicyclo[3.3.0]octane-2,4-dione;

(5R,7R)-5-[4-(trifluoromethoxy)benzyl]-3-(3,5-dichlorophenyl)-7-carbamoyl-1,3-diazabicyclo[3.3.0]octane-2,4-dione;

(5R,7R)-5-[4-(trifluoromethoxy)benzyl]-3-(3,5-dichlorophenyl)-7-morphlinocarbonyl-1,3-diazabicyclo[3.3.0]octane-2,4-dione;

(5R,7R)-5-[4-(trifluoromethoxy)benzyl]-3-(3,5-dichlorophenyl)-7-dimethylcarbamoyl-1,3-diazabicyclo[3.3.0]octane-2,4-dione;

(5R,7R)-5-[4-(trifluoromethoxy)benzyl]-3-(3,5-dichlorophenyl)-7-methylcarbamoyl-1,3-diazabicyclo[3.3.0]octane-2,4-dione; and (5R,7R)-5-[4-(trifluoromethoxy)benzyl]-3-(3,5-dichlorophenyl)-7-morpholinocarbamoyl-1,3-diazabicyclo[3.3.0]octane-2,4-dione.

The desired compound of the present invention may be clinically used either in a free form or in the form of pharmaceutically acceptable salts thereof. Pharmaceutically acceptable salts include an acid-addition salt with an inorganic acid or an organic acid (e.g., hydrochloride, sulfate, nitrate, hydrobromide, methanesulfonate, p-toluenesulfonate, acetate), and a salt with an inorganic base, an organic base or an amino acid (e.g., triethylamine salt, a salt with lysine, an alkali metal salt, an alkali earth metal salt and the like). Pharmaceutically acceptable salts also include an intramolecular salt thereof, or a solvate or hydrate thereof.

The compound of the present invention may be formulated into a pharmaceutical composition comprising a therapeutically effective amount of the compound as defined above and a pharmaceutically acceptable carrier or diluent. The pharmaceutically acceptable carrier or diluent may be, for example, binders (e.g., syrup, gum arabic, gelatin, sorbitol, tragacanth, polyvinylpyrrolidone), excipients (e.g., lactose, sucrose, corn starch, potassium phosphate, sorbitol, glycine), lubricants (e.g., magnesium stearate, talc, polyethylene glycol, silica) disintegrators (e.g., potato starch), wetting agents (e.g., sodium laurylsulfate), and the like.

The desired compound of the present invention or pharmaceutically acceptable salts thereof may be administered either orally or parenterally, and it may be used as a suitable pharmaceutical preparation. These pharmaceutical preparations may be in the form of a solid preparation such as a tablet, a granule, a capsule, and a powder, or in the form of a liquid preparation such as solution, suspension, and emulsion, when administered orally. When administered parenterally, the pharmaceutical preparation may be in the form of suppository, an injection preparation or an intravenous drip preparation using distilled water for injection, a physiological salt solution, an aqueous glucose solution, and so on, and an inhalation by a conventional process.

The dose of the desired compound of the present invention or a pharmaceutically acceptable salt thereof varies depending on an administration method, age, sex, body weight, and condition of a patient, but, in general, the daily dose is preferably about 0.1 to 100 mg/kg/day, particularly preferably 1 to 100 mg/kg/day.

The compound of the present invention has an excellent activity in inhibiting $\alpha_L\beta_2$ mediated cell adhesion, and can be used for treating or preventing $\alpha_L\beta_2$ adhesion mediated conditions in a mammal such as a human.

The compound of the present invention may be used for treatment or prevention of numerous inflammatory diseases such as rheumatoid arthritis, asthma, allergy conditions, adult respiratory distress syndrome, AIDS, cardiovascular diseases, thrombosis or harmful platelet aggregation, reocclusion following thrombolysis, allograft rejection, reperfusion injury, stroke, psoriasis, eczema, skin inflammatory diseases such as contact dermatitis and atopic dermatitis, osteoporosis, osteoarthritis, atherosclerosis (including graft arteriosclerosis after transplantation), neoplastic diseases including metastasis of neoplastic or cancerous growth, wound healing enhancement, eye diseases such as detaching retina, Type I diabetes, multiple sclerosis, systemic lupus erythematosus (SLE), inflammatory and immunoinflammatory conditions including ophthalmic inflammatory conditions and inflammatory bowel diseases (Crohn's disease, ulcerative colitis), regional enteritis, Sjogren's Syndrome, and other autoimmune diseases, pancreatitis, delayed graft function, intimal hyperplasia; myocardial reinfarction or restenosis after surgery such as percutaneous transluminal coronary angioplasty (PTCA).

The compound of the present invention may also be used for cancer, such as radiation induced pneumonitis.

The compound of the present invention may also be used for transplantation, including the rejection (i.e., chronic rejection and acute rejection) after transplantation, and host vs. graft or graft vs. host diseases.

The compound of the present invention may be preferably used for treatment or prevention of psoriasis, rheumatoid arthritis, inflammatory bowel diseases (Crohn's disease, ulcerative colitis), systemic lupus erythematosus, atopic dermatitis, Sjogren's Syndrome, rejection after transplantation, and graft vs. host disease.

According to the present invention, the desired compound (I) can be prepared by the following methods:

Method A:

The desired compound (I) or a pharmaceutically acceptable salt thereof may be prepared by:

(1) cyclizing the compound of the formula (II):

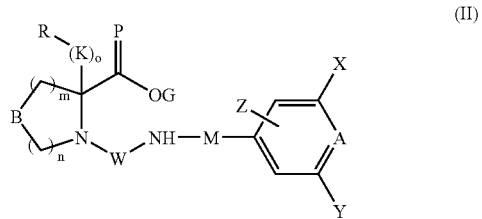

wherein OG is a hydroxyl group, a protected hydroxyl group, or a resin-bound hydroxyl group, and the other symbols are the same as defined above, and (2) converting the resulting cyclized compound into a pharmaceutically acceptable salt thereof by a conventional method, if desired.

When OG is a protected hydroxyl group, the protecting group can be selected from the conventional protecting groups for a carboxyl group (i.e., $C_{1-6}$ alkyl group, benzyl group).

When OG is a resin-combined hydroxyl group, the resin may be selected from resin polymers which are conventionally used for a solid phase peptide synthesis. Merrifield resin may be given as an example of such resin polymers.

The cyclization can be carried out in the presence of an acid or a base in a suitable solvent.

The acid can be selected from organic acids (i.e., p-toluenesulfonic acid, and trifluoroacetic acid) and inorganic acids (i.e., hydrochloric acid, sulfuric acid, and nitric acid).

The base can be selected from conventional bases such as alkali metal alkoxide (e.g., NaOEt, NaOMe).

The solvent can be selected from any one which does not disturb the cyclization reaction, for example, $CH_2Cl_2$, THF, $CH_3CN$, DMF, alcohols (methanol, ethanol, etc.) or a mixture thereof. The reaction is carried out at a temperature of 0° C. to boiling point of the solvent, preferably at 50° C. to 100° C.

The cyclization of the compound (II) can be also carried out in the presence of a condensing reagent with or without a base in a suitable solvent or without a solvent. The condensing reagent can be selected from $SOCl_2$ and conventional condensing reagents which can be used for a peptide synthesis, for example, BOP—Cl, BOP reagent, DCC, EDC or CDI.

The base can be selected from an organic base (e.g., DIEA, DMAP, DBU, $Et_3N$), an alkali metal hydride (e.g., NaH, LiH), an alkali metal carbonate (e.g., $Na_2CO_3$, $K_2CO_3$), an alkali metal hydrogen carbonate (e.g., $NaHCO_3$, $KHCO_3$), an alkali metal amide (e.g., $NaNH_2$), an alkali metal alkoxide (e.g., NaOMe, KOMe), a $C_{1-6}$ alkyl alkali metal salt(e.g., n-BuLi, t-BuLi), an alkali metal hydroxide (e.g., NaOH, KOH), an alkaline earth metal hydroxide (e.g., $Ba(OH)_2$), and the like.

The solvent can be selected from any one which does not disturb the cyclization reaction, for example, $CH_2Cl_2$, THF, DMF or a mixture thereof. The reaction is carried out at a temperature of 0° C. to the boiling point of the solvent, preferably at room temperature.

In this method, any functional group in the compound (II) can be protected with a conventional protecting group before the cyclization reaction. The protecting group can be removed after the cyclization by a conventional method according to the protecting group to be removed, for example, hydrolysis with a base or an acid, acid treatment, and catalytic reduction.

Method B:

The desired compound (I) or a pharmaceutically acceptable salt thereof, may be prepared by:

(1) reacting the compound of the formula (III):

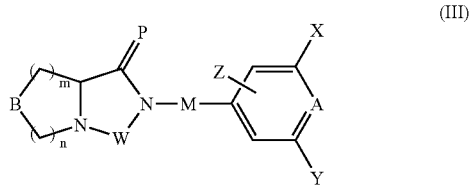

wherein the symbols are the same as defined above, with the compound of the formula (IV):

$$R—(K)_o—L \quad (IV)$$

wherein L is a leaving group and the other symbols are the same as defined above, and (2) converting the resulting compound into a pharmaceutically acceptable salt thereof by a conventional method, if desired.

The leaving group L can be selected from conventional leaving groups, such as a halogen atom (e.g., chlorine, bromine, iodine), an alkylsulfonyloxy group (e.g., methylsulfonyloxy group) and an arylsulfonyloxy group (e.g., p-tolylsulfonyloxy group).

The condensation reaction can be carried out in the presence of a base in a suitable solvent.

The base can be selected from conventional bases such as alkali metal hydride (i.e., NaH, KH), alkali metal alkoxide (i.e., NaOMe, NaOEt) and alkali metal amide (i.e., $NaNH_2$, LDA, KHMDS).

The solvent can be selected from any one which does not disturb the condensation reaction, for example, DME, THF, DMF, HMPA or a mixture thereof. The reaction can be carried out at a temperature of −78° C. to room temperature.

In this method, any functional group in the compound (III) and comound (IV) can be protected with a conventional protecting group before the condensation reaction, if necessary. The protecting group can be removed after the condensation by a conventional method according to the protecting group to be removed, for example, hydrolysis with a base or an acid, acid treatment, and catalytic reduction.

Method C:

The desired compound (I) or a pharmaceutically acceptable salt thereof, may be prepared by:

(1) reacting the compound of the formula (V):

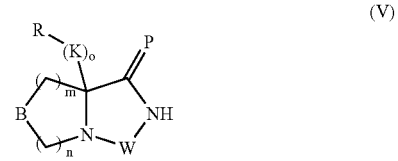

wherein the symbols are the same as defined above, with the compound of the formula (VI):

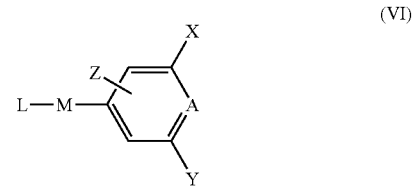

wherein the symbols are the same as defined above, and (2) converting the resulting compound into a pharmaceutically acceptable salt thereof by a conventional method, if desired.

The leaving group L can be selected from conventional leaving groups such as those mentioned in Method B.

The condensation reaction can be carried out in the presence of a base in a suitable solvent.

The base can be selected from conventional bases such as alkali metal hydride (i.e., NaH, KH), alkali metal alkoxide (i.e., NaOMe, NaOEt) and alkali metal amide (i.e., NaNH$_2$, LDA, KHMDS).

The solvent can be selected from any one which does not disturb the condensation reaction, for example, DME, THF, DMF, HMPA or a mixture thereof. The reaction is carried out at a temperature of −78° C. to room temperature.

In this method, any functional group in the compound (V) and comound (VI) can be protected with a conventional protecting group before the condensation reaction, if necessary. The protecting group can be removed after the condensation by a conventional method according to the protecting group to be removed, for example, hydrolysis with a base or an acid, acid treatment, and catalytic reduction.

Method D:

Among the desired compound (I), the compound (I) wherein K is —CH(OH)—, —C(=O)— or —CF$_2$— may be prepared according to the following method.

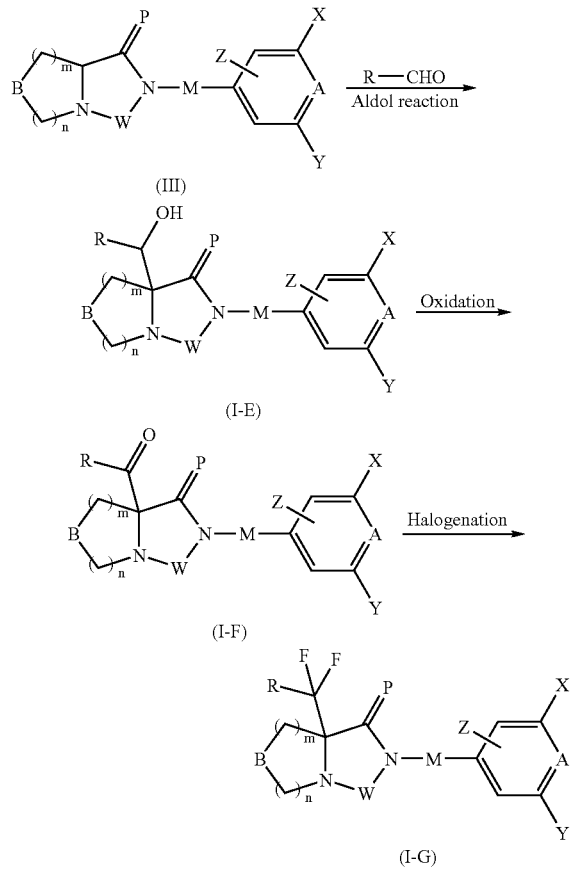

(The symbols are the same as defined above.)

Step 1: Among the desired compound (I), the compound (I-E) can be prepared by reacting the compound (III) with the compound of the formula (VII):

R—CHO  (VII)

wherein R is the same as defined above.

The reaction can be carried out by a conventional aldol reaction. For example, the reaction can be carried out in the presence of a base (e.g., LDA, KHMDS, n-BuLi, NaH, KH, MeONa) in a suitable solvent (THF, DMF, MeOH) at a temperature of −78° C. to room temperature.

Step 2: Among the desired compound (I), the compound (I-F) can be prepared by oxidating the compound (I-E).

The oxidation reaction can be carried out by a conventional method. For example, the oxidation reaction can be carried out by reacting the compound (I-E) with an oxidating reagent (e.g., PCC, PDC, "Dess-Martin Periodinane" reagent) in a suitable solvent (e.g., CH$_2$Cl$_2$, toluene) at a temperature of 0° C. to 50° C.

Step 3: Among the desired compound (I), the compound (I-G) can be prepared by halogenating the compound (I-F).

The halogenation reaction can be carried out by reacting the compound from step 2 with a halogenating reagent (e.g.,(diethylamino)sulfur trifluoride) in a suitable solvent (e.g., CCl$_4$) at a temperature of 0° C. to 50° C.

The compound (I) of the present invention can be converted into each other in accordance with the following Schemes 1 to 6:

Scheme 1.

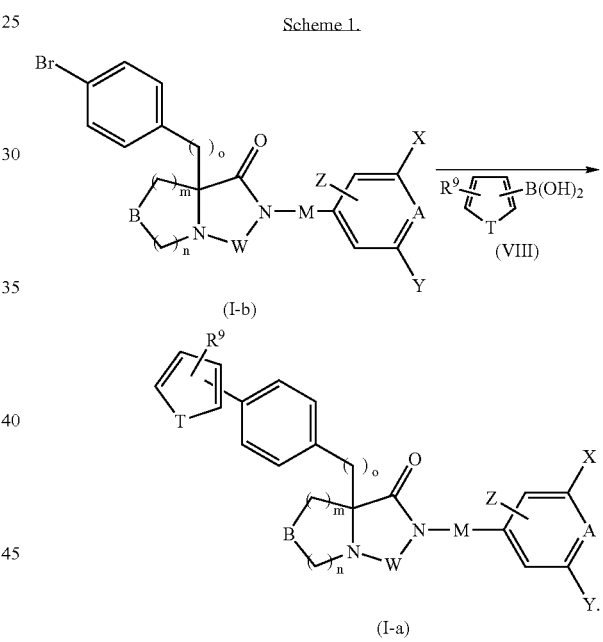

(In Scheme 1, T is —O—, —S—, —NBoc—, —CH=CH— or —CH=N—, R$^9$ is H, CN, COCH$_3$ or CHO, and the other symbols are the same as defined above.)

The compound (I-a) can be prepared by coupling the compound (I-b) with the compound (VIII).

The coupling reaction can be carried out by a conventional aryl coupling method such as Suzuki coupling method. References of Suzuki coupling method are: (a) Suzuki et al., *Synth. Commun.* 1981, 11, 513, (b) Suzuki *Pure and Appl. Chem.* 1985, 57, 1749-1758, (c) Suzuki et al., *Chem. Rev.* 1995, 95, 2457-2483, (d) Shieh et al., *J. Org. Chem.* 1992, 57, 379-381, (e) Martin et al., *Acta Chemica Scandinavica*, 1993, 47, 221-230.

For example, the coupling reaction can be carried out in a suitable solvent in the presence of a Pd catalyst and a base. As a Pd catalyst, Pd(PPh$_3$)$_4$ may be preferably used. The base can be selected from conventional inorganic bases such as $K_2CO_3$ and $Na_2CO_3$. The solvent can be selected from any one which does not disturb the coupling reaction, for example, toluene, DME, DMF, $H_2O$ or a mixture thereof. The coupling reaction can be carried out, for example, at a temperature of room temperature to 100° C., preferably at a temperature of 80° C. to 100° C.

Compounds of (I-a) where T is NBOC can be converted to compounds where T=NH, which can be further transformed to NR" (wherein R" is $C_{1-6}$ alkyl, $C_{1-6}$ alkylsulfonyl, arylsulfonyl, heteroarylsulfonyl, $C_{2-7}$ alkanoyl (wherein said $C_{1-6}$ alkyl, $C_{1-6}$ alkylsulfonyl, arylsulfonyl, heteroarylsulfonyl, $C_{2-7}$ alkanoyl is optionally substituted with, for example, amino or carboxy), or CONHR'" (wherein R'" may be $C_{1-6}$ alkyl, aryl and said $C_{1-6}$ alkyl and ary may be substituted). Removal of BOC group can be carried out by a conventional method (e.g., acid (TFA) treatment) in a suitable solvent. Transformation from NH to NR" may be carried out by the condensation reaction of compound (I-a) and appropreate halides such as $C_{1-6}$ alkyl halide, $C_{1-6}$ alkylsulfonyl halide, arylsulfonyl halide, heteroarylsulfonyl halide, $C_{2-7}$ alkanoyl halide in a suitable solvent (e.g., $CH_2Cl_2$, THF, DMF, toluene) in the presence of a base (e.g., NaOH, KOH, $K_2CO_3$, $Na_2CO_3$, NaH). The reaction can be carried out at a temperature of 0° C. to 100° C.

Step 2: The compound (I-d) can be prepared by the amination of the compound (I-c). The amination can be carried out by a usual method, for example, by 1) halogenating the compound (I-c) with a halogenating reagent in a suitable solvent, and 2) reacting the resulting halogenated compound with a requisite amine with or without a base in a suitable solvent. In the halogenation of the compound (I-c) with a halogenating reagent, the halogenating reagent can be selected from conventional halogenating reagents such as thionyl chloride. The solvent can be selected from any one which does not disturb the halogenation, for example, toluene, $CH_2Cl_2$, THF, $Et_2O$ or a mixture thereof. The reaction can be carried out at a temperature of –78° C. to 50° C., preferably at a temperature of 0° C. to room temperature. In the reaction of the halogenated compound thus obtained and the amine, the base can be selected from conventional inorganic bases (i.e., $NaHCO_3$, $K_2CO_3$) and organic bases (i.e., pyridine, $Et_3N$, N,N-dimethylaniline, i-$Pr_2NEt$). The solvent can be selected from any one which does not disturb the reaction, for example, toluene, DMF, $CH_2Cl_2$, DME, THF, $Et_2O$ or a mixture thereof. The reaction can be carried out at a temperature of –78° C. to 50° C., preferably at a temperature of 0° C. to room temperature.

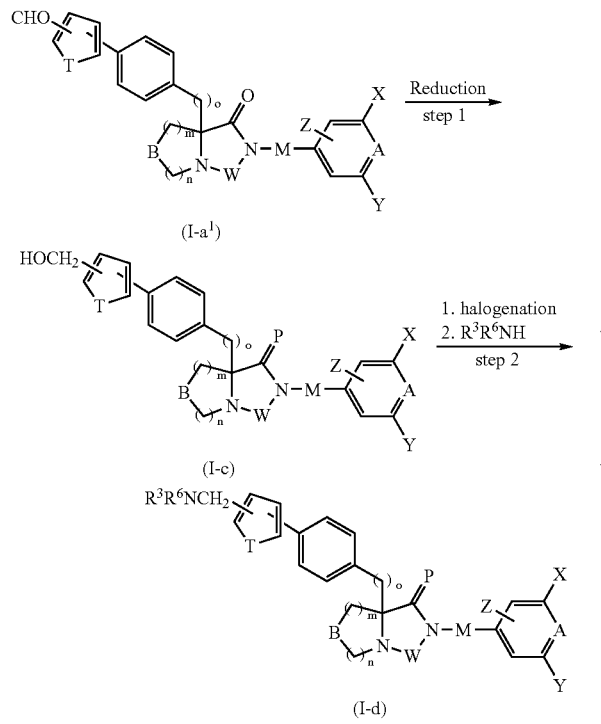

Scheme 2.

(In the Scheme 2, the symbols are the same as defined above.)

Step 1: The compound (I-c) can be prepared by reducing the compound (I-a¹). The reduction can be carried out by a conventional method, for example, by reacting the compound (I-a¹) with $NaBH_4$ in a suitable solvent. The solvent can be selected from any one which does not disturb the reduction, for example, toluene, DME, THF, $Et_2O$ or a mixture thereof. The reaction can be carried out at a temperature of –78° C. to 50° C., preferably at a temperature of 0° C. to room temperature.

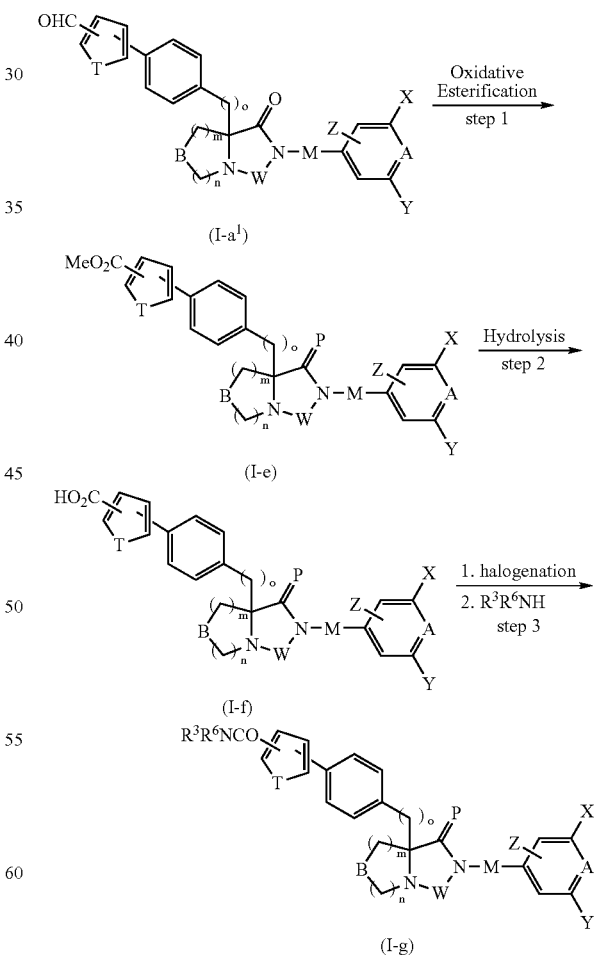

Scheme 3.

(In the Scheme 3, the symbols are the same as defined above.)

Step 1: The compound (I-e) can be prepared by the oxidative esterification of the compound (I-a$^1$). The reaction can be carried out by a usual method, for example, by reacting the compound (I-a$^1$) with an oxidizing reagent such as $MnO_2$ in the presence of an alkali metal cyanide such as NaCN, MeOH and an acid in a suitable solvent. As the acid, acetic acid can be preferably used. The solvent can be selected from any one which does not disturb the reaction, for example, MeOH, AcOH, $H_2O$ or a mixture thereof. The reaction can be carried out at a temperature of 0° C. to 50° C., preferably at a temperature of 0° C. to room temperature.

Step 2: The compound (I-f) can be prepared by hydrolyzing the compound (I-e). The hydrolysis can be carried out by a usual procedure, for example, by treating the compound (I-e) with a base in a suitable solvent. The base can be selected from conventional inorganic bases such as LiOH, NaOH and KOH. The solvent can be selected from any one which does not disturb the hydrolyzing reaction, for example, THF, MeOH, EtOH, $H_2O$ or a mixture thereof. The reaction can be carried out at a temperature of −78° C. to 50° C., preferably at a temperature of 0° C. to room temperature.

Step 3: The compound (I-g) can be prepared by the amidation of the compound (I-f). The amidation can be carried out by a usual method. For example, the compound (I-g) can be prepared by 1) reacting the compound (I-f) with a halogenating reagent, and 2) reacting the acid chloride compound thus obtained with a requisite amine in the presence or absence of a base in a suitable solvent. The reaction of the compound (I-f) with a halogenating reagent can be carried out at a reflux temperature. The halogenating reagent can be selected from conventional halogenating reagents such as thionyl chloride. In the reaction of the acid chloride compound and the amine, the base can be selected from conventional inorganic bases such as $K_2CO_3$, $Na_2CO_3$ and $NaHCO_3$, and conventional organic bases such as pyridine, $Et_3N$, i-$Pr_2EtN$, aniline, N,N-dimethylaniline. The solvent can be selected from any one which does not disturb the coupling reaction, for example, toluene, $CH_2Cl_2$, THF, $Et_2O$, $H_2O$ or a mixture thereof. The reaction can be carried out at a temperature of −78° C. to 50° C., preferably at a temperature of 0° C. to room temperature.

Scheme 4.

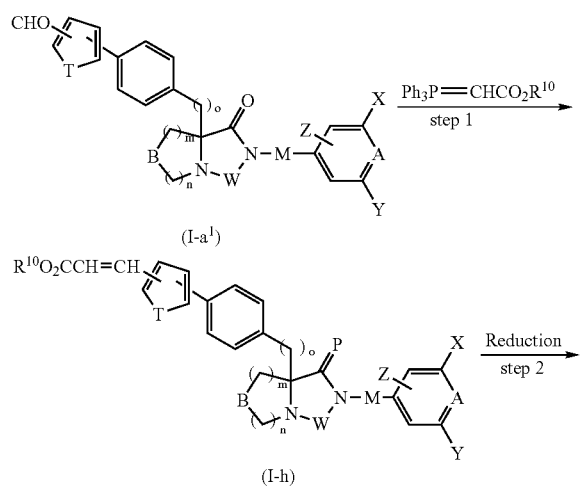

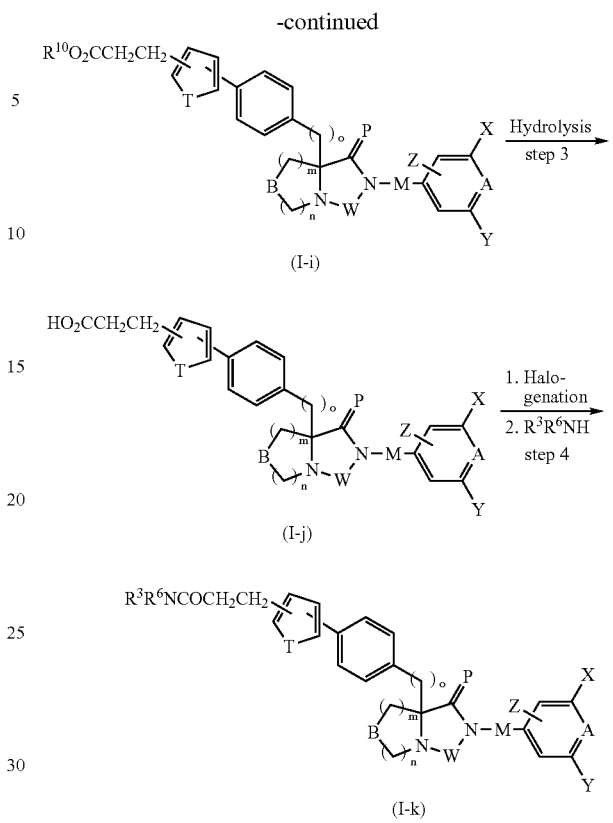

(In the Scheme 4, $R^{10}$ is $C_{1-6}$ alkyl, and the other symbols are the same as defined above.)

Step 1: The compound (I-h) can be prepared by reacting the compound (I-a$^1$) with a conventional Wittig reagent, $Ph_3P=CHCO_2R^{10}$. The solvent can be selected from any one which does not disturb the coupling reaction, for example, toluene, DMSO, DMF, THF, $Et_2O$ or a mixture thereof. The Wittig reaction can be carried out at a temperature of 0° C. to 150° C., preferably at a temperature of room temperature to 120° C.

Step 2: The compound (I-i) can be prepared by reducing the compound (I-h). The reduction can be carried out by a usual method, for example, by treating the compound (I-h) with a reducing reagent such as $NaBH_4$ in the presence of $NiCl_2$ in a suitable solvent. The solvent can be selected from any one which does not disturb the reduction reaction, for example, MeOH, EtOH, AcOH, THF, $Et_2O$, $H_2O$ or a mixture thereof. The reaction can be carried out at a temperature of −78° C. to 50° C., preferably at a temperature of 0° C. to room temperature.

Step 3: The compound (I-j) can be prepared by hydrolyzing the compound (I-i). The hydrolysis can be carried out in a similar method as described in the Scheme 3, step 2.

Step 4: The compound (I-k) can be prepared by the amidation of the compound (I-j). The amidation can be carried out in a similar method as described in the Scheme 3, step 3.

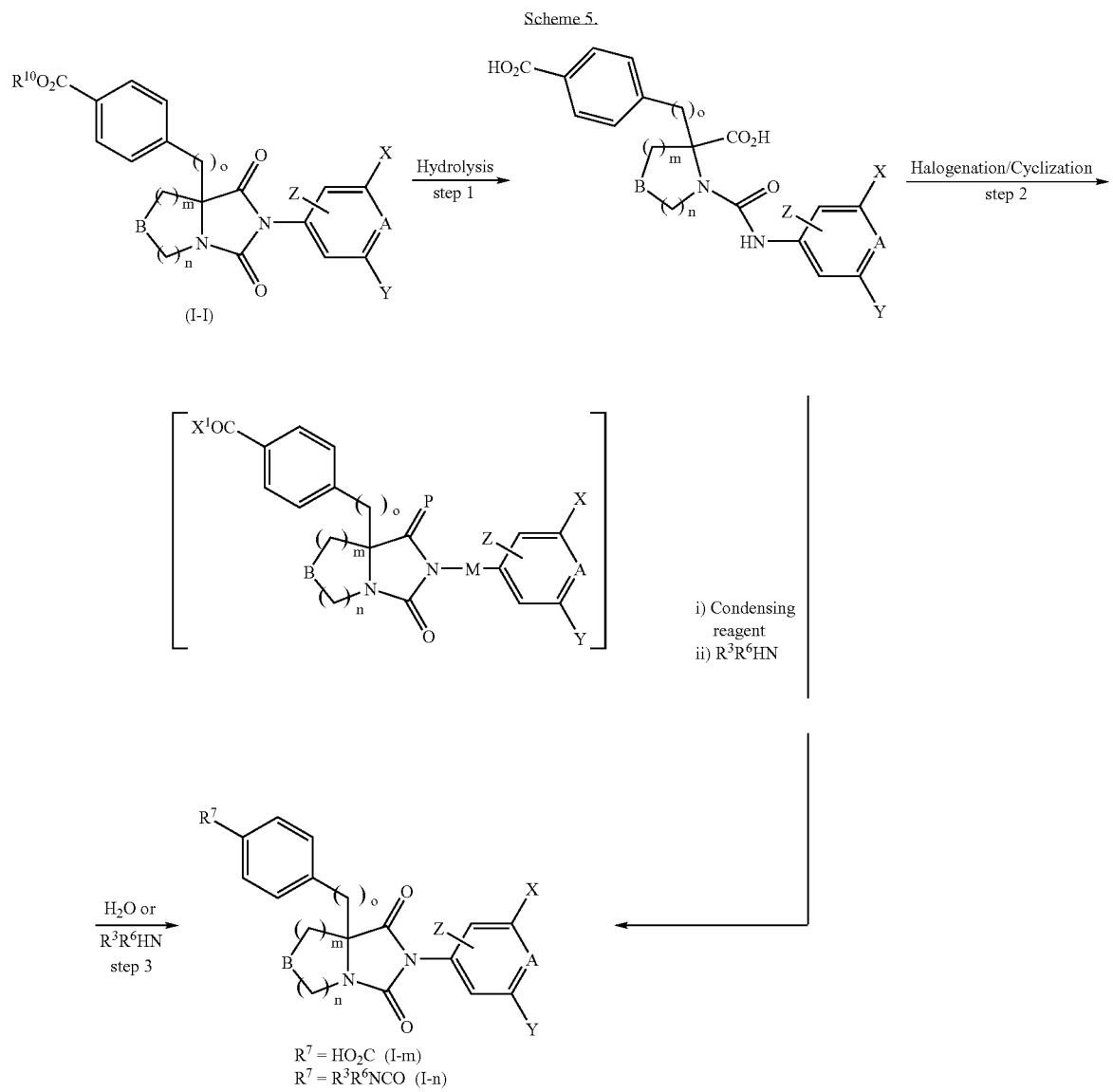

(In the Scheme 5, $X^1$ is a halogen, and the other symbols are the same as defined above.)

Among the compound (I), the compound (I-m) and the compound (I-n) can be prepared by the steps comprising 1) hydrolyzing the compound (I-1), 2) reacting the resulting compound with a conventional halogenating reagent such as thionyl chloride, and 3) reacting the resulting cyclized acid chloride compound with $H_2O$ or a requisite amine. These Steps 1 to 3 can be carried out by a similar method as described in the Scheme 3, steps 2 and 3.

An alternative procedure for the preparation of the compound (I-n) from the compound (I-1) comprises the steps of 1) hydrolysis of the compound (I-1), and 2) cyclization of the resulting diacid with condensing reagent followed by treatment with the requisite amine.

The hydrolysis can be carried out as described in the Scheme 3, step 2. The cyclization reaction can be carried out in the presence of a condensing reagent with or without a base in a suitable solvent or without a solvent. The condensing reagent can be selected from any one which can be used for a conventional amide bond synthesis, for example, BOP—Cl, BOP reagent, DCC, EDC or CDI, preferably EDC.

The base can be selected from an organic base (e.g., DIEA, DMAP, DBU, $Et_3N$), an alkali metal hydride (e.g., NaH, LiH), an alkali metal carbonate (e.g., $Na_2CO_3$, $K_2CO_3$), an alkali metal hydrogen carbonate (e.g., $NaHCO_3$, $KHCO_3$), an alkali metal amide (e.g., $NaNH_2$), an alkali metal alkoxide (e.g., NaOMe, KOMe), a lower alkyl alkali metal salt(e.g., n-BuLi, t-BuLi), an alkali metal hydroxide (e.g., NaOH, KOH), an alkaline earth metal hydroxide (e.g., $Ba(OH)_2$), and the like.

The solvent can be selected from any one which does not disturb the condensation reaction, for example, $CH_2Cl_2$, THF, DMF or a mixture thereof. The reaction is carried out at a temperature of 0° C. to room temperature, preferably at room temperature.

Scheme 6.

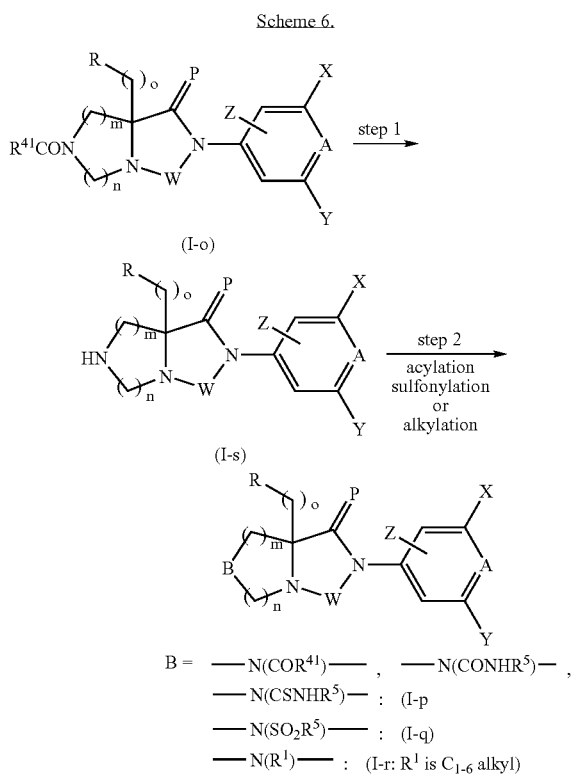

(In the Scheme 6, the symbols are the same as defined above.)

Among the desired compound (I), the compound (I-p), (I-q), or (I-r) can be prepared from the compound (I-o) by 1) removing the $COR^{41}$ group, and 2) acylating, sulfonylating or alkylating the resulting compound (I-s).

Step 1: Removal reaction can be carried out by a conventional method, which is selected according to the type of the group to be removed, e.g., 1) catalytic reduction using a catalyst such as palladium on activated carbon under a hydrogen atmosphere, 2) a treatment with an acid such as hydrogen chloride or TFA, at room temperature or with heating in an organic solvent, e.g., $CH_2Cl_2$, THF, MeOH, EtOH and MeCN, or without an organic solvent.

Step 2:

Acylation: The compound (I-p) (B is —N($COR^{41}$)—, —N($CONHR^5$)— or —N($CSNHR^5$)—) can be prepared by the N-acylation of the compound (I-s). The N-acylation reaction can be carried out by a conventional method using 1) an acylating reagent, e.g., a $C_{2-7}$ alkanoyl halide, a $C_{1-7}$ alkanoic acid anhydride, a $C_{1-6}$ alkyl halogenoformate such as a $C_{1-6}$ alkyl chloroformate, an aryl carbonyl halide, a chlorosulfonyl isocyanate, a $C_{1-6}$ alkyl isocyanate, a $C_{1-6}$ alkyl isothiocyanate, an aryl isocyanate or an isocyanate, or 2) a condensing reagent (e.g., CDI, thioCDI) and a requisite amine or alcohol. The N-acuylation can be carried out at a temperature of 0° C. to 100° C. (preferably at a temperature of room temperature to 90° C.) in the presence or absence of a base (e.g., DIEA, DMAP, pyridine, $NaHCO_3$, $Na_2CO_3$, $KHCO_3$, $K_2CO_3$) in an organic solvent (e.g., THF, $CH_3CN$, $CH_2Cl_2$, DMF, toluene, acetone and the mixture thereof).

Sulfonylation: The compound (I-q) (B is —N($SO_2R^5$)—) can be prepared by the N-sulfonylation of the compound (I-s). The N-sulfonylation reaction can be carried out by a conventional method using a requisite $C_{1-6}$ alkylsulfonyl halide or an arylsulfonyl halide in the presence of a base (e.g., $Et_3N$, DIEA, $NaHCO_3$, $KHCO_3$, $Na_2CO_3$, $K_2CO_3$) at a temperature of 0° C. to room temperature (preferably at room temperature) in an organic solvent (e.g., $CH_2Cl_2$, THF, DMF, $CH_3CN$, toluene, acetone and the mixture thereof).

Alkylation: The compound (I-r) (B is —N($R^1$)—, $R^1$ is $C_{1-6}$ alkyl) can be prepared by the reductive alkylation of the compound (I-s). The reductive alkylation can be carried out by a conventional method, for example, using aldehydes (e.g., formaldehyde, acetaldehyde), a reducing agent (e.g., sodium cyanoborohydride, $NaBH_4$) and an acid (e.g., HCl) at room temperature in an organic solvent (e.g., MeOH, EtOH, THF, dioxane) or $H_2O$, or the mixture thereof.

The desired compound (I) of the present invention can be also converted into each other in accordance with one of the following procedures according to the type of the substituent thereof.

Procedure A: Acylation of Hydroxyl Group (A-1) The compound (I) wherein Z, $Z^1$, $R^1$, $R^2$, $R^3$, $R^{41}$, $R^{42}$, $R^5$, $R^6$ or the substituent of R is a substituted or unsubstituted $C_{2-7}$ alkanoyloxy group can be prepared by the acylation of the compound (I) wherein the corresponding Z, $Z^1$, $R^1$, $R^2$, $R^3$, $R^{41}$, $R^{42}$, $R^5$, $R^6$ or the substituent of R is hydroxy. The acylation can be carried out using a $C_{2-7}$ alkanoyl halide which may be substituted in the presence of a base (e.g., $Et_3N$, DIEA, $NaHCO_3$, $KHCO_3$, $Na_2CO_3$, $K_2CO_3$, $KHCO_3$, Cs2CO3) at a temperature of room temperature to 50° C. in a suitable solvent (e.g., $CH_2Cl_2$, THF, DMF, $CH_3CN$, toluene).

(A-2) Among the compound (I) wherein B is —CH($OCOR^5$)— can be prepared by the acylation of the compound (I) wherein B is —CH(OH)—. The acylation reaction can be carried out using $R^5COCl$ in the presence of a base (e.g., $Et_3N$, DIEA, $NaHCO_3$, $KHCO_3$, $Na_2CO_3$, $K_2CO_3$, $KHCO_3$, $Cs_2CO_3$) at a temperature of 0° C. to 50° C. in an organic solvent (e.g., $CH_2Cl_2$, THF, DMF, $CH_3CN$, toluene).

Procedure B: Wittig Reaction

Among the compound (I) wherein B is —C($R^1$) ($R^2$)— and $R^1$ and $R^2$ combine with each other at the terminal thereof to form methylene substituted with $C_{1-6}$ alkoxycarbonyl can be prepared by the Wittig reaction of the compound (I) wherein B is —C(=O)—. The Wittig reaction can be carried out by a conventional method using a Wittig reagent, for example, (triphenyl-phosphoranylidene)acetic acid $C_{1-6}$ alkyl ester at a room temperature of 50° C. to 100° C. in an organic solvent (e.g., toluene, THF).

Procedure C: Azidation

The compound (I) wherein B is —CH($N_3$)— can be prepared from the compound (I) wherein B is —CH(OH)—. This procedure comprises steps of 1) converting hydroxyl group to an eliminating group such as methanesulfonyloxy group and toluenesulfonyl group, and 2) reacting the compound from step-1 with an alkali metal azide. Step-1 can be carried out by reacting the compound (I) wherein B is —CH(OH)— with methanesulfonyl chloride or toluenesulfonyl chloride in the presence of a base (e.g., $Et_3N$, DIEA, $NaHCO_3$, $KHCO_3$, $Na_2CO_3$, $K_2CO_3$, $KHCO_3$, $Cs_2CO_3$) at a temperature of 0° C. to 50° C. in an organic solvent (e.g., $CH_2Cl_2$, THF, DMF, $CH_3CN$, toluene). Step-2 can be carried out at a temperature of 0° C. to 100° C. in an organic solvent (e.g., $CH_2Cl_2$, THF, DMF, $CH_3CN$, toluene)

Procedure D: Reduction of Azido Group

The compound (I) wherein B is —CH($NH_2$)— can be prepared by reducing the compound (I) wherein B is —CH ($N_3$)—. The reduction can be carried out by chemical reduction using metal and inorganic acid (e.g., Fe/HCl, Sn/HCl, $SnCl_2$/HCl, Zn/AcOH and the like) at a temperature of 0° C. to 50° C. in an organic solvent (e.g., MeOH, EtOH, AcOH), water or a mixture thereof. The reduction reaction can be carried out at a temperature of 0° C. to 100° C. in an organic solvent (e.g., $CH_2Cl_2$, THF, DMF, $CH_3CN$, toluene). In addition, the reduction can be carried out under catalytic hydrogenation condition (e.g., $H_2$/Pd—C). The reduction reaction can be carried out at room temperature in an organic solvent (e.g., EtOAc, THF, EtOH).

Procedure E: Acylation of Amino Group (E-1) The compound (I) wherein Z, $Z^1$, $R^1$, $R^2$, $R^3$, $P^{41}$, $R^{42}$, $R^5$, $R^6$ or the substituent of R is a substituted or unsubstituted $C_{2-7}$ alkanoylamino group can be prepared by the acylation of the compound (I) wherein the corresponding Z, $Z^1$, $R^1$, $R^2$, $R^3$, $R^{41}$, $R^{42}$, $R^5$, $R^6$ or the substituent of R is amino. The acylation reaction can be carried out by a usual method as described in the Scheme 6, step 2.

(E-2) The compound (I) wherein B is —CH(NH-COR$^{41}$)—, —CH(NHCONR$^3$R$^6$)— or —CH(NHCSNR$^3$R$^6$)—, and/or R has NHCOR$^{41}$ as a substituent thereof can be prepared by the N-acylation of the compound (I) wherein B is —CH(NH$_2$)— and/or R has NH$_2$ as a substitutent.

The N-acylation can be performed with using 1) an acylating reagent (e.g., R$^{41}$COCl, R$^3$R$^6$NCO, R$^3$R$^6$NCS) or 2) a condensing reagent (e.g., CDI, EDC) and a requisite acid (e.g., R$^{41}$COOH). The reaction can be carried out by a usual method as described in the Scheme 6, step 2.

Procedure F: Sulfonylation of Amino Group (F-1) The compound (I) wherein Z, $Z^1$, $R^1$, $R^2$, $R^3$, $R^{41}$, $R^{42}$, $R^5$, $R^6$ or the substituent of R is a substituted or unsubstituted $C_{1-6}$ alkanesulfonylamino group can be prepared by the sulfonylation of the compound (I) wherein the corresponding Z, $Z^1$, $R^1$, $R^2$, $R^3$, $R^{41}$, $R^{42}$, $R^5$, $R^6$ or the substituent of R is amino. The sulfonylation reaction can be carried out by a usual method as described in the Scheme 6, step 2.

(F-2) The compound (I) wherein B is —CH(NHSO$_2$R$^5$)— and/or R has NHSO$_2$R$^5$ as a substituent can be prepared by the N-sulfonylation of the compound (I) wherein B is —CH(NH$_2$)— and/or R has NH$_2$ as a substituent. The N-sulfonylation reaction can be carried out by a usual method as described in the Scheme 6, step 2.

Procedure G: Preparation of Oxo Group

The compound (I) wherein B is —C(=O)— can be prepared by oxidating the compound (I) wherein B is —CH(OH)—. The oxidation can be carried out in the presence of an oxidating reagent (e.g., PDC, PCC, Swern reagent, and MnO$_2$) at a temperature of −78° C. to 50° C. in an organic solvent (e.g., CH$_2$Cl$_2$, THF, DMF, CH$_3$CN, toluene)

Procedure H: Elimination of Azido Group

The compound (I) wherein B is —CH=CH— can be prepared from the compound (I) wherein B is —CH(N$_3$)— by β-elimination of N$_3$ and hydrogen attached to the carbon atom which is adjacent to B. The elimination reaction can be carried by a usual manner, preferably in the presence of a base at a temperature of 0° C. to 50° C. in an organic solvent (e.g., CH$_2$Cl$_2$, THF, DMF, CH$_3$CN, toluene).

Procedure I: Reduction of Nitro Group

The compound (I) wherein R has NH$_2$ as a substituent thereof can be prepared by the reduction of the compound (I) wherein R has NO$_2$ as a substituent. The reduction reaction can be carried out by a conventional method. Such method can be selected from, for example, 1) a catalytic reduction using a catalyst (e.g., Raney-nickel, and a palladium on activated carbon) under a hydrogen atmosphere at room temperature in an organic solvent (e.g., methanol, H$_2$O or the mixture thereof), 2) chemical reduction using metal and inorganic acid (e.g., Fe/HCl, Sn/HCl, SnCl$_2$/HCl) or 3) reduction with a reducing agent (e.g., Na$_2$S$_2$O$_4$) in a suitable solvent (e.g., methanol, ethanol, H$_2$O or the mixture thereof) or without a solvent at a temperature of 0° C. to 80° C.

Procedure J: Demethylation of Methoxy Group

The compound (I) wherein Z or $Z^1$ is hydroxy and/or R has hydroxyl as a substituent thereof can be prepared by the demethylation of the compound (I) wherein Z or $Z^1$ is methoxy and/or R has methoxy as a substituent. The demethylation reaction can be carried out by a conventional method, for example, a treatment with BBr$_3$ or HBr for the demethylation of a methoxy group, at a temperature of −78° C. to 50° C. in a suitable solvent (e.g., AcOH, water).

Procedure K: Deprotection of Protected Carboxyl Group

The compound (I) wherein Z, $Z^1$, $R^1$, $R^2$, $R^3$, $R^{41}$, $R^{42}$, $R^5$, $R^6$ or the substituent of R is carboxyl or has carboxyl can be prepared by the hydrolysis of the compound (I) wherein the corresponding Z, $Z^1$, $R^1$, $R^2$, $R^3$, $R^{41}$, $R^{42}$, $R^5$, $R^6$ or the substituent of R is C$_{1-6}$ alkoxycarboxyl group or has C$_{1-6}$ alkoxycarboxyl. The hydrolysis can be carried out by a conventional method, for example, hydrolysis using a base (e.g., NaOH, LiOH, KOH) or an acid (e.g., hydrochloric acid), and treatment with an acid (e.g., TFA), at room temperature in an organic solvent (e.g., MeOH, EtOH or THF) or without an organic solvent.

Procedure L: Alkylation of Hydroxyl Group (L-1) The compound (I) wherein Z, $Z^1$, $R^1$, $R^2$, $R^3$, $R^{41}$, $R^{42}$, $R^5$, $R^6$ or the substituent of R is a substituted or unsubstituted C$_{1-6}$ alkoxy group can be prepared by the alkylation of the compound (I) wherein the corresponding Z, $Z^1$, $R^1$, $R^2$, $R^3$, $R^{41}$, $R^{42}$, $R^5$, $R^6$ or the substituent of R is hydroxy. The alkylation reaction can be carried out using a halogenated C$_{1-6}$ alkane which may be substituted (e.g., methyl iodide, benzyl bromide) in the presence of a base (e.g., Et$_3$N, DIEA, NaHCO$_3$, KHCO$_3$, Na$_2$CO$_3$, K$_2$CO$_3$, KHCO$_3$, Cs$_2$CO$_3$) at a temperature of room temperature to 50° C. in an organic solvent (e.g., CH$_2$Cl$_2$, THF, DMF, CH$_3$CN, toluene).

The alkylation reaction can be also carried out by using a conventional alkylation method such as Mitsunobu Reaction (for reference of Mitsunobu reaction: (a) Mitsunobu, *Synthesis*, 1-28, (1981), (b) Hughes, *Organic Reactions*, 42, 335 (1992), (c) Mitsuhashi et al., *J. Am. Chem. Soc.*, 94, 26 (1972)).

(L-2) Among the compound (I) wherein B is —CH(OR$^3$)— and R$^3$ is C$_{1-6}$ alkyl which may be substituted can be prepared by the alkylation of the compound (I) wherein B is —CH(OH)—. The alkylation reaction can be carried out using a C$_{1-6}$ alkyl halide which may be substituted in the presence of a base (e.g., Et$_3$N, DIEA, NaHCO$_3$, KHCO$_3$, Na$_2$CO$_3$, K$_2$CO$_3$, KHCO$_3$, Cs$_2$CO$_3$) at a temperature of room temperature to 50° C. in an organic solvent (e.g., CH$_2$Cl$_2$, THF, DMF, CH$_3$CN, toluene). The alkylation reaction can be also carried out by a conventional alkylation method such as Mitsunobu Reaction.

Procedure M: Conversion of Carboxyl Group into Carbamoyl Group (M-1) The compound (I) wherein Z, $Z^1$, $R^1$, $R^2$, $R^3$, $R^{41}$, $R^{42}$, $R^5$, $R^6$ or the substituent of R is a substituted or unsubstituted carbamoyl group can be prepared by condensing the compound (I) wherein Z, $Z^1$, $R^1$, $R^2$, $R^3$, $R^{41}$, $R^{42}$, $R^5$, $R^6$ or the substituent of R is carboxyl with a substituted or unsubstituted amine.

The condensation reaction can be carried out by the conventional method for a usual peptide synthesis. The condensation reaction of the compound (I) with a substituted or unsubstituted amine is carried out in the presence of a condensing reagent with or without a base in a suitable solvent or without a solvent. The condensing reagent can be selected from any one which can be used for a conventional amide bond synthesis, for example, BOP—Cl, BOP reagent, DCC, EDC or CDI.

The base can be selected from an organic base (e.g., DIEA, DMAP, DBU, $Et_3N$), an alkali metal hydride (e.g., NaH, LiH), an alkali metal carbonate (e.g., $Na_2CO_3$, $K_2CO_3$), an alkali metal hydrogen carbonate (e.g., $NaHCO_3$, $KHCO_3$), an alkali metal amide (e.g., $NaNH_2$), an alkali metal alkoxide (e.g., NaOMe, KOMe), a lower alkyl alkali metal salt (e.g., n-BuLi, t-BuLi), an alkali metal hydroxide (e.g., NaOH, KOH), an alkaline earth metal hydroxide (e.g., $Ba(OH)_2$), and the like.

The solvent can be selected from any one which does not disturb the condensation reaction, for example, $CH_2Cl_2$, THF, DMF or a mixture thereof. The reaction is carried out at a temperature of 0° C. to room temperature, preferably at room temperature.

The condensation reaction of a substituted or unsubstituted amine with the reactive derivative of the compound (I), for example, with an acid halide (e.g., an acid chloride), a reactive ester (e.g., an ester with p-nitrophenol), an anhydride thereof, a mixed anhydride with other carboxylic acid (e.g., a mixed anhydride with acetic acid), and the like, is carried out in the presence of a base or without a base in a solvent or without a solvent.

The base can be selected from an organic base (e.g., DIEA, DMAP, DBU, $Et_3N$), an alkali metal hydride (e.g., NaH, LiH), an alkali metal carbonate (e.g., $Na_2CO_3$, $K_2CO_3$), an alkali metal hydrogen carbonate (e.g., $NaHCO_3$, $KHCO_3$), an alkali metal amide (e.g., $NaNH_2$), an alkali metal alkoxide (e.g., NaOMe, KOMe), a lower alkylalkali metal salt(e.g., n-BuLi, t-BuLi), an alkali metal hydroxide (e.g., NaOH, KOH), an alkaline earth metal hydroxide (e.g., $Ba(OH)_2$), and the like.

The solvent can be selected from any one which does not disturb the condensation reaction, for example, $CH_2Cl_2$, $C_2H_4Cl_2$, $Et_2O$, THF, DMF, $CH_3CN$, DMSO, benzene, toluene or a mixture thereof. The reaction is carried out at a temperature of –30° C. to 100° C.

(M-2) The compound (I) wherein Z or $Z^1$ is $COR^{42}$ and $R^{42}$ is $NR^3R^6$ can be prepared by condensing the compound (I) wherein Z or $Z^1$ is carboxyl with $HNR^3R^6$.

The condensation reaction can be carried out by a conventional method as described in (M-1).

(M-3) The compound (I) wherein R has –C(=O)—(α-amino acid residue) as a substituent thereof can be prepared by condensing the compound (I) wherein R has carboxyl group as a substituent thereof with an α-amino acid.

The condensation reaction can be carried out by a conventional method as described in (M-1).

Procedure N: Conversion of Halogen Atom to Aryl Group or Heteroaryl Group

The compound (I) wherein X and Y are aryl which may be substituted or heteroaryl which may be substituted can be prepared by reacting the compound (I) wherein X and Y is halogen with a (substituted or unsubstituted aryl)boronic acid or a (substituted or unsubstituted heteroaryl)boronic acid using a conventional aryl coupling method such as Suzuki Coupling method. The coupling reaction can be carried out in a similar procedure as described in Scheme 1.

Procedure O: Oxidation of Sulfur Atom (O-1) The compound (I) wherein B is —SO— or —$SO_2$— can be prepared by oxidizing the compound (I) wherein B is —S— with an oxidant such as a peracid (e.g., mCPBA, $H_2O_2$, AcOOH, PhCOOOH) in a suitable solvent (e.g., $CH_2Cl_2$) at room temperature or under cooling.

(O-2) The compound (I) wherein R has $C_{1-6}$ alkylsulfinyl or $C_{1-6}$ alkylsulfonyl as a substituent thereof can be prepared by oxidizing the compound (I) wherein R has $C_{1-6}$ alkylthio as a substituent. The oxidation can be carried out in a similar manner as described in the above procedure (O-1).

Procedure P: Acylation of Pyrrolyl Group (P-1) The compound (I) wherein X and/or Y is formyl-substituted pyrrolyl can be prepared by formylation of the compound (I) wherein X and/or Y is unsubstituted pyrrolyl. The formylation can be carried out by a conventional method, for example, with using a Vilsmeier reagent (DMF—$POCl_3$) in a suitable solvent (e.g., DMF) at a temperature of 0° C. to 50° C., preferably at room temperature.

(P-2) The compound (I) wherein $R^1$ is lower alkanoyl-substituted pyrrolyl (said lower alkanoyl may be substituted with halogen) can be prepared by the acylation of the compound (I) wherein $R^1$ is unsubstituted pyrrolyl. The acylation can be carried out by reacting the compound (I) with a requisite lower alkanoyl halide (e.g., acetyl chloride) or a requisite lower alkanoic acid anhydride (e.g., acetic anhydride, trifluoroacetic anhydride) in the presence or absence of a Lewis acid (e.g., $SnCl_2$, $TiCl_4$, $AlCl_3$) in a suitable solvent (e.g., $CH_2Cl_2$, $CCl_4$) at a temperature of 0° C. to 50° C., preferably at room temperature.

Procedure Q: Amination of Halogen

The compound (I) wherein X and/or Y is $NR^3R^6$ can be prepared by the amination of the compound (I) wherein X and/or Y is a halogen with an amine compound, $HNR^3R^6$. The amination can be carried out in a suitable solvent (e.g., THF, toluene, DMF) or without solvent in a sealed tube at a temperature of 50° C. to 150° C.

Procedure R: Halogenation of Oxo Group

The compound (I) wherein B is —$CF_2$— can be prepared by halogenating the compound (I) wherein B is —C(=O)—. The halogenation can be carried out with a halogenating reagent (e.g., (diethylamino)sulfur trifluoride) in a suitable solvent such as halogenomethane (e.g., $CH_2Cl_2$) at a temperature of 0° C. to 50° C., preferably at a room temperature.

Procedure S: Conversion of CN Group into Tetrazolyl Group

The compound (I) wherein R is tetrazolyl-substituted aryl or tetrazolyl-substituted heteroaryl can be prepared by reacting the compound (I) wherein R is cyano-substituted aryl or cyano-substituted heteroaryl with an alkali metal azide (e.g., $NaN_3$). The reaction can be carried out in a suitable solvent (e.g., DMF, DMSO, toluene) at a temperature of 50° C. to 150° C.

Procedure T: Conversion of CN Group into Amidino Group

The compound (I) wherein R is amidino-substituted aryl or amidino-substituted heteroaryl can be prepared by 1) alcoholyzing the compound (I) wherein R is a cyano-substituted aryl or a cyano-substituted heteroaryl, and 2) reacting the resulting ester with ammonia. The alcoholysis (step 1) can be carried out in the presence of an acid (e.g., HCl) in a suitable alcohol (e.g., MeOH, EtOH) at a temperature of 50° C. to 150° C., preferably at room temperature. The reaction of the resulting ester with ammonia (step 2) can be carried out in a suitable solvent (e.g., MeOH, EtOH) at a temperature of 50° C. to 150° C., preferably at room temperature.

Procedure U: Halogenation of Aryl or Heteroaryl

The compound (I) wherein R is halogenoaryl or halogenoheteroaryl (e.g., fluorophenyl) can be prepared by reacting the compound (I) wherein R is aryl or heteroaryl with a halogenating reagent (e.g., fluoropyridinium triflate) in a suitable solvent (e.g., $CH_3CN$) at a temperature of 0° C. to 100° C.

Procedure V: Conversion of Amino Group into Pyrrolyl Group or Dimethylpyrrolyl Group (V-1) The compound wherein B is —CH(pyrrolyl)- can be prepared by reacting the compound (I) wherein B is —CH($NH_2$)— with 2,5-dimethoxyfuran in the presence of a base (e.g., NaOAc) in a suitable solvent (e.g., acetic acid). The reaction can be carried out at a temperature of 0° C. to 100° C.

(V-2) The compound wherein B is —CH(dimethylpyrrolyl)- can be prepared by reacting the compound (I) wherein B is —CH($NH_2$)— with 2,5-hexanedione in the presence of acid (e.g., AcOH) in a suitable solvent (e.g., EtOH, AcOH)

The starting compound of the formula (II) can be prepared by the following scheme:

Scheme 7.

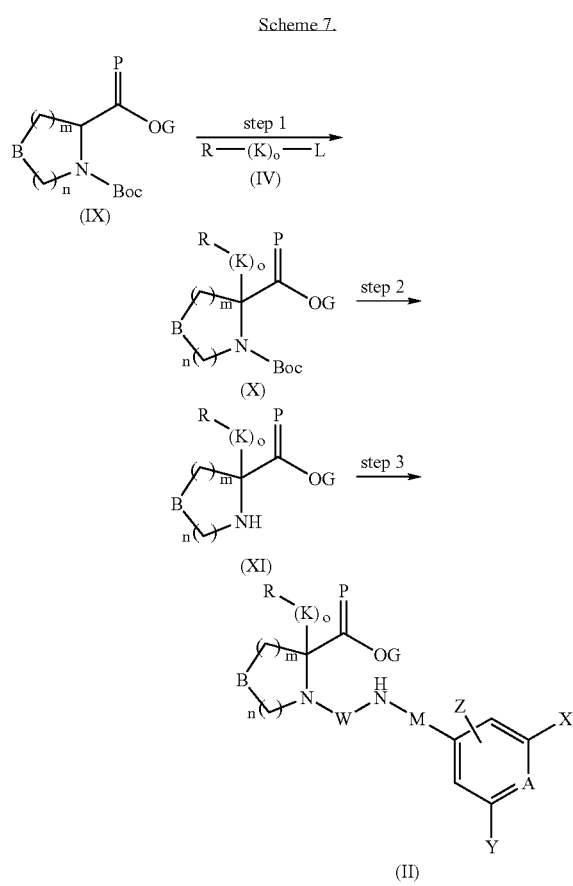

(In the Scheme 7, the symbols are the same as defined above.)

Step 1: The compound (X) can be prepared by reacting the compound (IX) with the compound (IV). The reaction can be carried out in a similar manner as described in Method B.

Step 2: The compound (XI) can be prepared by deprotecting the compound (X). The deprotection can be carried out by a usual manner used for the deprotection of a Boc protected amino group.

Step 3: The compound (II) can be prepared by reacting the compound (XI) with the compound of the formula (XII-a):

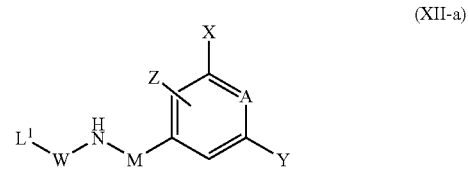

(XII-a)

wherein $L^1$ is a leaving group and the other symbols are the same as defined above, or with the compound of the formula (XII-b):

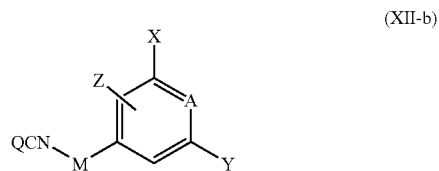

(XII-b)

wherein the symbols are the same as defined above.

The leaving group may be selected from conventional leaving groups such as halogen atoms (i.e., chlorine and bromine).

The reaction can be carried out in the presence or absence of a base in a suitable solvent or without a solvent. The base can be selected from conventional inorganic bases such as $K_2CO_3$, $Na_2CO_3$ and $NaHCO_3$, and conventional organic bases such as pyridine, $Et_3N$, $iPr_2EtN$, aniline, and N,N-dimethylaniline. The solvent can be selected from any one which does not disturb the coupling reaction, for example, toluene, DME, DMF, THF, $CH_2Cl_2$ or a mixture thereof. The coupling reaction can be carried out, for example, at a temperature of −78° C. to 50° C., preferably at a temperature of 0° C. to room temperature.

The compound (II) wherein OG is a resin-combined hydroxyl group may be also prepared in accordance with the following scheme:

Scheme 8.

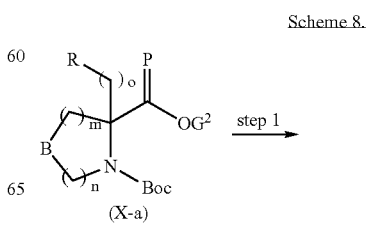

(X-a)

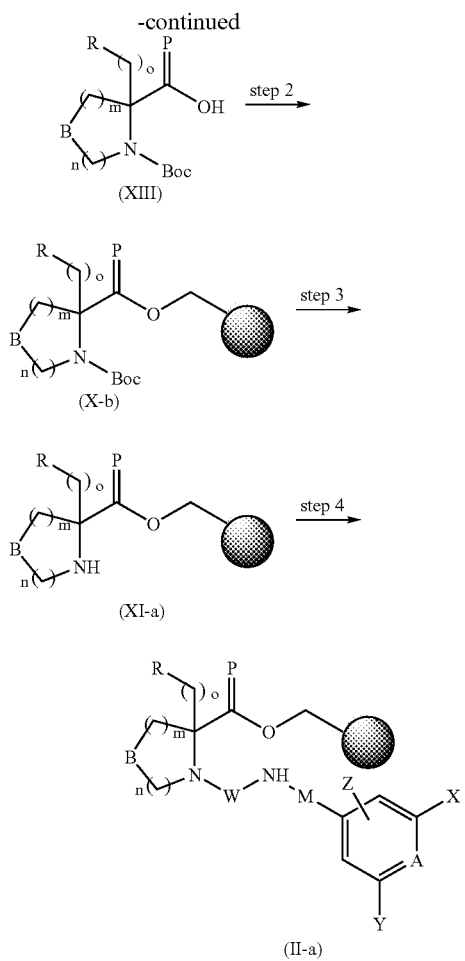

(In the Scheme 8, OG$^2$ is a protected hydroxyl group,

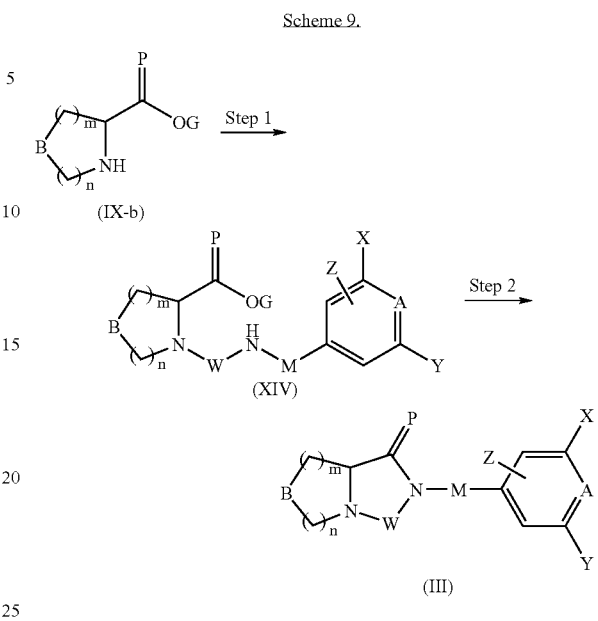

is a resin polymer and other symbols are the same as defined above.)

Step 1: The compound (XIII) can be prepared by deprotecting the compound (XI-a). The deprotection can be carried out by a usual manner used for the deprotection of a protected carboxyl group, for example, by hydrolysis.

Step 2: The reaction can be carried out by a conventional method for solid phase synthesis (e.g., Horiki's method, Horiki et al., Chem. Lett. 1978 (2) 165-168). For example, the reaction can be carried out by heating the compound thus obtained with Merrifield resin in the presence of KF in a suitable solvent such as DMF.

Step 3: The removal of Boc group can be carried out by a similar method as described in the Scheme 7, step 2.

Step 4: The reaction can be carried out by a similar method as described in the Scheme 7, step 3.

The starting compound of the formula (III) can be prepared in accordance with the following scheme:

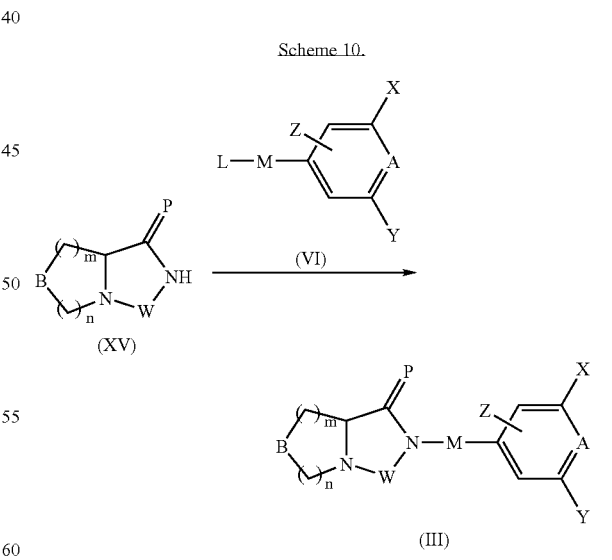

(In the Scheme 9, the symbols are the same as defined above.)

Step 1: The compound (XIV) can be prepared by reacting the compound (IX-b) with the compound (XII-a) or with the compound (XII-b). The reaction can be carried out in a similar manner as described in the scheme 6, step 3.

Step 2: The compound (III) can be prepared by cyclizing the compound (XIV). The cyclization can be carried out in a similar manner as described in Method A.

The starting compound (III) can be also prepared in accordance with the following scheme:

(In the Scheme 10, the symbols are the same as defined above.)

The compound (III) can be prepared by reacting the compound (XV) with the compound (VI). The reaction can be carried out in a similar manner as described in the Method C. The Starting compound (XV) can be prepared by a conventional method (for example, *J. Med. Chem.*, 1995, 38, 3566).

The starting compound (III) can be also prepared in accordance with the following scheme:

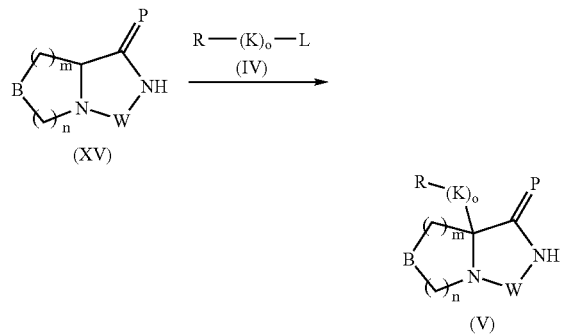

Scheme 11.

(In the Scheme 11, the symbols are the same as defined above.)

The compound (V) can be prepared by reacting the compound (XV) with the compound (IV). The reaction can be carried out in a similar manner as described in the Method B.

In the present description and the claims, the $C_{1-6}$ alkyl means a straight chain or branched chain alkyl group having 1 to 6 carbon atoms, for example, methyl, ethyl, propyl, butyl, etc., preferably one having 1 to 4 carbon atoms. The $C_{3-6}$ cycloalkyl means a cycloalkyl group having 3 to 6 carbon atoms, for example, cyclopropyl, cyclobutyl, cyclopentyl, etc. The $C_{1-6}$ alkoxy means a straight chain or branched chain alkoxy group having 1 to 6 carbon atoms, for example, methoxy, ethoxy, propoxy, butoxy, etc., preferably one having 1 to 4 carbon atoms. The $C_{1-6}$ alkoxy also includes a cycloalkyloxy group having 3 to 6 carbon atoms, for example, cyclopropyl, cyclobutyl, cyclopentyl, etc. The $C_{1-6}$ alkoxycarbonyl means a straight chain or branched chain alkoxycarbonyl group comprising an alkoxy group having 1 to 6 carbon atoms and carbonyl group, for example methoxycarbonyl, ethoxycarbonyl, propoxycarbonyl, and butoxycarbonyl, etc., preferably one having 1 to 4 carbon atoms.

The $C_{1-7}$ alkanoyl means a straight chain or branched chain alkanoyl group having 1 to 7 carbon atoms, for example, formyl, acetyl, propionyl, butyryl, etc., preferably one having 1 to 5 carbon atoms. The $C_{2-7}$ alkenyl means a straight chain or branched chain alkenyl group having 2 to 7 carbon atoms, for example vinyl, allyl, crotyl, etc., preferably one having 2 to 5 carbon atoms. The "α-amino acid residue" means an amino acid residue which is obtained by removing a hydrogen atom from the amino group of the corresponding α-amino acid (e.g., aspartic acid, glutamic acid, glutamine, serine, sarcosine, proline, phenylalanine, leucine, glycine, tryptophan, cysteine, histidine, tyrosine, and valine).

ABBREVIATIONS

Ac: Acetyl
Ac₂O: Acetic anhydride
AcOH: Acetic acid
ACOOH: Peracetic acid
AcOEt: Ethyl acetate (=EtOAc)
BOC: t-Butoxycarbonyl (=t-Boc)
BOP—Cl: Bis(2-oxo-3-oxazolidinyl)phosphinic chloride
BOP Reagent: Benzotriazol-1-yloxy-tris(dimethylamino)-phosphonium hexafluorophosphate
BSA: Bovine serum albumin
CDI: 1,1'-Carbonyldiimidazole
DAST: Diethylaminosulfur trifluoride
DCC: 1,3-Dicyclohexylcarbodiimide
DCM: Dichloromethane
DEAD: Diethyl azodicarboxylate
DME: Dimethoxyethane
DMAP: 4-Dimethylaminopyridine
DMF: Dimethyl formamide
DIEA: Diisopropylethylamine
DMSO: Dimethyl sulfoxide
EDC: 1-(3-Dimethylaminopropyl)-3-ethylcarbodiimide hydrochloride
Et: Ethyl
EtOH: Ethanol
HBSS: Hank's balanced salt solution
HBTU: O-Benzotriazol-1-yl-N,N,N',N'-tetramethyluronium hexafluorophosphate
HMPA: Hexamethylphosphoramide
HOBT: 1-Hydroxybenzotriazole
HSA: Human serum albumin
KHMDS: Potassium hexamethyldisilazide (=Potassium bis(trimethylsilyl)amide)
LDA: Lithium diisopropylamide
mCPBA: m-Chloroperbenzoic acid (=MCPBA)
Me: Methyl
MeOH: Methanol
n-Bu: n-Butyl
PBS: Phosphate buffered saline
PCC: Pyridinium dichromate
PDC: Pyridinium chlorochromate
Ph: Phenyl
i-Pr: i-Propyl
t-Bu: tert-Butyl
THF: Tetrahydrofuran
Tf: Trifluoromethanesulfonyl
TFA: Trifluoroacetic acid
TBDMS: tert-Butyl-dimethylsilyl
Tris: Tris(hydroxymethyl)aminomethane The compound of the present invention is exemplified by the following examples but not limited thereby.

EXAMPLES

Example 1

5-(4-Bromobenzyl)-3-(3,5-dichlorophenyl)-1,3-diazabicyclo[3.3.0]octane-2,4-dione (1) To a solution of N-(tert-butoxycarbonyl)proline methyl ester (1.30 g) in THF (20 mL) at −78° C. was added a solution of KHMDS (1.25 g) in THF (20 mL). After 45 minutes, a solution of 4-bromobenzyl bromide (1.59 g) in THF (20 mL) was added at −78° C. The reaction mixture was warmed to room temperature over 3 hours and stirred for an additional 3 hours. The mixture was diluted with EtOAc, washed with water and brine, dried (Na₂SO₄), filtered and concentrated. Purification by flash column chromatography (silica gel; EtOAc/hexane 1:2) afforded N-(tert-butoxycarbonyl)-2-(4-bromobenzyl)proline methyl ester (0.474 g). MS (m/z) 398 (MH⁺).

(2) To a solution of the compound obtained above (0.474 g) in CH$_2$Cl$_2$ (5 mL) was added TFA (1.5 mL). After 1 hour, the reaction mixture was diluted with CH$_2$Cl$_2$, washed with aqueous NaHCO$_3$ and brine, dried (Na$_2$SO$_4$) and concentrated to give 2-(4-bromobenzyl)proline methyl ester. MS (m/z) 298 (MH$^+$).

(3) 3,5-Dichlorophenylisocyanate (0.50 g) was added to a solution of the compound obtained above in THF (10 mL) and DIEA (2.0 mL). After 4 hours stirring at room temperature, the reaction mixture was concentrated. The residue was redissolved in EtOAc, washed with aqueous NaHCO$_3$ and brine, dried (Na$_2$SO$_4$), filtered and concentrated. Purification by chromatography (silica gel: EtOAc/hexane: 1/4, Chromatotron (Harrison Research)) afforded 0.33 g of N-[(3,5-dichlorophenyl)carbamoyl]-2-(4-bromobenzyl)proline methyl ester. MS (m/z) 485 (MH$^+$). mp 170.9° C.

(4) The compound obtained above (0.153 g) was dissolved in hot EtOH (10 mL) and cooled to 0° C. To the solution at 0° C. was added NaOEt (0.010 g). After 45 minutes of stirring, the mixture was concentrated. Purification by chromatography (silica gel: 15% EtOAc/hexane, Chromatotron) afforded the titled compound (0.129 g). MS (m/z) 453 (MH$^+$). mp 69.4° C.

Example 2

(5S, 7R)-5-(4-Bromobenzyl)-3-(3,5-dichlorophenyl)-7-hydroxy-1,3-diazabicyclo[3.3.0]octane-2,4-dione (1) To a solution of (4R)-N-(tert-Butoxycarbonyl)-4-hydroxy proline benzyl ester (Williams et al., *J. Org. Chem.* 1994, 59, 3612-3625) (20.75 g) in acetonitrile (200 mL) was added imidazole (4.43 g) and tert-butyldimethylsilylchloride (14.47 g). After stirring overnight, the reaction was concentrated. The residue was redissolved in EtOAc, washed with satd. NaHCO$_3$ and brine, dried (Na$_2$SO$_4$), filtered and concentrated. The compound thus obtained, (4R)-N-(tert-Butoxycarbonyl)-4-(tert-butyldimethylsilyl-oxy)propline benzyl ester (5.60 g), was treated in a similar manner as described in Example 1 (1) to give (2S, 4R)-N-(tert-butoxycarbonyl)-2-(4-bromobenzyl)-4-(tert-butyldimethylsilyl-oxy)proline benzyl ester (4.26 g).

(2) To a solution of the compound obtained above (1.00 g) in CH$_2$Cl$_2$ (20 mL) was added TBDMSOTf (0.58 mL). After 15 minutes, the mixture was diluted with CH$_2$Cl$_2$, washed with water and brine, dried (Na$_2$SO$_4$), filtered and concentrated to yield 0.85 g of 2-(4-bromobenzyl)-4-(tert-butyldiimethylsilyloxy)proline benzyl ester as a mixture of diastereoisomers. MS (m/z) 504 (MH$^+$).

(3) The compound obtained above (0.38 g) was treated in a similar procedure as described in Example 1 (3) and (4) to give (5S,7R)-5-(4-bromobenzyl)-3-(3,5-dichlorophenyl)-7-(tert-butyldimethylsilyloxy)-1,3-diazabicyclo-[3.3.0]octane-2,4-dione. Separation of the diastereoisomers (5S,7R; 0.23 g) and (5R,7R; 0.045 g) was achieved via flash chromatography eluting with CH$_2$Cl$_2$.

(4) To a solution of the compound obtained above (5S,7R; 1.75 g) in THF (20 mL) was added HF-pyridine (65-70%, 2.00 mL). After stirring overnight, additional HF-pyridine (65-70%, 1.00 mL) was added. After 20 hours, the mixture was concentrated. The residue was dissolved in EtOAc, washed with 0.5 N HCl, satd. NaHCO$_3$ and brine, dried (Na$_2$SO$_4$), filtered and concentrated to give 1.43 g of the titled compound. MS (m/z) 469 (MH$^+$). mp 136.1° C.

Example 3

(5S,7S)-5-(4-Bromobenzyl)-3-(3,5-dichlorophenyl)-7-azido-1,3-diazabicyclo[3.3.0]octane-2,4-dione (1) To a solution of (5S,7R)-5-(4-bromobenzyl)-3-(3,5-dichloro-phenyl)-7-hydroxy-1,3-diazabicyclo[3.3.0]octane-2,4-dione (0.81 g) in CH$_2$Cl$_2$ (5 mL) and DIEA (0.50 mL) at 0° C. was added methanesulfonyl chloride (0.19 mL). After 1 hour at 0° C., the mixture was diluted with CH$_2$Cl$_2$, washed with satd. NaHCO$_3$ and brine, dried (Na$_2$SO$_4$) and concentrated to give (5S, 7R)-5-(4-bromobenzyl)-3-(3,5-dichlorophenyl)-7-methylsulfonyloxy-1,3-diazabicyclo[3.3.0]octane-2,4-dione. MS (m/z) 494 (MH$^+$).

(2) To a solution of the compound obtained above in DMF (4 mL) at 75° C. was added sodium azide (0.54 g). After heating for 2 hours the mixture was diluted with Et$_2$O and water. The organic solution was collected, washed with water and brine, dried (Na$_2$SO$_4$), filtered and concentrated. Purification by chromatography (silica gel: 2% methanol/CH$_2$Cl$_2$, Chromatotron) afforded the titled compound (0.82 g). MS (m/z) 494 (MH$^+$), mp 58.9° C.

Example 4

(5S,7S)-5-(4-Bromobenzyl)-3-(3,5-dichlorophenyl)-7-acetoxy-1,3-diazabicyclo[3.3.0]octane-2,4-dione To a solution of (5S,7R)-5-(4-bromobenzyl)-3-(3,5-dichlorophenyl)-7-hydroxy-1,3-diazabicyclo[3.3.0]octane-2,4-dione (0.21 g) in THF (5 mL) was added DEAD (0.09 mL), triphenylphosphine (0.15 g), and acetic acid (0.035 mL). After stirring overnight at room temperature, the mixture was concentrated. Purification by chromatography (Silica gel: 25% EtOAc/hexane, Chromatotron) afforded the titled compound (0.151 g). MS (m/z) 511 (MH$^+$), mp 149.8° C.

Example 5

(5S,7S)-5-(4-Bromobenzyl)-3-(3,5-dichlorophenyl)-7-hydroxy-1,3-diazabicyclo[3.3.0]octane-2,4-dione To a solution of (5S,7S)-5-(4-bromobenzyl)-3-(3,5-dichloro-phenyl)-7-acetoxy-1,3-diazabicyclo[3.3.0]octane-2,4-dione (0.10 g) in THF (5 mL), MeOH (0.10 mL), and water (0.10 mL) was added 2N LIOH (0.11 mL). After 4 hours, the mixture was quenched with acetic acid (0.10 mL) and concentrated. Purification by chromatography (Silica gel: 4% methanol/CH$_2$Cl$_2$, Chromatotron) afforded the titled compound (0.0435 g). MS (m/z) 469 (MH$^+$), mp 88.3° C.

Example 6

6-(4-Bromobenzyl)-8-(3,5-dichlorophenyl)-1,8-diazabicyclo[4.3.0]nonane-7,9-dione The titled compound was prepared by a similar procedure as described in Example 1 starting from pipecolinic acid except that cyclization occurred during treatment with 3,5-dichlorophenyl isocyanate and DIEA. MS (m/z) 467 (MH$^+$). mp 128.8° C.

Example 7

6-[4-(3-Pyridyl)benzyl]-8-(3,5-dichlorophenyl)-1,8-diazabicyclo[4.3.0]nonane-7,9-dione To a solution of 6-(4-bromobenzyl)-8-(3,5-dichlorophenyl)-1,8-diazabicyclo[4.3.0]nonane-7,9-dione (0.360 g) and 3-pyridineboronic acid (0.225 g) in DME (20 mL) was added CsF (0.615 g) and the mixture was degassed with nitrogen. After 10 minutes, Pd(PPh$_3$)$_4$ was added and the mixture was heated under reflux for 6 hours. The reaction mixture was concentrated. The residue was redissolved in EtOAc, washed with water and brine, dried (Na$_2$SO$_4$), filtered, and concentrated. Purification by chromatography (Silica gel: hexane/acetone: 3/2, Chromatotron) afforded the titled compound (0.172 g). MS (m/z) 466 (MH$^+$). mp 276.5° C.

The following compounds (Examples 8-11) were prepared in a fashion similar to Example 7 by replacing 3-pyridineboronic acid with requisite boronic acids.

TABLE 1

| Example | R | n | Physicochemical data |
|---|---|---|---|
| 8 | 2-CHO-phenyl-methyl | 2 | MS (m/z) 493 (MH$^+$) Mp. 154° C. |
| 9 | 3-CHO-furan-2-yl | 1 | MS (m/z) 469 (MH$^+$) |
| 10 | 3-CHO-thiophen-2-yl | 1 | MS (m/z) 485 (MH$^+$), 507 (M + Na$^+$) |
| 11 | 3-CHO-1-(COO-t-Bu)-pyrrol-2-yl | 1 | MS (m/z) 540 (MH$^+$) |

Example 12

6-[4-[2-(Hydroxymethyl)phenyl]benzyl]-8-(3,5-dichlorophenyl)-1,8-diazabicyclo[4.3.0]nonane-7,9-dione NaBH$_4$ (13.7 mg) was added to a solution of 6-[4-(2-formyl-phenyl)benzyl]-8-(3,5-dichlorophenyl)-1,8-diazabicyclo[4.3.0]-nonane-7,9-dione (0.178 mg) in THF (5 mL) at 0° C. After stirring for 30 minutes, the reaction mixture was diluted with water and extracted with EtOAc. The extract was washed with brine, dried (Na$_2$SO$_4$), filtered, and concentrated. Purification by chromatography (Silica gel: EtOAc/hexane: 1/2, Chromatotron) afforded the titled compound (167 mg). MS (m/z) 477 (M$^+$–OH).

Example 13

6-[4-[2-(N,N-Dimethylaminomethyl)phenyl]benzyl]-8-(3,5-dichlorophenyl)-1,8-diazabicyclo[4.3.0]nonane-7,9-dione SOCl$_2$ (0.15 mL) was added to a solution of 6-[4-[2-(hydroxymethyl)phenyl]benzyl]-8-(3,5-dichlorophenyl)-1,8-diazabicyclo[4.3.0]nonane-7,9-dione (0.121 g) in CH$_2$Cl$_2$ (5 mL). The mixture was stirred for 1 hour and then evaporated. The residue was dissolved in toluene, evaporated and dried under vacuum. The residue was dissolved in DMF (4 mL) and the solution was added to an ice cold solution of dimethylamine (1 mL, 2M in THF) in DMF. The reaction mixture was stirred for 18 hours at room temperature and diluted with EtOAc. Aqueous NaHCO$_3$ was added and the organic layer was separated. The extract was washed with water, brine, dried (MgSO$_4$), filtered, and concentrated. Purification by chromatography (Silica gel: CHCl$_3$/MeOH: 50/1 to 20/1, Chromatotron) afforded the titled compound (70 mg). It was converted to the HCl salt. MS(m/z) 522 (MH$^+$).

Example 14

6-[4-(2-Methoxycarbonylphenyl)benzyl]-8-(3,5-dichlorophenyl)-1,8-diazabicyclo[4.3.0]nonane-7,9-dione To a solution of 6-[4-(2-formylphenyl)benzyl]-8-(3,5-dichlorophenyl)-1,8-diazabicyclo[4.3.0]nonane-7,9-dione (0.206 g) in MeOH (20 mL) was added NaCN (0.204 g), ACOH (0.086 mL) and MnO$_2$ (activated, 1.84 g) and the mixture was stirred overnight at room temperature. The inorganics were removed by filtration through Celite and the filtrate was evaporated. The residue was dissolved in EtOAc and washed with water, brine, dried (MgSO$_4$), filtered, and concentrated. Purification by chromatography (Silica gel: EtOAc/hexane: 1/2) afforded the titled compound (0.161 g). It was converted to the HCl salt. MS (m/z) 545 (M$^{30}$ +Na), 523 (MH$^+$)

Example 15

6-[4-(2-Carboxyphenyl)benzyl]-8-(3,5-dichlorophenyl)-1,8-diazabicyclo[4.3.0]nonane-7,9-dione A solution of 6-[4-(2-methoxycarbonylphenyl)benzyl]-8-(3,5-dichlorophenyl)-1,8-diazabicyclo[4.3.0]nonane-7,9-dione (0.141 g) in MeOH/H$_2$O (5/1 mL) containing NaOH (0.087 g) was heated at 50° C. for 2 h. The reaction mixture was cooled in ice and acidified with 0.5 N HCl. It was extracted with EtOAc and the extract was washed with water, brine, dried (MgSO$_4$), filtered, and concentrated. Purification by chromatography (Silica gel: CHCl$_3$/MeOH: 100/1 to 50/1, Chromatotron) afforded the titled compound (114 mg). MS (m/z) 531 (M$^+$+Na).

Example 16

6-[4-[2-(N,N-Dimethylcarbamoyl)phenyl]benzyl]-8-(3,5-dichlorophenyl)-1,8-diazabicyclo[4.3.0]nonane-7,9-dione A mixture of the 6-[4-(2-carboxyphenyl)benzyl]-8-(3,5-dichlorophenyl)-1,8-diazabicyclo[4.3.0]nonane-7,9-dione (0.089 g) and SOCl$_2$ (1.0 mL) was heated at 100° C. for 1 hour. The solution was evaporated. The residue was dissolved in toluene, evaporated and dried under vacuum. The residue was dissolved in THF (4 mL) and the solution was added to an ice cold solution of dimethylamine (1 mL, 2M in THF) in THF (1 mL). The reaction mixture was stirred for 3 hours at room temperature and diluted with EtOAc and water. The organic layer was separated and washed with 0.5 N HCl (10 mL), water and brine. It was dried (MgSO$_4$), filtered, and concentrated. Purification by chromatography (Silica gel: EtOAc/hexane: 1/2 to 1/1, Chromatotron) afforded the titled compound (85 mg). MS (m/z) 536(MH$^+$).

Example 17

6-[4-[2-(2-Methoxycarbonylvinyl)phenyl]benzyl]-8-(3,5-dichlorophenyl)-1,8-diazabicyclo[4.3.0]nonane-7,9-dione A mixture of 6-[4-(2-formylphenyl)benzyl]-8-(3,5-dichloro-phenyl)-1,8-diazabicyclo[4.3.0]nonane-7,9-dione (0.205 g) and methyl (triphenylphosphoranylidene)acetate (0.223 g) in toluene (5 mL) was refluxed for 8 hours. The mixture was evaporated and the residue was purified by chromatography (Silica gel: EtOAc/hexane: 1/4 to 1/3, Chromatotron) to afford the titled compound (0.229 g). MS (m/z) 571(M$^+$+Na).

Example 18

6-[4-[2-(2-Methoxycarbonylethyl)phenyl]benzyl]-8-(3,5-dichlorophenyl)-1,8-diazabicyclo[4.3.0]nonane-7,9-dione NiCl$_2$. 6H$_2$O (0.17 g) was added to a solution of 6-[4-[2-(2-methoxycarbonylvinyl)phenyl]benzyl]-8-(3,5-dichlorophenyl)-1,8-diazabicyclo[4.3.0]nonane-7,9-dione (0.196 g). NaBH$_4$ (0.14 g) was added portionwise to the mixture and the mixture was stirred for 1 hour. The mixture was diluted with EtOAc and water and filtered through Celite. The organic layer was separated and washed with water, brine, dried (MgSO$_4$), filtered, and concentrated. Purification by chromatography (Silica gel: EtOAc/hexane: 1/4, Chromatotron) afforded the titled compound (0.125 g). MS (m/z) 573 (M$^+$+Na).

Example 19

6-[4-[2-(2-Carboxyethyl)phenyl]benzyl]-8-(3,5-dichlorophenyl)-1,8-diazabicyclo[4.3.0]nonane-7,9-dione An aqueous solution of NaOH (2 mL; 0.5 N) was added to a solution of 6-[4-[2-(2-methoxycarbonylethyl)phenyl]benzyl]-8-(3,5-dichlorophenyl)-1,8-diazabicyclo[4.3.0]nonane-7,9-dione (0.11 g) in MeOH (7 mL) and the mixture was stirred for 18 hours. The reaction mixture was acidified, diluted with water and extracted with EtOAc. The extract was washed with water, brine, dried (MgSO$_4$), filtered, and concentrated to give the titled compound (0.109 g). MS (m/z) 559 (M$^+$+Na).

Example 20

6-[4-[2-[2-(N,N-Dimethylcarbamoyl)ethyl]phenyl]-benzyl]-8-(3,5-dichlorophenyl)-1,8-diazabicyclo[4.3.0]nonane-7,9-dione The titled compound was prepared in a manner similar to Example 16. MS (m/z) 564 (MH$^+$).

Example 21

5-(4-Cyanobenzyl)-3-(3,5-dichlorophenyl)-1,3-diazabicyclo[3.3.0]octane-2,4-dione (1) Et$_3$N (1.7 mL) was added to an ice-cold solution of (S)-proline methyl ester hydrochloride (1.31 g) and 3,5-dichlorophenylisocyanate (1.97 g) in CH$_2$Cl$_2$ (40 mL). The mixture was stirred for 3 hours. It was washed with water, brine, dried (MgSO$_4$), filtered, and concentrated. Purification by chromatography (Silica gel: EtOAc/hexane: 1/3) afforded (S)—N—[N-(3,5-dichlorophenyl)carbamoyl]proline methyl ester (2.27 g). mp. 110-112° C.; MS (m/z) 339 (M$^+$+Na).

(2) A solution of the compound obtained above (14.3 g) in toluene (100 mL) containing p-toluenesulfonic acid (0.5 g) was refluxed for 2 hours. The solution was diluted with EtOAc and was washed with satd. NaHCO$_3$, water, brine, dried (MgSO$_4$), filtered, and concentrated. Purification by chromatography (Silica gel: CHCL$_3$/MeOH: 10/1) and recrystallization from EtOH afforded 8.87 g of (S)-3-(3,5-dichlorophenyl)-1,3-diazabicyclo[3.3.0]octane-2,4-dione. mp. 169° C.; MS (m/z) 307 (M$^+$+Na).

(3) A solution of n-BuLi (2.2 mL) in hexane (1.6 N) was added to a solution of diisopropylamine (0.381 g) in THF (5 mL) at −78° C. After 15 minutes, a solution of the compound obtained above (0.894 g) in THF (8 mL) was added to the mixture. HMPA (8 mL) and additional THF (8 mL) were added to the mixture. After 35 minutes, a solution of 4-(bromomethyl)benzonitrile (0.697 g) in THF (8 mL) was added and the mixture stirred for 30 minutes at that temperature. The mixture was slowly warmed to room temperature, stirred for 30 minutes and finally quenched with 0.5 N HCl (10 mL). The mixture was diluted with water and extracted with EtOAc. The extract was washed with water, brine, dried (Na$_2$SO$_4$), filtered, and concentrated. Purification by chromatography (Silica gel: EtOAc/hexane: 1/2, Chromatotron) afforded the titled compound (0.833 g). MS (m/z) 422 (M$^+$+Na).

Example 22

5-(4-Methoxycarbonylbenzyl)-3-(3,5-dichlorophenyl)-1,3-diazabicyclo[3.3.0]octane-2,4-dione The titled compound was prepared in a fashion similar to Example 21. MS (m/z) 455 (M$^+$+Na).

Example 23

5-[4-(N,N-Dimethylcarbamoyl)benzyl]-3-(3,5-dichlorophenyl)-1,3-diazabicyclo[3.3.0]octane-2,4-dione (1) NaOH (0.406 g) was added to a solution of 5-(4-methoxycarbonylbenzyl)-3-(3,5-dichlorophenyl)-1,3-diazabicyclo[3.3.0]octane-2,4-dione (0.601 g) in MeOH/H$_2$O (20 mL/4 mL) and the mixture was heated at 45° C. for 18 hours. The reaction mixture was cooled, acidified, diluted with water and extracted with EtOAc. The extract was washed with water, brine, dried (MgSO$_4$), filtered, and concentrated. The residue was recrystallized from EtOAc/hexane (1:1) to give N-[N-(3,5-dichlorophenyl)carbamoyl]-2-(4-carboxybenzyl)proline (0.529 g). mp. 144.6° C.; MS (m/z) 459 (M$^+$+Na).

(2) A mixture of the compound obtained above (0.074 g) and $SOCl_2$ (1.0 mL) was heated at 100° C. for 1 hour. The solution was evaporated. The residue was dissolved in toluene, evaporated and dried under vacuum. The residue was dissolved in THF (4 mL) and the solution was added to an ice cold solution of dimethylamine (1 mL, 2M in THF) in THF (1 mL). The reaction mixture was stirred for 3 hour at room temperature and diluted with EtOAc and water. The organic layer was separated and washed with 0.5 N HCl (10 mL), water and brine. It was dried ($MgSO_4$), filtered, and concentrated. Purification by chromatography (Silica gel: EtOAc, Chromatotron) afforded the titled compound (47 mg). MS (m/z) 468 ($M^+$+Na).

Example 24

5-(4-Carboxybenzyl)-3-(3,5-dichlorophenyl)-1,3-diazabicyclo[3.3.0]octane-2,4-dione A mixture of N-[N-(3,5-dichlorophenyl)carbamoyl]-2-(4-carboxybenzyl)proline (0.080 g) and $SOCl_2$ (2.0 mL) was heated at 100° C. for 1 hour. The solution was evaporated. The residue was dissolved in toluene, evaporated and dried under vacuum. The residue was dissolved in a mixture of $THF/H_2O$ (4/0.4 mL) and the solution was stirred for 18 hours. It was diluted with EtOAc and water. The organic layer was separated, washed with water, brine, dried ($MgSO_4$), filtered, and concentrated. Purification by chromatography (Silica gel: EtOAc/hexane: 1/1) afforded the titled compound (48 mg). MS (m/z) 441 ($M^+$+Na).

Example 25

5-[4-[N-(2-Hydroxyethyl)carbamoyl]benzyl]-3-(3,5-dichlorophenyl)-1,3-diazabicyclo[3.3.0]octane-2,4-dione The titled compound was prepared in a fashion similar to Example 23 but replacing dimethyl amine with 2-aminoethanol. MS (m/z) 484 ($M^+$+Na).

Example 26

4-(tert-Butoxycarbonyl)-6-(4-bromobenzyl)-8-(3,5-dichlorophenyl)-1,4,8-triazabicyclo[4.3.0]nonane-7,9-dione (1) To a solution of ethyl 1-benzyloxycarbonyl-4-(tert-butoxycarbonyl)-2-piperazinecarboxylate (2.49 g) (Tet. Lett. 30(39), 5193-5196) in EtOH was added Pd/C (0.25 g). The solution was degassed with nitrogen and hydrogen gas was bubbled into the mixture. The reaction mixture was stirred for 3 hours under hydrogen atmosphere. The mixture was filtered through Celite and concentrated to give 1.15 g of ethyl 4-(tert-butoxycarbonyl)-2-piperazinecarboxylate.

(2) To a solution of the compound obtained above in THF (10 mL) was added 3,5-dichlorophenyl isocyanate (1.00 g). After stirring overnight, the solution was concentrated. Purification by chromatography (Silica gel: EtOAc/hexane: 1/4, Chromatotron) afforded ethyl 1-[N-(3,5-dichlorophenyl)carbamoyl]-4-tert-butoxycarbonyl-2-piperazinecarboxylate (1.36 g). MS (m/z) 446 ($MH^+$).

(3) The compound obtained above was treated in a manner similar to Example 1 (4) to yield 4-(tert-butoxycarbonyl)-8-(3,5-dichlorophenyl)-1,4,8-triazabicyclo[4.3.0]nonane-7,9-dione (0.72 g). MS (m/z) 422 ($M^+$+Na) mp 60.2° C.

(4) To a solution of the compound obtained above (0.67 g) in THF (5 mL) at –78° C. was added LDA (1.3 eq.). After 30 minutes at –78° C., a solution of 4-bromobenzyl bromide (0.57 g) in THF (2 mL) was added to the mixture. The reaction mixture was allowed to warm to room temperature over 1 hour. After stirring for 4 hours the mixture was concentrated. The residue was redissolved in EtOAc, washed with 1N HCl, aqueous $NaHCO_3$, and brine, dried ($Na_2SO_4$), filtered, and concentrated. Purification by chromatography (Silica gel: EtOAc/hexane: 1/4, Chromatotron) afforded the title compound (0.89 g). MS (m/z) 590 ($M^+$+Na). mp 79.5° C.

Example 27

6-(4-Bromobenzyl)-8-(3,5-dichlorophenyl)-1,4,8-triazabicyclo[4.3.0]nonane-7,9-dione To a solution of 4-(tert-butoxycarbonyl)-6-(4-bromobenzyl)-8-(3,5-dichlorophenyl)-1,4,8-triazabicyclo[4.3.0]nonane-7,9-dione (0.82 g) in $CH_2Cl_2$ (10 mL) was added TFA (0.5 mL). Additional TFA (0.5 mL) was added after 1 hour and 2.5 hours. After 5 hours, the reaction mixture was diluted with $CH_2Cl_2$, washed with aqueous $NaHCO_3$, and brine, dried ($Na_2SO_4$), filtered, and concentrated to yield the titled compound (0.63 g). MS (m/z) 468 ($MH^+$). mp 92.5° C.

Example 28

4-Acetyl-6-(4-bromobenzyl)-8-(3,5-dichloro-phenyl)-1,4,8-triazabicyclo[4.3.0]nonane-7,9-dione To a solution of 6-(4-bromobenzyl)-8-(3,5-dichlorophenyl)-1,4,8-triazabicyclo[4.3.0]nonane-7,9-dione (0.062 g) in THF (2.5 mL) and DIEA (0.030 mL) was added acetyl chloride (0.015 mL). After 30 minutes, the reaction mixture was diluted with EtOAc and the solution washed with $NaHCO_3$, and brine, dried ($Na_2SO_4$), filtered, and concentrated. Purification by chromatography (Silica gel: $CH_2Cl_2$/MeOH: 99/1, Chromatotron) afforded the titled compound (0.046 g,). MS (m/z) 510 ($MH^+$). mp 89.6° C.

Example 29

4-Methyl-6-(4-bromobenzyl)-8-(3,5-dichloro-phenyl)-1,4,8-triazabicyclo[4.3.0]nonane-7,9-dione To a solution of 6-(4-bromobenzyl)-8-(3,5-dichlorophenyl)-1,4,8-triazabicyclo[4.3.0]nonane-7,9-dione (0.072 g) in formic acid (0.40 mL) and water (0.10 mL) was added 37% formaldehyde (0.050 mL). After 1 hour at reflux, the reaction mixture was diluted with EtOAc and the solution washed with aqueous $NaHCO_3$, and brine, dried ($Na_2SO_4$), filtered, and concentrated to yield the titled compound (74.3 g). MS (m/z) 482 ($MH^+$). mp 221° C.

Example 30

4-(tert-Butoxycarbonylmethyl)-6-(4-bromobenzyl)-8-(3,5-dichlorophenyl)-1,4,8-triazabicyclo[4.3.0]nonane-7,9-dione To a solution of 6-(4-bromobenzyl)-8-(3,5-dichlorophenyl)-1,4,8-triazabicyclo[4.3.0]nonane-7,9-dione (0.11 g) in THF (5 mL) was added DIEA (0.1 mL) and tert-butyl bromoacetate (0.06 mL). Additional tert-butyl bromoacetate (0.040 mL) was added after 16 hours. After 40 hours, the reaction mixture was concentrated and the residue was diluted with EtOAc and washed with water, NaHCO$_3$, and brine, dried (Na$_2$SO$_4$), filtered, and concentrated. Purification by chromatography (Silica gel: EtOAc/hexane: 1/5, Chromatotron) afforded the titled compound (0.124 g). MS (m/z) 582 (MH$^+$). mp 74.7° C.

Example 31

4-[(Dimethylamino)acetyl]-6-(4-bromobenzyl)-8-(3,5-dichlorophenyl)-1,4,8-triazabicyclo[4.3.0]nonane-7,9-dione To a solution of 6-(4-bromobenzyl)-8-(3,5-dichlorophenyhl)-1,4,8-triazabicyclo[4.3.0]nonane-7,9-dione (0.085 g) in THF (5 mL) was added DIEA (0.1 mL), HOBt (0.57 g), EDC (0.054 g) and N,N-dimethylglycine (0.037 g). After stirring overnight, the reaction was concentrated and the residue was diluted with EtOAc and washed with water, NaHCO$_3$, and brine, dried (Na$_2$SO$_4$), filtered, and concentrated. Purification by chromatography (Silica gel: 2% MeOH/CH$_2$Cl$_2$, Chromatotron) afforded the titled compound. (0.093 g). MS (m/z) 553 (MH$^+$). mp 73.5° C.

Example 32

4-[2-(Diethylamino)ethyl]-6-(4-bromobenzyl)-8-(3,5-dichlorophenyl)-1,4,8-triazabicyclo[4.3.0]nonane-7,9-dione The titled compound was prepared in a fashion similar to Example 30.

HCl salt: MS (m/z) 567 (MH$^+$), mp 223° C.

Example 33

4-Methanesulfonyl-6-(4-bromobenzyl)-8-(3,5-dichlorophenyl)-1,4,8-triazabicyclo[4.3.0]nonane-7,9-dione To a solution of 6-(4-bromobenzyl)-8-(3,5-dichlorophenyl)-1,4,8-triazabicyclo[4.3.0]nonane-7,9-dione (0.063 g) in CH$_2$Cl$_2$ (6 mL) was added DIEA (0.05 mL) and methanesulfonyl chloride (0.015 mL). After 1 hour, the mixture was concentrated and purified by chromatography (Silica gel: 4% MeOH/CH$_2$Cl$_2$, Chromatotron) afforded the titled compound. (0.069 g). MS (m/z) 546 (MH+). mp 229° C.

Example 34

4-Carboxymethyl-6-(4-bromobenzyl)-8-(3,5-dichlorophenyl)-1,4,8-triazabicyclo[4.3.0]nonane-7,9-dione To a solution of 4-(tert-butoxycarbonylmethyl)-6-(4-bromobenzyl)-8-(3,5-dichlorophenyl)-1,4,8-triazabicyclo[4.3.0]nonane-7,9-dione (0.080 g) in CH$_2$Cl$_2$ (10 mL) was added TFA (0.10 mL). Additional TFA (0.5 mL) was added after 3 and 22 hours. After stirring for 48 hours, the mixture was concentrated and purified by chromatography (Silica gel: 8% MeOH/CH$_2$Cl$_2$, Chromatotron) afforded the titled compound. (0.083 g). MS (m/z) 526 (MH$^+$). mp 236.5° C.

Example 35

5-(4-Bromobenzyl)-3-(3,5-dichlorophenyl)-1,3-diazabicyclo[3.3.0]octane-2,4,7-trione (1) To a solution of 1-benzyloxycarbonyl-4-oxoproline (10.61 g, J. Am. Chem. Soc., 79, 185 (1957)) in methanol (150 mL) was bubbled HCl gas. After 30 minutes, the reaction mixture was concentrated and the residue was diluted with EtOAc and washed with aqueous NaHCO$_3$ and brine, dried (Na$_2$SO$_4$), filtered, and concentrated. Purification by chromatography (Silica gel: EtOAc/hexane: 1/3) afforded 10.26 g of 1-benzyloxycarbonyl-4,4-dimethoxyproline methyl ester.

(2) The compound obtained above was treated in a similar manner as described in Example 1 (1) to give 1-benzyloxycarbonyl-2-(4-bromobenzyl)-4,4-dimethoxyproline methyl ester.

(3) To a solution of the compound obtained above (4.76 g) in acetic acid (100 mL) was bubbled HBr gas for 15 minutes.

After stirring overnight, Et$_2$O was added to the mixture. The resulting solid was collected and added to a mixture of ethyl acetate and aqueous NaHCO$_3$. The organic solution was washed with aqueous NaHCO$_3$ and brine, dried (Na$_2$SO$_4$), filtered, and concentrated to give 2-(4-bromobenzyl)-4-oxoproline methyl ester.

(4) The compound obtained above was reacted with 3,5-dichlorophenyl isocyanate in a fashion similar to Example 1 (3) to afford N-[N-(3,5-dichlorophenyl)carbamoyl]-2-(4-bromobenzyl)-4-oxoproline methyl ester. MS (m/z) 499 (MH$^+$). mp 194.2° C.

(5) A solution of the compound obtained above (0.115 g) in toluene (4 mL) containing p-toluenesulfonic acid (10 mg) was refluxed for 5 h and then concentrated. Purification by chromatography (Silica gel: EtOAc/hexane: 1/4) afforded 97.6 mg of the titled compound. mp. 85.4° C.; MS (m/z) 467 (MH$^+$).

Example 36

5-(4-Bromobenzyl)-3-(3,5-dichlorophenyl)-7-methoxycarbonylmethylene-1,3-diazabicyclo[3.3.0]octane-2,4-dione The titled compound (mixture of E/Z isomers (1.2/1.0)) was prepared in a fashion similar to Example 17 from 5-(4-bromobenzyl)-3-(3,5-dichlorophenyl)-1,3-diazabicyclo[3.3.0]-octane-2,4,7-trione. MS (m/z) 523 (MH$^+$), mp 74.9° C.

Example 37

5-(4-Bromobenzyl)-3-(3,5-dichlorophenyl)-7-carboxymethyl-1,3-diazabicyclo[3.3.0]oct-6-ene-2,4-dione To a solution of 5-(4-Bromobenzyl)-3-(3,5-dichlorophenyl)-7-methoxycarbonylmethylene-1,3-diazabicyclo[3.3.0]octane-2,4-dione (0.564 g) in THF (4 mL) and methanol (1 mL) at 0° C. was added 2N LiOH (1.20 mL). After 2 hours, the reaction mixture was concentrated and the residue was suspended in 1 N HCl and filtered. A solution of the filtrate (0.10 g) in thionyl chloride (5 mL) was refluxed for 30 minutes. The reaction mixture was concentrated and the residue was diluted with EtOAc and water. The organic solution was collected and dried (Na$_2$SO$_4$), filtered, and concentrated. Purification by chromatography (Silica gel: 4% MeOH/CH$_2$Cl$_2$, Chromatotron) afforded 0.063 g of the titled compound. MS (m/z) 509 (MH$^+$), mp 101.5° C.

Example 38

(8R)-5-(4-Bromobenzyl)-3-(3,5-dichlorophenyl)-8-phenyl-1,3-diazabicyclo[3.3.0]octane-2,4-dione The titled compound was prepared in a fashion similar to Example 1. MS (m/z) 530 (MH⁺), mp. 72.4° C.

The following compounds (Examples 39-44) were prepared in a fashion similar to Example 1 using the requisite isocyanate, provided that KHMDS was replaced with LDA.

TABLE 2

| Example No. | A | X | Y | mp, ° C. | MS (MH⁺) |
|---|---|---|---|---|---|
| | | | | Physicochemical data | |
| 39 | N | Cl | Cl | 76.3 | 455 |
| 40 | CH | NO$_2$ | NO$_2$ | 106.1 | 475 |
| 41 | CCl | NO$_2$ | H | 61.5 | 465 |
| 42 | CH | NO$_2$ | H | 53.8 | 430 |
| 43 | CH | Me | Me | 176.6 | 413 |
| 44 | CNMe$_2$ | H | H | 58.5 | 428 |

Example 45

6-[4-[2-[[2-(dimethylamino)ethoxy]methyl]phenyl]-benzyl]-8-(3,5-dichlorophenyl)-1,8-diazabicyclo[4.3.0]nonane-7,9-dione (1) To a solution of 6-[4-[2-(hydroxymethyl)phenyl]benzyl]-8-(3,5-dichlorophenyl)-1,8-diazabicyclo[4.3.0]nonane-7,9-dione (0.318 g) in CH$_2$Cl$_2$ (5 mL) was added thionyl chloride (0.2 mL) and the mixture was stirred for 1 hour at room temperature. The mixture was concentrated and the residue was redissolved in CH$_2$Cl$_2$ (5 mL) and evaporated again. The residue was dried under vacuum to give 6-[4-[2-(chloromethyl)phenyl]benzyl]-8-(3,5-dichlorophenyl)-1,8-diazabicyclo[4.3.0]nonane-7,9-dione.

(2) NaH (60% in oil, 0.090 mg) was added to a solution of N,N-dimethylethanolamine (0.58 mg) in DMF (5 mL) and the mixture was stirred for 30 minutes. To the reaction mixture was added a solution of the compound obtained above in DMF (2 mL) and the mixture was stirred overnight at room temperature. The mixture was cooled in ice-water and quenched with EtOAc/water. The organic layer was separated and washed with water and brine. It was dried, filtered, stripped and the residue was purified by chromatography (silica gel: CHCl$_3$/MeOH: 50/1 to 30/1) to yield 84 mg of the titled compound. It was dissolved in MeOH and treated with 1N HCl/Et$_2$O (2 mL). The mixture was evaporated and dried under vacuum to yield 88 mg of the hydrochloride of the titled compound. MS (m/z) 566 (MH⁺).

Example 46

(5R,7S)-5-(4-Bromobenzyl)-3-(3,5-dichlorophenyl)-7-azido-1,3-diazabicyclo[3.3.0]octane-2,4-dione (1) To a solution of (4R)-N-(tert-Butoxycarbonyl)-4-hydroxy proline benzyl ester (8.96 g) in CH$_2$Cl$_2$ (100 mL) and DIEA (8 mL) at 0° C. was added methanesulfonyl chloride (3.00 mL). After 1 hour, the reaction mixture was allowed to stir at room temperature. After 2.5 hours, the mixture was diluted with CH$_2$Cl$_2$, washed with satd. NaHCO$_3$ and brine, dried (Na$_2$SO$_4$), filtered and concentrated. To a solution of the residue in DMF (100 mL) was added sodium azide (7.80 g) and placed in a preheated oil bath (75° C.). After stirring overnight, the reaction was diluted with water and extracted with Et$_2$O. The organic layer was washed with brine, dried (Na$_2$SO$_4$), filtered and concentrated. Purification by chromatography (silica gel: EtOAc/hexane: 1/10) afforded 7.70 g of (4S)-N-(tert-butoxycarbonyl)-4-azidoproline benzyl ester.

(2) The compound obtained above (5.69 g) was treated in a similar manner as described in Example 26 (4) to give (a mixture of diastereoisomers) (2R,4S)-N-(tert-butoxycarbonyl)-2-(4-bromobenzyl)-4-azidoproline benzyl ester (4.51 g).

(3) The compound obtained above (1.66 g) was treated in a similar procedure as described in Example 2 (2) to give (2R,4S)-2-(4-bromobenzyl)-4-azidoproline benzyl ester (1.0 g) and (2S,4S)-2-(4-bromobenzyl)-4-azidoproline benzyl ester (0.125 g) after purification by flash chromatography.

(4) The compound obtained above (2R,4S; 0.36 g) was treated in a similar procedure as described in Example 1 (3) and (4) to give (5R,7S)-5-(4-bromobenzyl)-3-(3,5-dichlorophenyl)-7-azido-1,3-diazabicyclo[3.3.0]octane-2,4-dione (0.28 g). MS (m/z) 495 (MH⁺).

Example 47

(5R,7S)-5-(4-Bromobenzyl)-3-(3,5-dichlorophenyl)-7-amino-1,3-diazabicyclo[3.3.0]octane-2,4-dione To a solution of (5R,7S)-5-(4-bromobenzyl)-3-(3,5-dichlorophenyl)-7-azido-1,3-diazabicyclo[3.3.0]octane-2,4-dione (0.83 g) in acetic acid (20 mL) was added zinc powder (0.90 g). After 1 hour at room temperature, the mixture was concentrated. The residue was suspended in satd. NaHCO$_3$ and EtOAc. The mixture was filtered and the organic layer was collected, washed with brine, dried (Na$_2$SO$_4$), filtered and concentrated. Purification of the residue by chromatography (silica gel: CH$_2$Cl$_2$: Chromatotron) afforded the titled compound (0.42 g). MS (m/z) 468 (MH⁺). mp 64.4° C.

Example 48

(5R,7S)-5-(4-Bromobenzyl)-3-(3,5-dichlorophenyl)-7-acetamido-1,3-diazabicyclo[3.3.0]octane-2,4-dione To a solution of (5R,7S)-5-(4-Bromobenzyl)-3-(3,5-dichlorophenyl)-7-amino-1,3-diazabicyclo[3.3.0]octane-2,4-dione (0.103 g) in THF (4 mL) was added acetic anhydride (0.031 mL). After 5 hours, the reaction mixture was concentrated and purified by chromatography (silica gel: CH$_2$Cl$_2$, Chromatotron) to afford the titled compound (0.125 g) MS (m/z) 510 (MH⁺). mp 140.7° C.

Example 49

(5R,7S)-5-(4-Bromobenzyl)-3-(3,5-dichlorophenyl)-7-methanesulfamide-1,3-diazabicyclo[3.3.0]octane-2,4-dione The titled compound was prepared in a fashion similar to Example 33: MS (m/z) 546 (MH$^+$). mp 125.8° C.

Example 50

(5R,7S)-5-(4-Bromobenzyl)-3-(3,5-dichlorophenyl)-7-dimethylamino-1,3-diazabicyclo[3.3.0]octane-2,4-dione The titled compound was prepared in a fashion similar to Example 29: MS (m/z) 496 (MH$^+$). mp 54° C.

Example 51

5-(4-Cyanobenzyl)-3-[3-chloro-5-(1-pyrrolyl)-phenyl]-1,3-diazabicyclo[3.3.0]octane-2,4-dione (1) To a solution of 5-chloro-1,3-phenylenediamine (2.00 g) in acetic acid (20 mL) was added 2,5-dimethoxytetrahydrofuran (1.8 mL). After 4 hours at reflux, the reaction mixture was concentrated. The residue was suspended in satd. NaHCO$_3$ and EtOAc. The reaction mixture was filtered and the organic layer was collected, washed with satd. NaHCO$_3$ and brine, dried (Na$_2$SO$_4$), filtered and concentrated. Purification of the residue by chromatography (silica gel: EtOAc/hexane: 1/4) afforded 0.54 g of 3-chloro-5-(1-pyrrolyl)aniline. MS (m/z) 193 (MH$^+$).

(2) To a solution of the compound obtained above (0.35 g) in CH$_2$Cl$_2$ (15 mL) was added a solution of trichloroacetyl chloride (0.17 g) dissolved in CH$_2$Cl$_2$ (2 mL). After 45 minutes at room temperature, 2-(4-cyanobenzyl)proline methyl ester (0.38 g) (prepared in a similar fashion to Example 1 (1) and (2)) dissolved in CH$_2$Cl$_2$ (10 mL) and triethylamine (2 mL) were added. After stirring overnight, the mixture was concentrated. The residue was dissolved in EtOAc, washed with satd. NaHCO$_3$ and brine, dried (Na$_2$SO$_4$), filtered and concentrated. Purification by chromatography (silica gel: EtOAc/hexane: 1/4, Chromatotron) afforded 0.51 g of N-[[3-chloro-5-(1-pyrrolyl)phenyl]carbamoyl]-2-(4-bromobenzyl)proline methyl. MS (m/z) 463 (MH$^+$).

(3) The titled compound was prepared from the above compound in a fashion similar to Example 1 (4): MS (m/z) 431 (MH$^+$). mp 266.5° C.

Example 52

5-(4-Cyanobenzyl)-3-[3-chloro-5-(2-formyl-1-pyrrolyl)-phenyl]-1,3-diazabicyclo[3.3.0]octane-2,4-dione To a solution of POCl$_3$ (0.1 mL) and DMF (0.3 mL) was added after 45 minutes a solution of 5-(4-cyanobenzyl)-3-[3-chloro-5-(1-pyrrolyl)-phenyl]-1,3-diazabicyclo[3.3.0]octane-2,4-dione (0.22 g) in DMF (0.5 mL). After 1 hour at room temperature, the reaction mixture was diluted with water (2 mL) and stirred. After 30 minutes, the mixture was diluted with CH$_2$Cl$_2$ and satd. NaHCO$_3$. The organic layer was collected, washed with brine, dried (Na$_2$SO$_4$), filtered and concentrated. Purification by chromatography (silica gel: EtOAc/hexane: 1/3, Chromatotron) afforded 0.091 g of the titled compound. MS (m/z) 459 (MH$^+$). mp 109.7° C.

Example 53

2-(tert-Butoxycarbonyl)-6-(4-bromobenzyl)-8-(3,5-dichlorophenyl)-1,2,8-triazabicyclo[4.3.0]nonane-7,9-dione (1) In direct analogy to the method of Chen et al. (Bioorganic and Med. Chem. Lett. 9 (1999), 1587), 1,2-di(tert-butoxycarbonyl)-hexahydropyridazine-3-carboxylic acid ethyl ester was synthesized from ethyl-5-bromo-pentanoate. MS (m/z) 381 (M+Na)$^+$.

(2) To a solution of freshly prepared LDA (13.2 mmol) in dry THF (30 mL) was added a solution of the compound obtained above (4.0 g) in dry THF (20 mL). The yellow solution was stirred at −78° C. for 30 minutes whereupon a solution of p-bromobenzylbromide (3.9 g) in dry THF (20 mL) was added via cannula. The reaction mixture was stirred at −78° C. for 30 minutes then warmed to −30° C. over 2 hours. After warming to room temperature, the reaction mixture was shaken with EtOAc/H$_2$O. The organic layer was separated and the aqueous layer was extracted with EtOAc. The combined organic layer was dried over MgSO$_4$, filtered and concentrated. Purification by liquid chromatography (silica gel: EtOAc/hexane: 12/88) gave 1,2-di(tert-butoxycarbonyl)-3-(4-bromobenzyl)hexahydropyridazine-3-carboxylic acid ethyl ester (2.3 g). MS (m/z) 327 (M−2Boc)$^+$.

(3) The compound obtained above was dissolved in TFA (50% in CH$_2$Cl$_2$, 30 mL) and stirred at room temperature for 3 hours. The mixture was washed with NaHCO$_3$ until effervescence ceased.

The organic layer was dried over MgSO$_4$ and concentrated to give 3-(4-bromobenzyl)hexahydropyridazine-3-carboxylic acid ethyl ester (650 mg). MS (m/z) 327 (M$^+$).

(4) Di-tert-butyl dicarbonate (454 mg) was added to a solution of the compound obtained above (650 mg) and triethylamine (0.32 mL) in CH$_2$Cl$_2$ (20 mL) at 0° C. After 5 hours at 0° C., the reaction mixture was warmed to room temperature and stirred for additional 20 hours. The mixture was shaken with EtOAc/H$_2$O, and the organic layer was separated and the aqueous layer was extracted with EtOAc. The combined organic layer was dried over MgSO$_4$, filtered and concentrated. Purification by liquid chromatography (silica gel: EtOAc/hexane: 35/65) gave 1-(tert-butoxycarbonyl)-3-(4-bromobenzyl)hexahydropyridazine-3-carboxylic acid ethyl ester (580 mg).

(5) 3,5-Dichlorophenylisocyanate (306 mg) was added to a solution of the compound obtained above (580 mg) in dry toluene and the reaction mixture was heated to 95° C. The progress of the reaction was monitored by MS (following appearance of a peak at 470). Two further portion of 3,5-dichlorophenylisocyanate (306 mg) were added at 24 hours and 48 hours. After a total of 50 hours, the reaction mixture was shaken with EtOAc/H$_2$O. The organic layer was separated and the aqueous layer was extracted with EtOAc. The combined organic layer was dried over MgSO$_4$, filtered and concentrated. Purification by liquid chromatography (silica gel: EtOAc/Hexane: 30/70) and recrystallization from EtOAc/hexane to give the titled compound (303 mg). MS (m/z) 592 (M+Na)$^+$.

Example 54

6-(4-Bromobenzyl)-8-(3,5-dichlorophenyl)-1,2,8-triazabicyclo[4.3.0]nonane-7,9-dione 2-(tert-Butoxycarbonyl)-6-(4-bromobenzyl)-8-(3,5-dichlorphenyl)-1,2,8-triazabicyclo[4.3.0]nonane-7,9-dione (260 mg) was dissolved in TFA/CH$_2$Cl$_2$ (50%, 5 mL) and stirred at room temperature for 3 hours. The reaction mixture was then concentrated in vacuo, redissolved in CH$_2$Cl$_2$ (5 mL) and DIEA (0.22 mL) was added. The mixture was stirred at room temperature for 30 minutes and was shaken with CH$_2$Cl$_2$/H$_2$O. The organic layer was separated and the aqueous layer was extracted with CH$_2$Cl$_2$. The combined organic layer was dried over MgSO$_4$, filtered and concentrated. The residue was recrystallized from EtOAc/hexane to give the titled compound (180 mg). MS (m/z) 470 (M$^+$).

Example 55

3-(2,6-dichloro-4-pyridyl)-5-(4-bromobenzyl)-1,3-diazabicyclo[3.3.0]octane-2,4-dione (Solid Phase Synthesis)

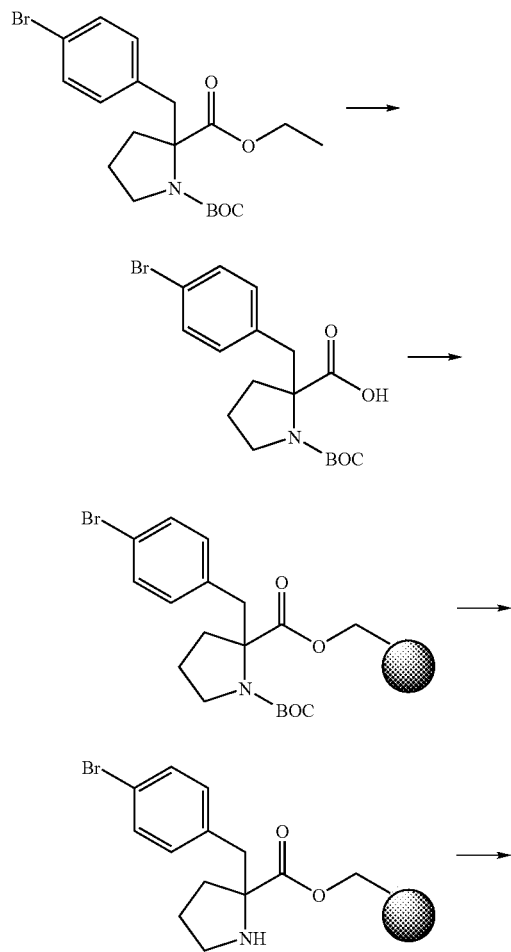

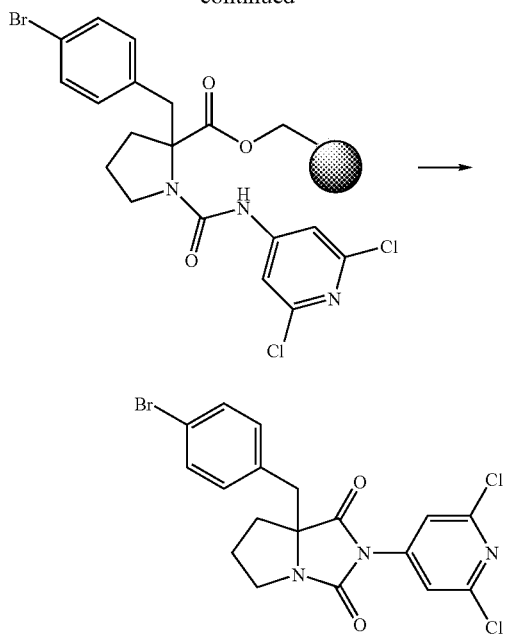

(In the above scheme,

means resin polymer.)

(1) A mixture of N-(tert-butoxycarbonyl)-2-(4-bromobenzyl)proline ethyl ester (3.00 g), LiOH (10 mmol), THF (25 mL), MeOH (10 mL) and H$_2$O (5 mL) was stirred at room temperature overnight. The mixture was then heated at 74° C. overnight. The mixture was concentrated in vacuo, and water was added. The mixture was washed with Et$_2$O and the aqueous layer was made acidic with the addition of 1N H$_2$SO$_4$. The aqueous layer was extracted with EtOAc. The EtOAc layer was washed with brine, dried over Na$_2$SO$_4$, and evaporated to give N-(tert-butoxycarbonyl)-2-(4-bromobenzyl)proline (3.02 g). MS (m/z) 284 (MH$^+$-t-Boc); mp: 143.9° C.

(2) To a solution of the compound obtained above (2.45 g) in DMF (100 mL) was added Merrifield Resin (4.70 g) and KF (1.1 g). The resulting mixture was stirred under N$_2$ at 80° C. overnight. The resin was filtered, and washed thoroughly with MeOH, H$_2$O and CH$_2$Cl$_2$, then dried in vacuo overnight to yield the resin-bound N-(tert-butoxycarbonyl)-2-(4-bromobenzyl)proline (6.66 g); FTIR (cm$^{-1}$) 1740, 1697, 1397, 1131, 1011.

(3) The compound obtained above was then deprotected using a 50% solution of TFA in CH$_2$Cl$_2$, followed by thorough washing, to give the resin-bound 2-(4-bromobenzyl)proline (6.09 g); FTIR (cm$^{-1}$) 1722.

(4) To the compound obtained above (200 mg) was added a DMF solution of 2,6-dichloro-4-pyridyl isocyanate (5 equiv.). This mixture was shaken at room temperature in a sealed receptacle overnight. The mixture was filtered, and the resin was washed with DMF, water and MeOH, and air-dried to give the resin-bound N-[(2,6-dichloro-4-pyridyl)carbamoyl]-2-(4-bromobenzyl)proline.

(5) A solution of DIEA (350 µL) in DMF (5 mL) was added to the compound obtained above, and the resulting mixture was then shaken at 50° C. for 2 hours, then at room temperature overnight. The resin was filtered and washed with MeOH, and the filtrate was evaporated. The residue was purified by reverse phase HPLC (gradient of 0%-70% $CH_3CN$ in water) to yield 3-(2,6-dichloro-4-pyridyl)-5-(4-bromobenzyl)-1,3-diazabichclo[3.3.0]octane-2,4-dione (58.0 mg). MS (m/z): 456 (MH$^+$); mp: 76.3° C.;

Example 56

8-(t-Butoxycarbonyl)-5-(4-cyanobenzyl)-3-(2,6-dichloro-4-pyridyl)-1,3,8-triazabicyclo[3.3.0]octane-2,4-dione (2) To a solution of aza-proline 4 (1.7 g) in dry $CH_2Cl_2$ (30 mL) was added 3,5-dichloropyrid-4-yl isocyanate (1 g) under $N_2$. The solution was stirred at room temperature for 18 hours. The reaction mixture was concentrated in vacuo and purified by chromatography ($SiO_2$, EtOAc/hexanes 25/75) to give the urea 5 (2.2 g). MS (m/z) 573 (MH$^+$).

(3) To a suspension of the urea 5 (1.95 g) in dry toluene/DME (50 mL/12 mL) was added triethylamine (0.18 mL). The reaction mixture was heated at 50° C. for 18 hours, whereupon it was concentrated in vacuo and purified by chromatography ($SiO_2$, EtOAc/DCM 1/9) to give the bicyclic derivative 6 (0.95 g). MS (m/z) 387 (M).

(4) Freshly prepared LDA (1.55 mmol) was added to a solution of the bicyclic compound 6 (0.5 g) in dry THF/DMPU (8 mL/1 mL) at −78° C. under $N_2$ to give an orange solution. After stirring at −78° C. for 20 minutes, 4-cyano-α-bromotoluene (382 mg) in THF (5 mL) was added via cannula and the reaction mixture stirred at −78° C. for 2.5 hours, then at room temperature for 0.5 hour. Water (30 mL) and EtOAc (50 mL) were added and the mixture was shaken. The aqueous phase was separated and extracted with EtOAc. The combined organics were dried over $Na_2SO_4$, filtered and

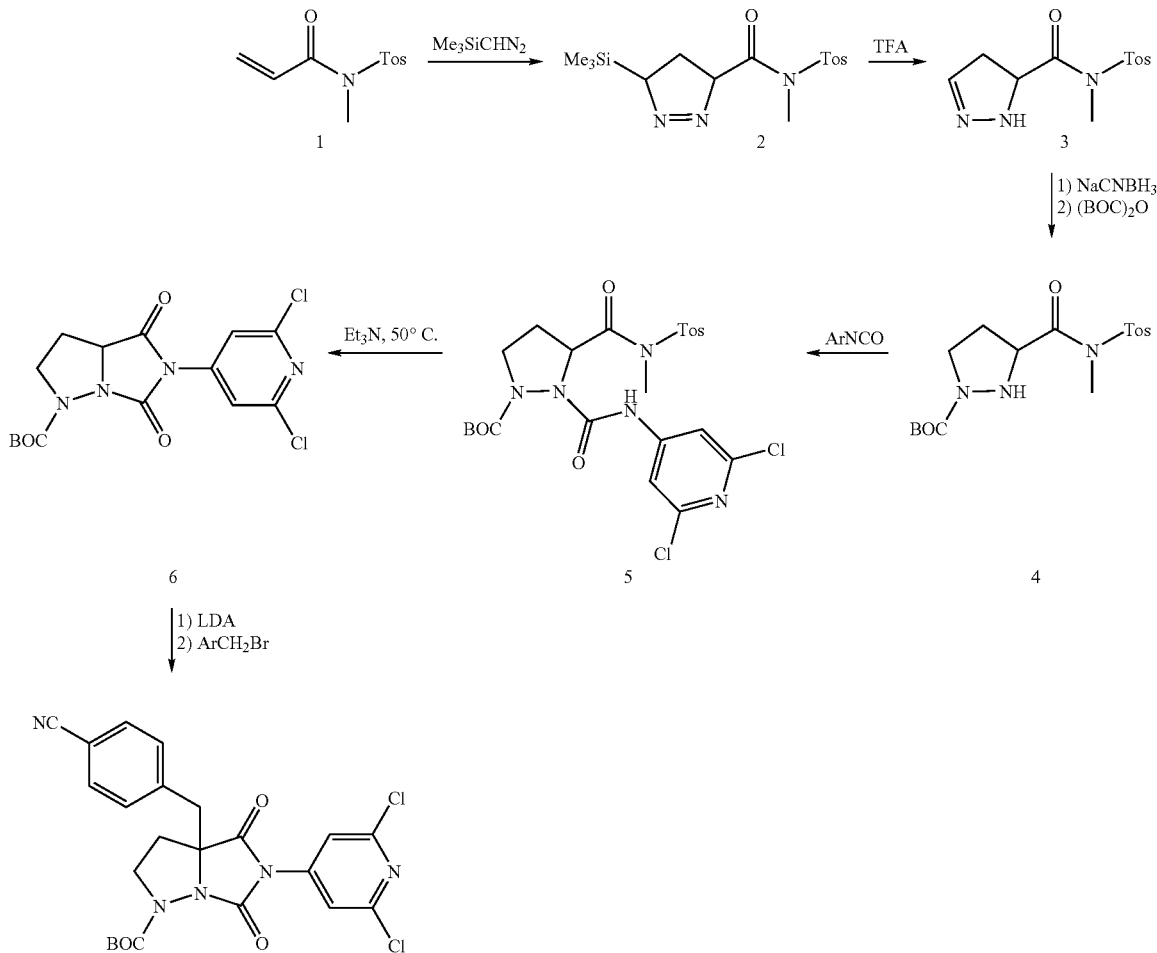

(1) Aza-proline derivative 4 was synthesized from N-methyl-N-tosylacrylamide 1 according to the method of Carreira et al (*J. Am. Chem. Soc.*, 1997, 119, 8379).

concentrated in vacuo. Purification of the residue by HPLC ($SiO_2$, MeCN/$H_2O$ 50/50) gave the titled compound (156 mg). MS (m/z) 502 (M$^+$), mp 179° C.

Example 57

5-(4-Cyanobenzyl)-3-(2,6-dichloro-4-pyridyl)-1,3,8-triazabicyclo [3.3.0]octane-2,4-dione

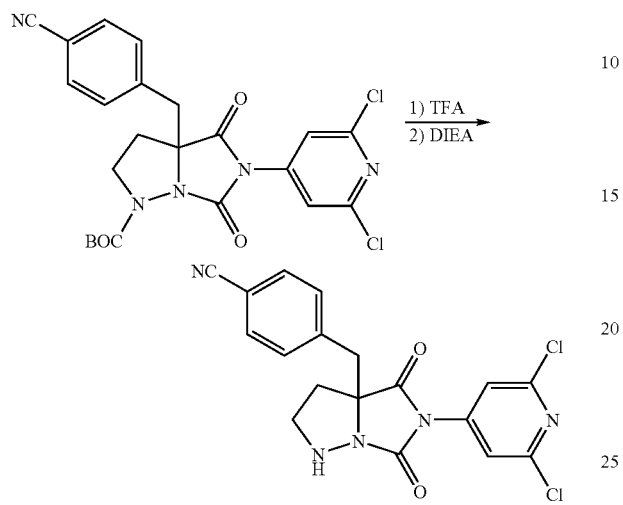

To a solution of the compound from Example 56 (102 mg) in CH$_2$Cl$_2$ (5 mL) at −10° C. was added TFA (1 mL). After warming to room temperature, the reaction mixture was stirred for a total of 1 hour while monitoring the progress by TLC. Upon consumption of the starting material, the reaction mixture was cooled to 0° C. and DIEA (4.5 mL) was added carefully. After 2 hours, water (20 mL) and EtOAc (30 mL) were added and the mixture shaken. The aqueous phase was then separated and extracted with EtOAc. The combined organic layers were dried over Na$_2$SO$_4$, filtered and concentrated in vacuo. The residue was purified by liquid chromatography (SiO$_2$, EtOAc) and re-crystallization from EtOAc/hexanes to give the titled compound (62 mg). MS (m/z) 402 (M); mp 187° C.

Example 58

(5R,7R)-5-[4-(Trifluoromethoxy)benzyl]-3-(2,6-dichloro-4-pyridyl)-7-hydroxy-1,3-diazabicyclo [3.3.0]octane-2,4-dione; and

Example 59

(5S,7R)-5-[4-(Trifluoromethoxy)benzyl]-3-(2,6-dichloro-4-pyridyl)-7-hydroxy-1,3-diazabicyclo [3.3.0]octane-2,4-dione

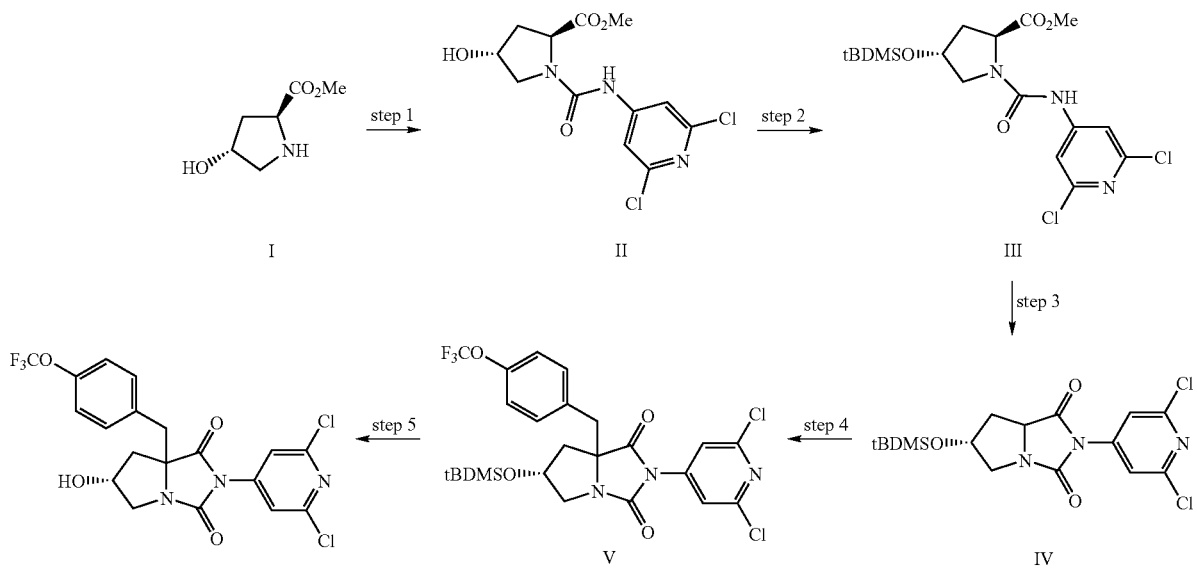

Step-1. To a suspension of L-4-trans-hydroxyproline methyl ester hydrochloride (5.25 g) in THF (50 mL) and DIEA (10 mL) was added 2,6-dichloropyrid-4-yl isocynate (7.00 g). After stirring overnight, the reaction mixture was concentrated. The residue was dissolved in EtOAc, washed with 0.5 N HCl, NaHCO$_3$, brine, dried (Na$_2$SO$_4$), filtered and concentrated. The residue was suspended in CH$_2$Cl$_2$ and the white solid filtered to give the urea II (7.12 g).

Step-2. To a suspension of the above urea derivative II (7.12 g) in CH$_3$CN (150 mL) was added imidazole (2.92 g) and tBDMSCl (6.52 g). After 7 hours, the reaction mixture was concentrated. The residue was dissolved in EtOAc, washed with 0.5 N HCl, NaHCO$_3$, brine, dried (Na$_2$SO$_4$), filtered and concentrated to give the desired product III (10.23 g).

Step-3. To a solution of the above crude urea derivative (10.23 g) in CH$_3$CN (100 mL) was added DIEA (5.0 mL) and heated to reflux. After refluxing for 2 days, the reaction mixture was concentrated and purified by flash chromatography (2:98 MeOH/CH$_2$Cl$_2$) to yield the desired compound IV (7.16 g).

Step-4. The compound from step 3 (3.55 g) was benzylated in a similar procedure as described for Example 56, step 4 yielding 5-[4-(Trifluoromethoxy)benzyl]-3-(2,6-dichloro-4-pyridyl)-7-(tert-butyldimethylsilyloxy)-1,3-diazabicyclo[3.3.0]octane-2,4-dione. Separation of the diastereomers 5R,7R (2.76 g) and 5S,7R (0.3 g) was achieved by flash chromatography eluting with CH$_2$Cl$_2$.

Step-5. Both diastereomers from step 4 were treated separately in a similar procedure as described in Example 2 (step 4) to give the following compounds:

(5R,7R)-5-[4-(Trifluoromethoxy)benzyl]-3-(2,6-dichloro-4-pyridyl)-7-hydroxy-1,3-diazabicyclo[3.3.0]octane-2,4-dione: 1.86 g, MS (m/z) 476 [MH$^+$], mp 52.4° C.

(5S,7R)-5-[4-(Trifluoromethoxy)benzyl]-3-(2,6-dichloro-4-pyridyl)-7-hydroxy-1,3-diazabicyclo[3.3.0]octane-2,4-dione: 0.18 g, MS (m/z) 476 [MH$^+$]. mp 162.3° C.

Example 60

(5R,7R)-5-(4-Cyanobenzyl)-3-(2,6-dichloro-4-pyridyl)-7-hydroxy-1,3-diazabicyclo[3.3.0]octane-2,4-dione The titled compound was prepared in a manner similar to Example 58. MS (m/z) 417 [MH$^+$]. mp 97.6° C.

Example 61

(5R,7S)-5-(4-Bromobenzyl)-3-(3,5-dichlorophenyl)-7-hydroxy-1,3-diazabicyclo[3.3.0]octane-2,4-dione The titled compound was prepared in a manner similar to Example 58 using 4-bromobenzyl bromide in step 4. MS (m/z) 469 [MH$^+$]. mp 60.4° C.

Example 62

(5R,7S)-5-[4-(Trifluoromethoxy)benzyl]-3-(2,6-dichloro-4-pyridyl)-7-azido-1,3-diazabicyclo[3.3.0]octane-2,4-dione The titled compound was prepared from (5R,7R)-5-[4-(Trifluoromethoxy)benzyl]-3-(2,6-dichloro-4-pyridyl)-7-hydroxy-1,3-diazabicyclo[3.3.0]octane-2,4-dione in a manner similar to Example 3 except that no heat was used in step 2. MS (m/z) 501 [MH$^+$]. mp 139.9° C.

Example 63

(5R,7S)-5-[4-(Trifluoromethoxy)benzyl]-3-(2,6-dichloro-4-pyridyl)-7-amino-1,3-diazabicyclo[3.3.0]octane-2,4-dione The titled compound was prepared from (5R,7S)-5-[4-(Trifluoromethoxy)benzyl]-3-(2,6-dichloro-4-pyridyl)-7-azido-1,3-diazabicyclo[3.3.0]octane-2,4-dione in a manner similar to Example 47. MS (m/z) 475 [MH$^+$]. mp 150.6° C.

Example 64

(5R,7S)-5-[4-(Trifluoromethoxy)benzyl]-3-(2,6-dichloro-4-pyridyl)-7-acetamido-1,3-diazabicyclo[3.3.0]octane-2,4-dione The titled compound was prepared from (5R,7S)-5-[4-(Trifluoromethoxy)benzyl]-3-(2,6-dichloro-4-pyridyl)-7-amino-1,3-diazabicyclo[3.3.0]octane-2,4-dione in a manner similar to Example 48. MS (m/z) 517 [MH$^+$]. mp 126.9° C.

Example 65

(5R,7S)-5-[4-(Trifluoromethoxy)benzyl]-3-(2,6-dichloro-4-pyridyl)-7-(ethylurea)-1,3-diazabicyclo[3.3.0]octane-2,4-dione To a solution of (5R,7S)-5-[4-(Trifluoromethoxy)benzyl]-3-(2,6-dichloro-4-pyridyl)-7-amino-1,3-diazabicyclo[3.3.0]octane-2,4-dione (0.085 g) in THF (5 mL) was added ethyl isocynate (25 mL). After stirring overnight at room temperature the reaction mixture was concentrated and purified by chromatography (silica gel: 98:2 CH$_2$Cl$_2$:MeOH, Chromatotron) to afford the titled compound (0.095 g). MS (m/z) 546 [MH$^+$]. mp 227.5° C.

Example 66

(5R,7S)-5-[4-(Trifluoromethoxy)benzyl]-3-(2,6-dichloro-4-pyridyl)-7-(3-carboxypropanoylamino)-1,3-diazabicyclo[3.3.0]octane-2,4-dione To a solution of (5R,7S)-5-[4-(Trifluoromethoxy)benzyl]-3-(2,6-dichloro-4-pyridyl)-7-amino-1,3-diazobicyclo[3.3.0]octane-2,4-dione (0.155 g) in CH$_2$Cl$_2$ (4 mL) was added succinic anhydride (0.072 g) and DMAP (catalytic amount). After 4 hours, the reaction mixture was concentrated and purified by chromatography (silica gel: 95:5 CH$_2$Cl$_2$:MeOH, Chromatotron) to afford the titled compound (0.182 g). MS (m/z) 575 [MH$^+$]. mp 101.9° C.

Example 67

(5R,7S)-5-[4-(Trifluoromethoxy)benzyl]-3-(2,6-dichloro-4-pyridyl)-7-(isonicotinoylamino)-1,3-diazabicyclo[3.3.0]octane-2,4-dione To a solution of (5R,7S)-5-[4-(Trifluoromethoxy)benzyl]-3-(2,6-dichloro-4-pyridyl)-7-amino-1,3-diazobicyclo[3.3.0]octane-2,4-dione (0.075 g) in THF (5 mL) was added isonicotinic acid (0.041 g), EDC (0.050 g), HOBt (0.057 g), and DIEA (0.10 mL). After stirring overnight at room temperature, the reaction mixture was concentrated. The residue was dissolved in EtOAc, washed with NaHCO$_3$ and brine, dried (Na$_2$SO$_4$), filtered, concentrated and purified by chromatography (silica gel: 95:5 CH$_2$Cl$_2$:MeOH Chromatotron) to afford the titled compound (0.103 g). MS (m/z) 580 [MH$^+$]. mp 148° C.

Example 68

(5R,7S)-5-[4-(Trifluoromethoxy)benzyl]-3-(2,6-dichloro-4-pyridyl)-7-(dimethylaminoacetylamino)-1,3-diazabicyclo[3.3.0]octane-2,4-dione The titled compound was prepared in an analogous manner to Example 67. MS (m/z) 580 [MH$^+$]. mp 252° C.

Example 69

(5R,7S)-5-[4-(Trifluoromethoxy)benzyl]-3-(2,6-dichloro-4-pyridyl)-7-[3-(4-methyl-1-piperazinylcarbonyl)propanoylamino]-1,3-diazabicyclo[3.3.0]octane-2,4-dione To a solution of the compound from Example 66 (0.12 g) in THF (5 mL) was added N-methyl piperazine (50 μL), EDC (0.90 g), HOBt (0.090 g), and DIEA (0.10 mL). After stirring overnight the reaction mixture was concentrated. The residue was dissolved in EtOAc, washed with water and brine, dried (Na$_2$SO$_4$), filtered, concentrated and purified by chromatography (silica gel: 95:5 CH$_2$Cl$_2$: MeOH, Chromatotron) to afford the titled compound (0.10 g). MS (m/z) 657 [MH$^+$]. mp 70° C.

Example 70

(5R)-5-[4-(Trifluoromethoxy)benzyl]-3-(2,6-dichloro-4-pyridyl)-7-oxo-1,3-diazabicyclo[3.3.0]octane-2,4-dione PDC (0.40 g) was added to a solution of (5R, 7R)-5-[4-(Trifluoromethoxy)benzyl]-3-(2,6-dichloro-4-pyridyl)-7-hydroxy-1,3-diazobicyclo[3.3.0]octane-2,4-dione (0.21 g) in CH$_2$Cl$_2$ (10 mL). Additional PDC was added after 24 hours (0.43 g) and 96 hours (1.19 g). The reaction mixture was diluted with CH$_2$Cl$_2$, washed with water, 0.5 N HCl, and brine, dried (Na$_2$SO$_4$), filtered, concentrated and purified by chromatography (silica gel: CH$_2$Cl$_2$, Chromatotron) to afford the titled compound (0.134 g). MS (m/z) 474 [MH$^+$]. mp 166° C.

Example 71

(5R, 7S)-5-(4-Bromobenzyl)-3-(3,5-dichlorophenyl)-7-hydroxy-1,3-diazabicyclo[3.3.0]octane-2,4-dione The titled compound was prepared in a manner similar to Example 2 using (4S)-N-(tert-butoxycarbonyl) 4-hydroxy L-proline benzyl ester as starting material. MS (m/z) 470 [MH$^+$]. mp 113.6° C.

Example 72

(5R, 7R)-5-(4-Bromobenzyl)-3-(3,5-dichlorophenyl)-7-azido-1,3-diazabicyclo[3.3.0]octane-2,4-dione The titled compound was prepared from (5R, 7S)-5-(4-bromobenzyl)-3-(3,5-dichlorophenyl)-7-hydroxy-1,3-diazabicyclo[3.3.0]octane-2,4-dione in a manner similar to Example 3. MS (m/z) 495 [MH$^+$]. mp 83.4° C.

Example 73

(5R, 7R)-5-(4-Bromobenzyl)-3-(3,5-dichlorophenyl)-7-amino-1,3-diazabicyclo[3.3.0]octane-2,4-dione The titled compound was prepared from (5R, 7R)-5-(4-bromobenzyl)-3-(3,5-dichlorophenyl)-7-azido-1,3-diazabicyclo[3.3.0]octane-2,4-dione in a manner similar to Example 47. MS (m/z) 469 [MH$^+$]. mp 87.4° C.

During the reduction process, two elimination products were isolated in 11% combined yield as a 10:1 mixture of Example 74 and Example 75.

Example 74

(5S)-5-(4-Bromobenzyl)-3-(3,5-dichlorophenyl)-1,3-diazabicyclo[3.3.0]oct-6-en-2,4-dione

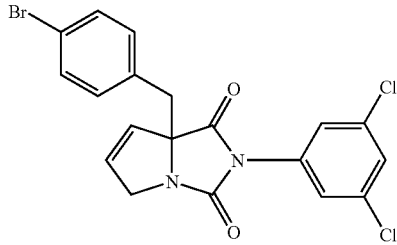

MS (m/z) 474 [MNa$^+$]. mp 97° C.

Example 75

(5R)5-(4-Bromobenzyl)-3-(3,5-dichlorophenyl)-1,3-diazabicyclo[3.3.0]oct-7-en-2,4-dione

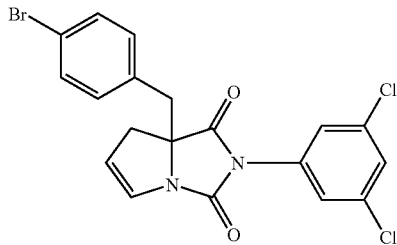

MS (m/z) 474 [MNa$^+$]. mp 52° C.

Example 76

(5R, 7R)-5-(4-Bromobenzyl)-3-(3,5-dichlorophenyl)-7-acetamido-1,3-diazabicyclo[3.3.0]octane-2,4-dione The titled compound was prepared from (5R, 7R)-5-(4-bromobenzyl)-3-(3,5-dichlorophenyl)-7-amino-1,3-diazabicyclo[3.3.0]octane-2,4-dione in a manner similar to Example 48. MS (m/z) 511 [MH$^+$]. mp 156.9° C.

Example 77

(5R, 7R)-5-(4-Bromobenzyl)-3-(3,5-dichlorophenyl)-7-benzamide-1,3-diazabicyclo[3.3.0]octane-2,4-dione To a solution of (5R, 7R)-5-(4-bromobenzyl)-3-(3,5-dichlorophenyl)-7-amino-1,3-diazabicyclo[3.3.0]octane-2,4-dione (0.065 g) in THF (5 mL) was added DIEA (0.50 mL) and benzoyl chloride (0.20 mL). After 3.5 hours, the reaction mixture was concentrated and purified by chromatography (silica gel: 98:2 CH$_2$Cl$_2$: methanol, Chromatotron) to afford the titled compound (0.073 g). MS (m/z) 594 [MNa$^+$]. mp 149.6° C.

The following compounds were prepared in an analogous manner to Example 77.

TABLE 3

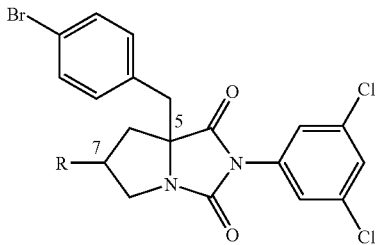

| Example | Diastereomer | R | Physicochemical Properties |
|---|---|---|---|
| 78 | 5R, 7R | —HN—C(=O)—C6H4—CO2Me | MS (m/z) 630 [MH+] mp 108° C. |
| 79 | 5R, 7R | —HN—C(=O)—C6H4—N(CH3)2 | MS (m/z) 615 [MH+] mp 154° C. |

Example 80

(5R, 7R)-5-(4-Bromobenzyl)-3-(3,5-dichlorophenyl)-7-(4-t-butoxycarbonylbenzoylamino)-1,3-diazabicyclo[3.3.0]octane-2,4-dione The titled compound was prepared from (5R, 7R)-5-(4-bromobenzyl)-3-(3,5-dichlorophenyl)-7-amino-1,3-diazabicyclo[3.3.0]octane-2,4-dione in a manner similar to Example 67. MS (m/z) 670 [M—H]⁻. mp 112° C.

Example 81

(5R, 7R)-5-(4-Bromobenzyl)-3-(3,5-dichlorophenyl)-7-(4-carboxybenzoylamino)-1,3-diazabicyclo[3.3.0]octane-2,4-dione.

To a solution of Example 80 (0.161 g) in CH$_2$Cl$_2$ (4 mL) was added TFA (1 mL). After 3 hours at room temperature, the reaction mixture was diluted with CH$_2$Cl$_2$, washed with water and brine, dried (Na$_2$SO$_4$), filtered, concentrated and purified by chromatography (silica gel: 80:20 CH$_2$Cl$_2$: MeOH, Chromatotron) to afford the titled compound (0.133 g). MS (m/z) 614 [M—H]⁻

Example 82

5-(4-Bromobenzyl)-3-(3,5-dichlorophenyl)-8-oxo-1,3-diazabicyclo[3.3.0]octane-2,4-dione

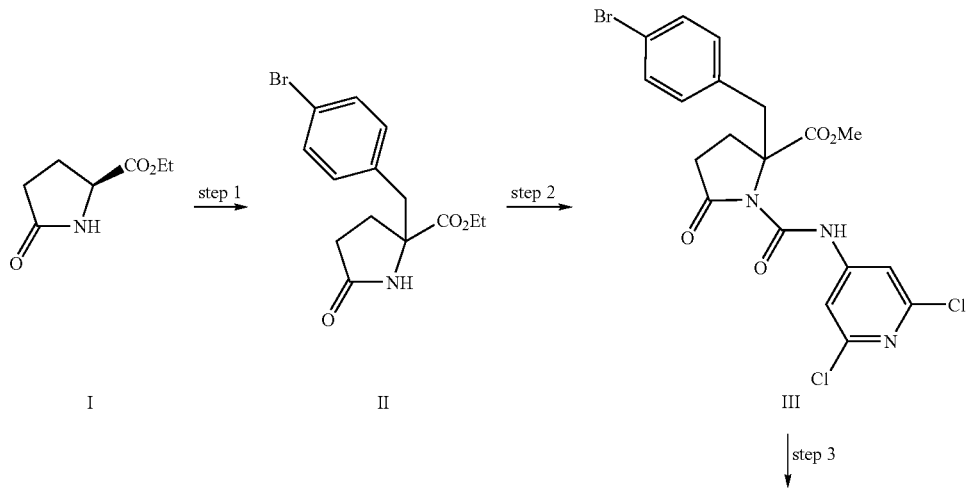

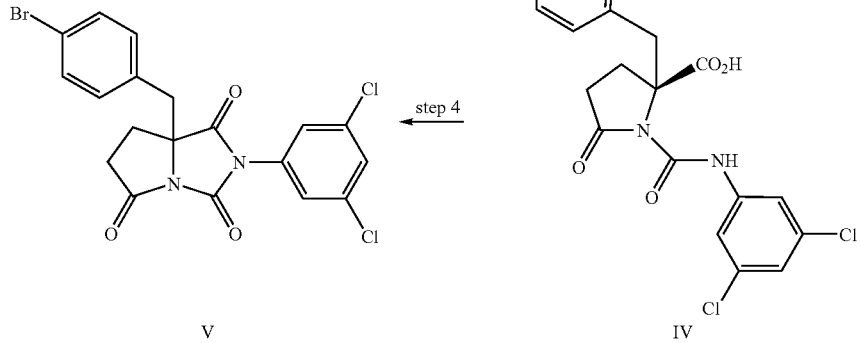

Step-1. To a solution of ethyl pyroglutamic ester (4.09 g) in THF at −78° C. was added KHMDS (12.75 g). After 30 minutes, 4-bromobenzyl bromide (6.79 g) in THF (25 mL) was added. The reaction mixture was allowed to warm to room temperature over 1 hour. After 1 hour at room temperature, the reaction mixture was concentrated. The residue was dissolved in EtOAc, washed with 0.1 N HCl and brine, dried (Na$_2$SO$_4$), filtered, concentrated and purified by chromatography (silica gel; 95:5 CH$_2$Cl$_2$: MeOH) to afford the benzylated derivative (5.00 g).

Step-2. The urea compound was prepared in a similar procedure as described in Example 1 (step 3).

Step-3. The compound obtained above (0.10 g) in THF (10 mL) was treated with 2 N LiOH (0.1 mL). After 2 hours, the reaction mixture was concentrated. The residue was dissolved in EtOAc, washed with 0.5 N HCl and brine, dried (Na$_2$SO$_4$), filtered, concentrated to give the acid (0.1 g).

Step-4. To a solution of the crude acid obtained above in THF (10 mL) was added EDC (0.17 g), HOBt (0.11 g) and DIEA (0.1 mL). After stirring overnight the reaction mixture was concentrated. The residue was dissolved in EtOAc, washed with 0.5 N HCl and brine, dried (Na$_2$SO$_4$), filtered, concentrated and purified by chromatography (silica gel: 95:5 CH$_2$Cl$_2$:MeOH, chromatotron) to afford the titled compound (0.048 g). MS (m/z) 491 [MNa$^+$]. mp 229.6° C.

Example 83

(7S)-5-(4-Bromobenzyl)-3-(3,5-dichlorophenyl)-7-phenyl-1,3-diazabicyclo[3.3.0]octane-2,4-dione

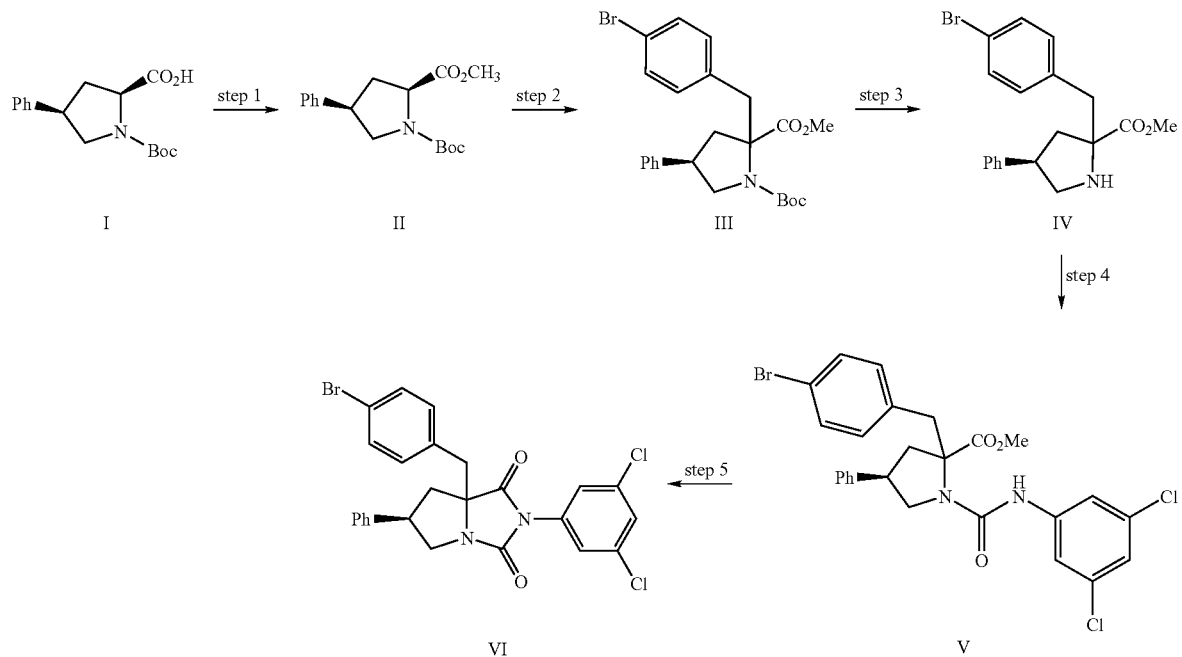

Step-1. To a solution of acid I (1.0 g) in CH$_2$Cl$_2$ (10 mL) was added DIEA (0.90 mL), HOBt (0.53 g), EDC (0.83 g) and MeOH (0.10 mL). After stirring overnight the reaction mixture was diluted with CH$_2$Cl$_2$, washed with 1 N HCl, NaHCO$_3$ and brine, dried (Na$_2$SO$_4$), filtered, concentrated to yield the desired ester II (0.97 g).

Step-2. The compound above was treated in a similar procedure as described in Example 26 (step 4) yielding a mixture of diastereomers of the comound III.

Step-3. The compound obtained above was treated in a manner similar to Example 1 (step 2).

Step-4. The compound obtained above was treated in a manner similar to Example 1 (step 3).

Step-5. The titled compound was prepared in a manner similar to Example 21 (step 2). MS (m/z) 551(MNa$^+$). mp. 123.5° C.

Example 84

5-(4-Bromobenzyl)-3-(2-chloro-6-dimethylamino-4-pyridyl)-1,3-diazabicyclo[3.3.0]octane-2,4-dione.

A mixture of Example 39 (0.26 g) and (Me)$_2$NH (2 M in THF, 5 mL) was heated in a sealed tube at 80° C. for 2 hours. The solution was concentrated and the residue was crystallized from EtOH to yield the titled compound (0.16 g). MS (m/z) 464 (MH$^+$); mp. 194.3° C.

Example 85

5-(4-Bromobenzyl)-3-(2-chloro-6-methylamino-4-pyridyl)-1,3-diazabicyclo[3.3.0]octane-2,4-dione By following the above procedure (Example 84) but replacing dimethylamine with methylamine the titled compound was obtained. MS (m/z) 450 (MH$^+$).

The following compounds were prepared using the requisite boronic acid in a manner similar to Example 7. Purification by chromatography (SiO$_2$, EtOAc/hexanes 1/1) gave a mixture of the mono-substituted bicycle 1 and the di-substituted bicycle 2 which was further purified by HPLC (MeCN/H$_2$O 50/50) to give the compounds:

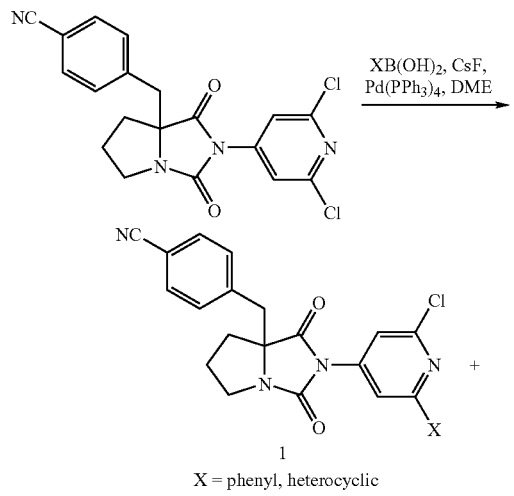

X = phenyl, heterocyclic

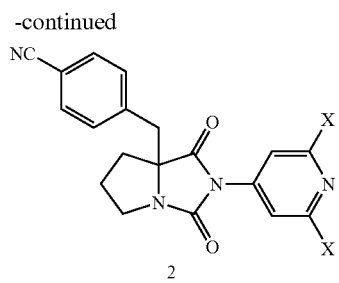

TABLE 4

| Example | Y | Z | Physicochemical Properties |
|---|---|---|---|
| 86 | 4-MeO-C$_6$H$_4$ | 4-MeO-C$_6$H$_4$ | MS (m/z) 545 (M$^+$) mp. 111° C. |
| 87 | C$_6$H$_5$ | C$_6$H$_5$ | MS (m/z) 485 (M$^+$) mp. 99° C. |
| 88 | 4-CF$_3$O-C$_6$H$_4$ | 4-CF$_3$O-C$_6$H$_4$ | MS (m/z) 622 (M$^+$) mp. 237° C. |
| 89 | 4-MeO-C$_6$H$_4$ | Cl | MS (m/z) 473 (M$^+$) mp. 179° C. |
| 90 | 4-CF$_3$O-C$_6$H$_4$ | Cl | MS (m/z) 528 (M$^+$) mp. 194° C. |
| 91 | C$_6$H$_5$ | Cl | MS (m/z) 443 (M$^+$) |
| 92 | 4-CF$_3$-C$_6$H$_4$ | Cl | MS (m/z) 511 (M$^+$) mp. 194° C. |
| 93 | 4-CN-C$_6$H$_4$ | Cl | MS (m/z) 468 (M$^+$) mp. 254° C. |

TABLE 4-continued

| Example | Y | Z | Physicochemical Properties |
|---|---|---|---|
| 94 | 3,4-dimethylisoxazol-5-yl | Cl | MS (m/z) 462 (M+) mp. 82° C. |
| 95 | 1-BOC-2-pyrrolyl (N-COOtBu) | 1-BOC-2-pyrrolyl (N-COOtBu) | MS (m/z) 663 (M+) mp. 173° C. |
| 96 | 1-BOC-2-pyrrolyl (N-COOtBu) | Cl | MS (m/z) 532 (M+) mp. 94° C. |
| 97 | 3-pyridyl | Cl | MS (m/z) 444 (M+) mp. 80° C. |

Example 98

5-(4-Cyanobenzyl)-3-[2,6-bis(2-pyrrolyl)-4-pyridyl]-1,3-diazabicyclo[3.3.0]octane-2,4-dione

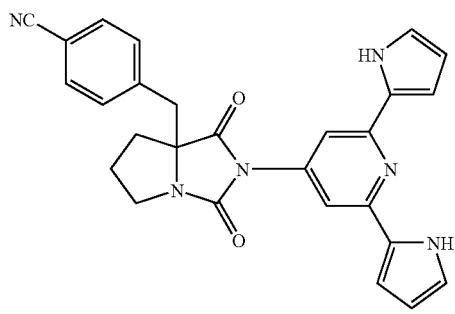

MS (m/z) 463 (M+)

Example 99

5-(4-Cyanobenzyl)-3-(2-chloro-6-(2-pyrrolyl)-4-pyridyl)-1,3-diazabicyclo[3.3.0]octane-2,4-dione

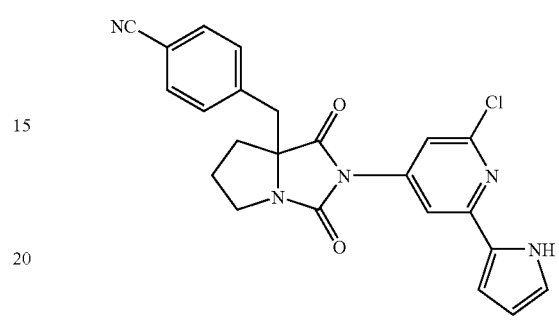

MS (m/z) 432 (M+)

The title compounds were prepared from Example 95 and Example 96 respectively by removal of the BOC group with TFA.

Example 100

6-(4-Bromobenzyl)-8-(2,6-dichloro-4-pyridyl)-1,2,8-triazabicyclo[4.3.0] nonan-7,9-dione

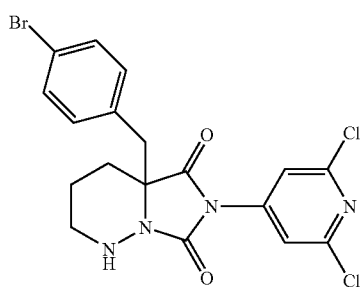

The titled compound was prepared in a manner analogous to Examples 53 and 54. MS m/z 470 (MH+); mp. 190° C. (dec).

Examples 101-105 were prepared in accordance with the following scheme.

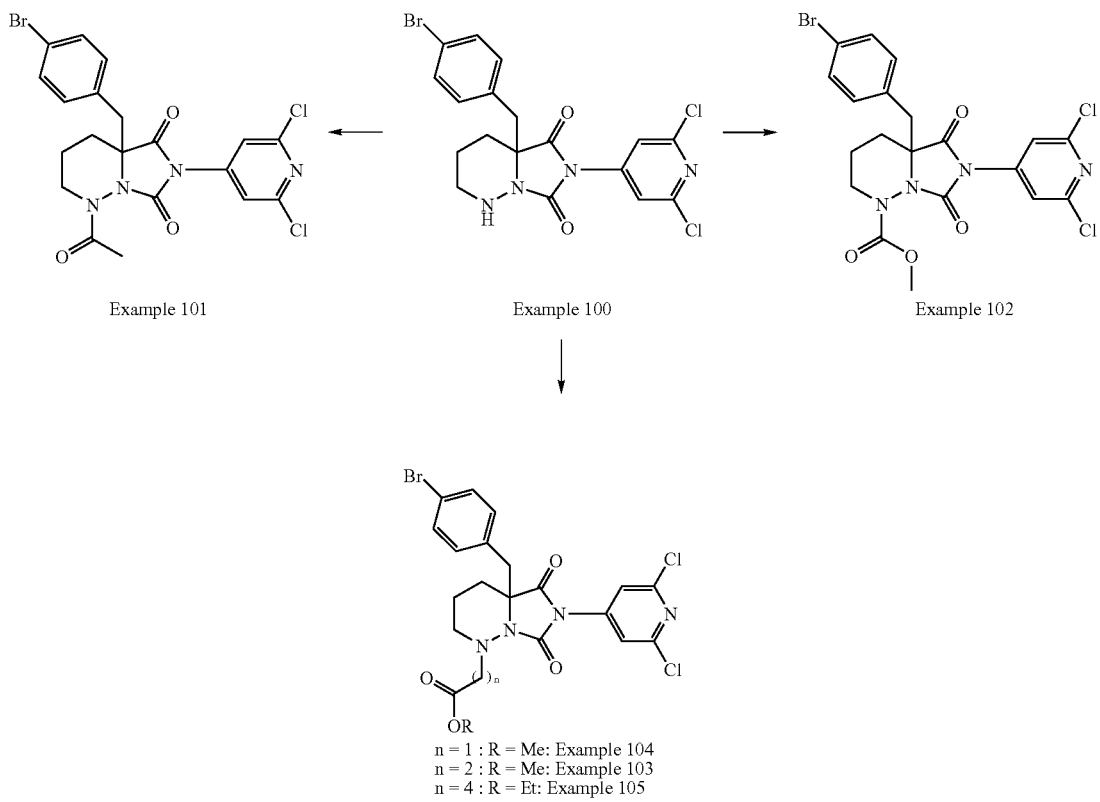

n = 1 : R = Me: Example 104
n = 2 : R = Me: Example 103
n = 4 : R = Et: Example 105

Example 101

6-(4-Bromobenzyl)-8-(2,6-dichloro-4-pyridyl)-2-acetyl-1,2,8-triazabicyclo[4.3.0]nonane-7,9-dione To a solution of the compound from Example 100 (80 mg) in dry THF (2 mL) under $N_2$ was added DIEA (0.073 mL) followed by AcCl (0.024 mL) and the reaction mixture stirred at room temperature for 18 hours. Water (10 mL) and EtOAc (10 mL) were added and the mixture was shaken. The aqueous phase was then separated and extracted with EtOAc. The combined organics were dried over $MgSO_4$, filtered and concentrated in vacuo. The residue was purified by chromatography (silica gel; EtOAc/hexanes; chromatotron) to give the titled compound (71 mg). MS (m/z) 513 (MH$^+$); mp. 91° C.

Example 102

6-(4-Bromobenzyl)-8-(2,6-dichloro-4-pyridyl)-2-methoxycarbonyl-1,2,8-triazabicyclo[4.3.0]nonane-7,9-dione To a solution of the compound from Example 100 (60 mg) in dry THF (2 mL) was added DIEA (0.044 mL), methylchloroformate (0.02 mL) and DMAP (catalytic amount). The reaction mixture was heated at 80° C. for 3 days during which more methylchloroformate (0.1 mL) was added after 24 hours and 48 hours. Water (10 mL) and EtOAc (10 mL) were added and the mixture shaken. The aqueous phase was separated and extracted with EtOAc. The combined organics were dried over $MgSO_4$, filtered and concentrated in vacuo. The residue was purified by chromatography (silica gel; EtOAc/hexanes; chromatotron) to give the titled compound (37 mg). MS (m/z) 529 (MH$^+$); Mp. 81° C.

Example 103

6-(4-Bromobenzyl)-8-(2,6-dichloro-4-pyridyl)-2-[2-(methoxycarbonyl)ethyl]-1,2,8-triazabicyclo[4.3.0]nonane-7,9-dione.

The compound from Example 100 (80 mg) was dissolved in methyl 3-bromopropanoate (0.5 mL) and DIEA (0.089 mL) and heated at 73° C. for 3 days. The reaction mixture was concentrated and purified by chromatography (silica gel; EtOAc/hexanes; chromatotron) to give the titled compound (38 mg). MS (m/z) 557 (MH$^+$); mp. 157° C.

The following compounds were prepared in a similar manner.

Example 104

6-(4-Bromobenzyl)-8-(2,6-dichloro-4-pyridyl)-2-methoxycarbonylmethyl-1,2,8-triazabicyclo[4.3.0]nonane-7,9-dione: MS (m/z) 543 (MH$^+$).

Example 105

6-(4-Bromobenzyl)-8-(2,6-dichloro-4-pyridyl)-2-[4-(ethoxycarbonyl)butyl]-1,2,8-triazabicyclo[4.3.0]nonane-7,9-dione: MS (m/z) 599 (MH$^+$).

Example 106

5-(4-Cyanobenzyl)-3-(3,5-dichlorobenzyl)-1,3-diazabicyclo[3.3.0]octane-2,4-dione

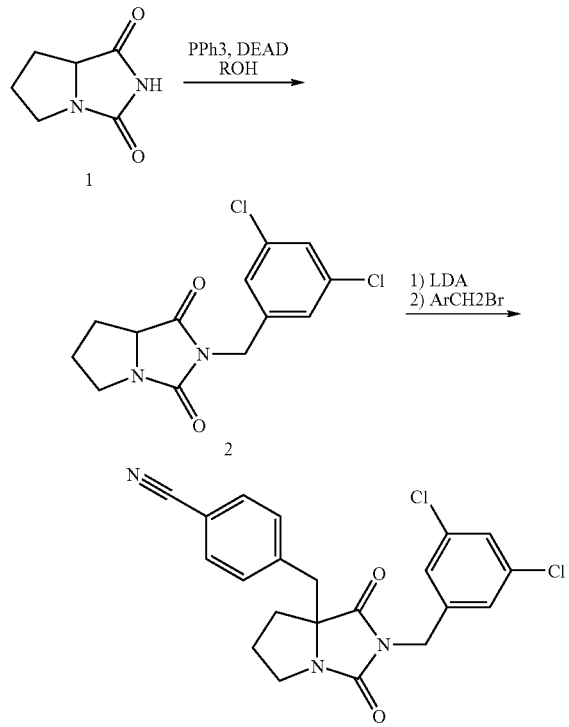

Step 1: To a solution of 1,3-diazabicyclo[3.3.0]octane-2,4-dione 1 (500 mg, *J. Med. Chem.*, 1995, 38, 3566), PPh$_3$ (1.2 g) and 3,5-dichlorobenzyl alcohol (690 mg) in THF (10 mL) at 0° C. was added DEAD (0.7 mL) drop-wise over 45 minutes. The mixture was allowed to warm to room temperature and H$_2$O/EtOAc (50 mL each) were added and the mixture was shaken. The aqueous phase was then separated and extracted with EtOAc. The combined organics were dried over MgSO$_4$, filtered and concentrated in vacuo. The residue was purified by chromatography (SiO$_2$, EtOAc/Hexanes) and recrystallization from EtOH/H_O to give the desired N-benzyl derivative 2 (550 mg). MS (m/z) 299 (M$^+$).

Step 2: The alkylation was done in a manner similar to Example 56 to give the titled compound.

MS (m/z) 414 (M$^+$); mp. 124° C.

The following compounds were prepared in a manner analogous to Example 106.

Example 107

5-(4-Cyanobenzyl)-3-[2-(3-chlorophenyl)ethyl]-1,3-diazabicyclo[3.3.0]octane-2,4-dione

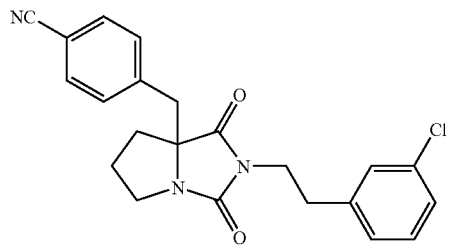

MS (m/z) 396 (M$^+$); mp. 148° C.

Example 108

5-(4-Cyanobenzyl)-3-(4-pyridylmethyl)-1,3-diazabicyclo[3.3.0]octane-2,4-dione

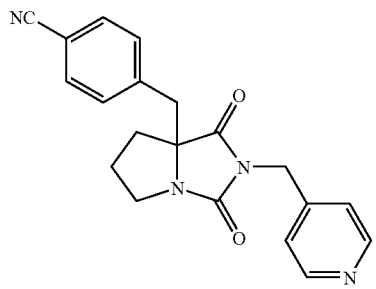

MS (m/z) 346 (M$^+$); mp. 154° C.

Example 109

5-(4-Bromobenzyl)-3-(3,4-dichlorobenzoyl)-1,3-diazabicyclo[3.3.0]octane-2,4-dione

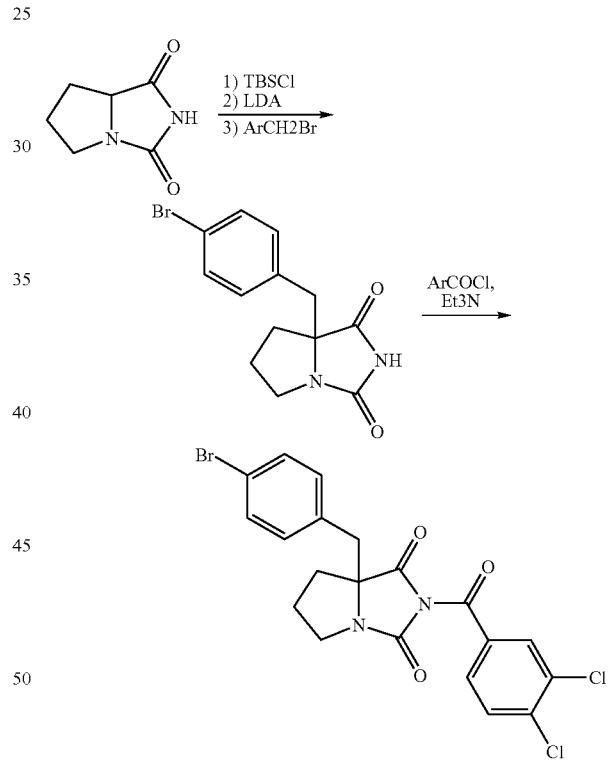

Step 1: To a solution of 1,3-diazabicyclo[3.3.0]octane-2,4-dione (5.24 g) in DMF (50 mL) was added Et$_3$N (6.2 mL) and tBDMSCl (6.2 g). The reaction mixture was stirred at room temperature for 2 hours whereupon water (30 mL) and DCM/hexanes (1/9, 100 mL) were added and the mixture was shaken. The aqueous phase was separated and extracted with DCM/hexanes (1/9). The combined organic layers were washed with water, dried over MgSO$_4$, filtered and concentrated in vacuo to give the protected imide (9.9 g) which was used without further purification. The alkylation was done in a manner similar to Example 106 to yield the desired benzylated material.

Step 2: To a solution of the compound from step-1 (100 mg), and Et₃N (0.054 mL) in THF (2 mL) was added 3,4-dichlorobenzoylchloride (74 mg). The reaction mixture was stirred at room temperature for 4 hours, concentrated in vacuo and purified by chromatography (silica gel; EtOAc/hexanes; Chromatotron) to give the titled compound (54 mg). MS (m/z) 483 (MH⁺); mp. 158° C.

Example 110

5-(4-Bromobenzyl)-3-(3,5-dichlorophenyl)-7,7-difluoro-1,3-diazabicyclo[3.3.0]octane-2,4-dione:

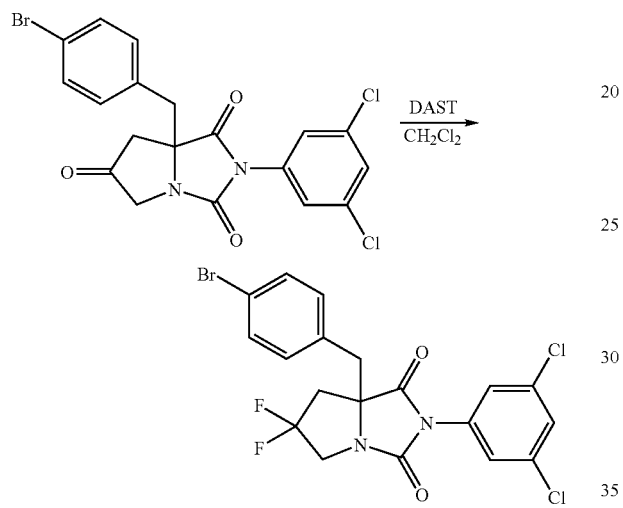

In a plastic vial, the compound from Example 35 (167 mg) was dissolved in anhydrous CH₂Cl₂ (5 mL) and DAST (47 μL) was added. The reaction mixture was stirred at room temperature for 6 hours, followed by refluxing for 2 hours. The reaction mixture was then cooled to room temperature and 10% NaHCO₃ (2 mL) was added. The mixture was extracted with EtOAc and the combined organic layers were dried over Na₂SO₄, filtered and evaporated. The residue was purified by chromatography (SiO₂, hexanes to 2:1 hexanes/EtOAc gradient elution) and HPLC (¹⁸C-Waters 40×210 mm, 1% HOAc/CH₃CN gradient) provided the titled compound (38 mg). MS (m/z) 488 (MH⁺) mp. 160.3° C.

Example 111

5-(4-Cyano-(α-hydroxybenzyl)-3-(3,5-dichlorophenyl)1,3-diazabicyclo[3.3.0]octane-2,4-dione

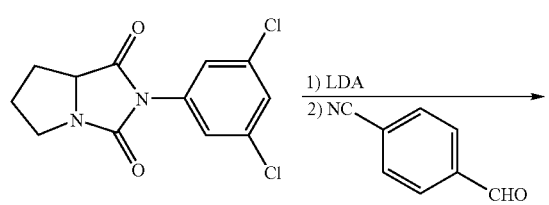

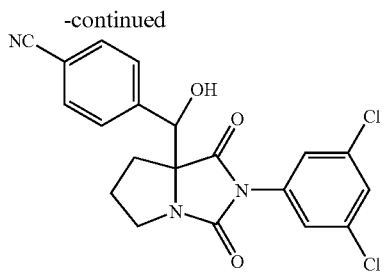

To a solution of 3-(3,5-dichlorophenyl)-1,3-diazabicyclo[3.3.0]octane-2,4-dione, (5.63 g) in anhydrous THF (20 mL) at −78° C. was added LDA prepared from n-BuLi (13.6 mL) and diisopropylamine (3.33 mL). The reaction mixture was stirred at −78° C. for 30 minutes then at 0° C. for 1 hour. To this mixture was added in one portion 4-cyanobenzaldehyde (3.64 g). The reaction mixture was allowed to warm to room temperature for 3 hours then poured onto 1 N HCl (50 mL). The mixture was extracted with EtOAc and the combined organic layers were dried over Na₂SO₄, filtered and the solvent evaporated. The residue was purified by chromatography (SiO₂, hexanes to 1:1 hexanes/EtOAc gradient elution) and HPLC (¹⁸C-Waters 40×210 mm, 1% HOAc/CH₃CN gradient) to provide the titled product (5.5 g). MS (m/z) 416 (MH⁺); mp. 184.4° C.

Example 112

5-(4-Cyanobenzoyl)-3-(3,5-dichlorophenyl)-1,3-diazabicyclo[3.3.0]octane-2,4-dione

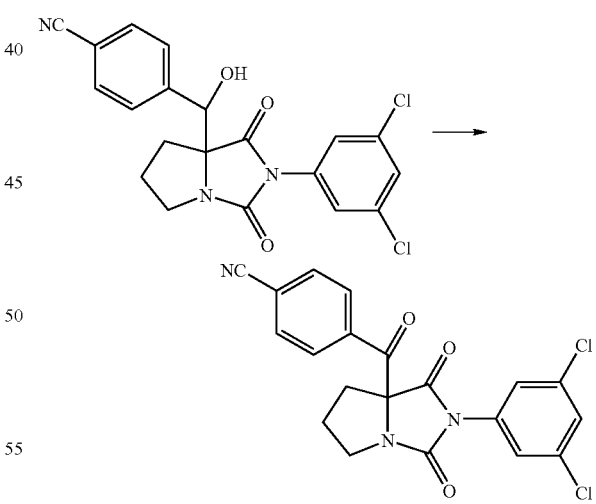

PCC (2.43 g) was added to a solution of the compound from Example 111 (3.90 g) in CH₂Cl₂ (20 mL) and the reaction mixture stirred at room temperature for 48 hours. The mixture was filtered though a plug of SiO₂ (washing with 1:1 CH₂Cl₂:EtOAc). The solvent was evaporated and the residue was purified by chromatography (SiO₂, hexanes to 1:1 hexanes/EtOAc gradient elution) providing the titled compound (1.97 g). MS (m/z) 414 (MH⁺). mp. 72.1° C.

Example 113

5-(4-Cyano-α,α-difluorobenzyl)-3-(3,5-dichlorophenyl)-1,3-diazabicyclo[3.3.0]octane-2,4-dione

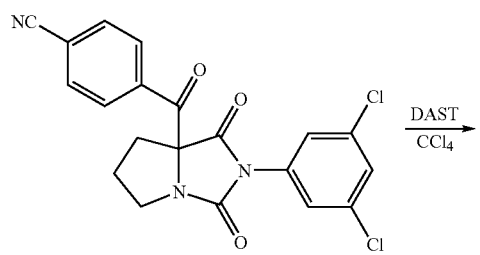

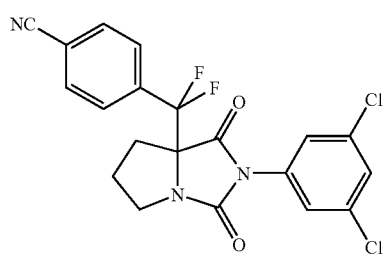

In a plastic tube, the compound from Example 112 (154 mg) was dissolved in CCl$_4$ (4 mL) and treated with DAST (98.3 μL). This reaction mixture was stirred for 22 hours at room temperature. The reaction mixture was quenched with 10% NaHCO$_3$ (5 mL) and then extracted with EtOAc. The combined organics were dried over Na$_2$SO$_4$, filtered and the solvent evaporated. Chromatography of the residue (SiO$_2$, hexanes to 2:1 hexanes/EtOAc gradient elution) provided the titled compound (141 mg). MS (m/z) 434 (MH$^+$). mp. 66° C.

Examples 114-116 were prepared in accordance with the following scheme (Scheme 12):

Scheme 12:

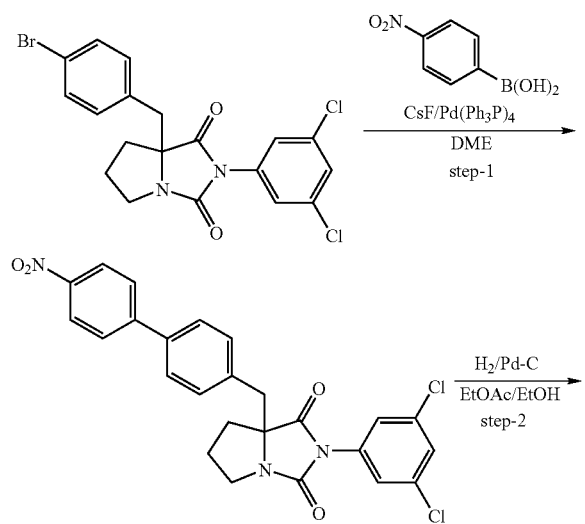

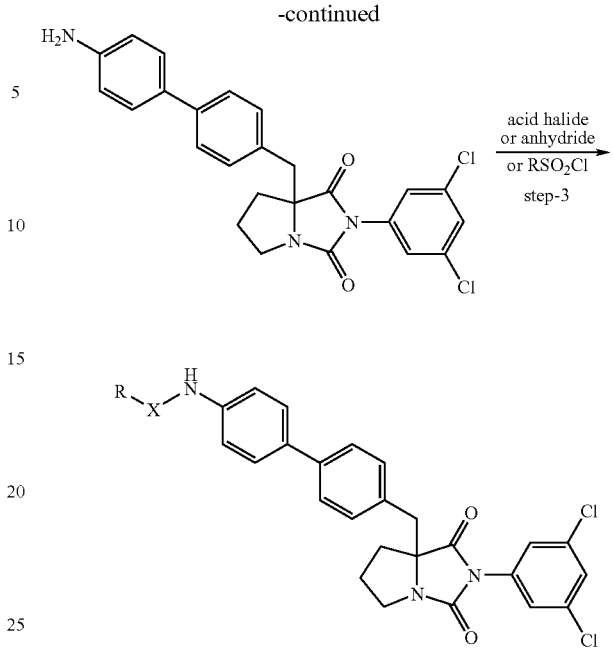

Example 114

5-[4-(4-Nitrophenyl)benzyl]-3-(3,5-dichlorophenyl)-1,3-diazabicyclo[3.3.0]octane-2,4-dione (Scheme 12, step 1):

The titled compound was prepared in a manner similar to the compound in Example 7. MS (m/z) 496 (MH$^+$). mp. 72-73° C.

Example 115

5-[4-(4-Aminophenyl)benzyl]-3-(3,5-dichlorophenyl)-1,3-diazabicyclo[3.3.0]octane-2,4-dione (Scheme 12, step 2)

The compound from Example 114 (140 mg) was dissolved in EtOAc (15 mL) and EtOH (5 mL). The solution was degassed (pump/N$_2$ purge) to remove O$_2$. Pd—C (5 mg, 5% degussa type) was added and H$_2$ was bubbled through the solution for 5 minutes. The reaction mixture was stirred under H$_2$ for 4.5 hours. The mixture was filtered through celite (washing with EtOAc). The solvent was evaporated and the residue purified by HPLC ($^{18}$C-Waters 40×210 mm, 1% HOAc/CH$_3$CN gradient) to provide the titled compound. MS (m/z) 466 (MH$^+$). mp. 278° C. (dec.).

Example 116

5-[4-(4-Acetylaminophenyl)benzyl]-3-(3,5-dichlorophenyl)-1,3-diazabicyclo[3.3.0]octane-2,4-dione (Scheme 12, step 3)

The compound from Example 115 (38 mg) was dissolved in CH$_2$Cl$_2$ (1 mL) and pyridine (1 mL). To this solution was added Ac$_2$O (200 μL) and the reaction mixture was refluxed for 15 minutes. The solvent was evaporated and the residue was purified by chromatography (SiO$_2$, hexanes to 1:1 hexanes/EtOAc gradient elution) to provide the titled compound (41 mg). MS (m/z) 508 (MH$^+$). mp. 123.9° C.

The following compounds were prepared in a manner similar to Example 116:

TABLE 5

| Example | R—X— | MS (m/z) |
|---|---|---|
| 117 | CH$_3$SO$_2$— | 542 (MH+) |
| 118 | HOOC(CH$_2$)$_2$CO— | 566 (MH+) |

The corresponding 3-aminophenyl derivatives were prepared in an analogous manner.

TABLE 6

| Example | R | MS (m/z) | mp (° C.) |
|---|---|---|---|
| 119 | AcNH | 508 (MH$^+$) | 98 |
| 120 | (CH$_3$SO$_2$)$_2$N | 622 (MH$^+$) | 123 |
| 121 | CH$_3$SO$_2$NH | 544 (MH$^+$) | 126.1 |
| 122 | EtOCONH | 538 (MH$^+$) | 115.3 |
| 123 | PhCONH | 570 (MH$^+$) | 119.7 |
| 124 | (CH$_3$NHCO)$_2$N | 580 (MH$^+$) | 111.5 |

Example 125

5-[4-[3-(Phenylthioureido)phenyl]benzyl]-3-(3,5-dichlorophenyl)-1,3-diazabicyclo[3.3.0]octane-2,3-dione

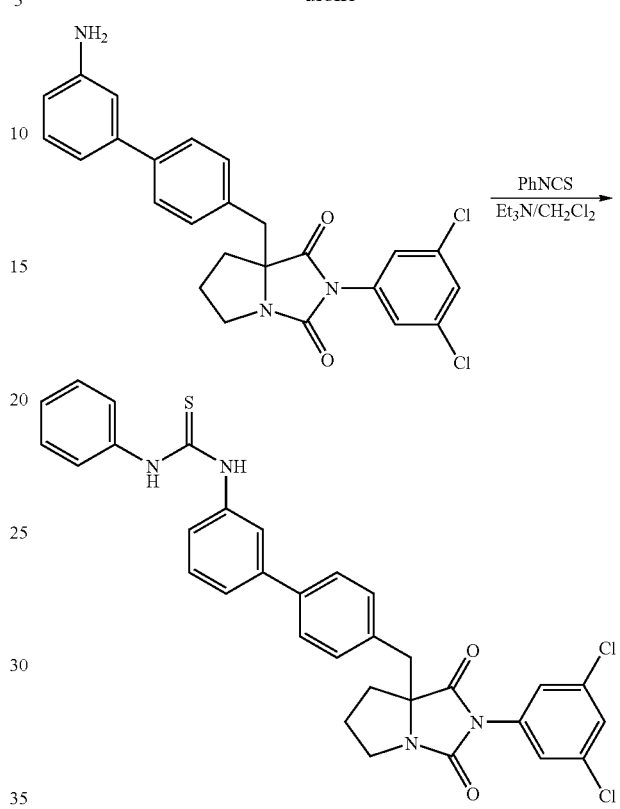

To a solution of the compound from Example 220 (100 mg) in CH$_2$Cl$_2$ (3 mL) and Et$_3$N (60 μL) was added PhNCS (31 μL) and the reaction mixture was stirred overnight at room temperature. The mixture was diluted with CH$_2$Cl$_2$ and then extracted in succession with 1N HCl, brine and NaHCO$_3$. The organic phase was dried over Na$_2$SO$_4$, filtered and the solvent was evaporated. The residue was purified by chromatography (SiO$_2$, hexanes to 4:1 hexanes/EtOAc gradient elution) and reverse phase HPLC ($^{18}$C, Waters 210×40 mm, 0.1 N HOAc to CH$_3$CN gradient) to provide the titled compound (35 mg). MS (m/z) 601 (MH$^+$). mp. 128.6° C.

Example 126

5-[4-[3-(Phenylureido)phenyl]benzyl]-3-(3,5-dichlorophenyl)-1,3-diazabicyclo[3.3.0]octane-2,4-dione

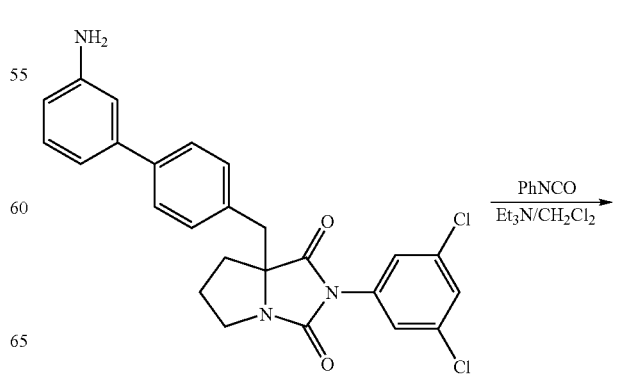

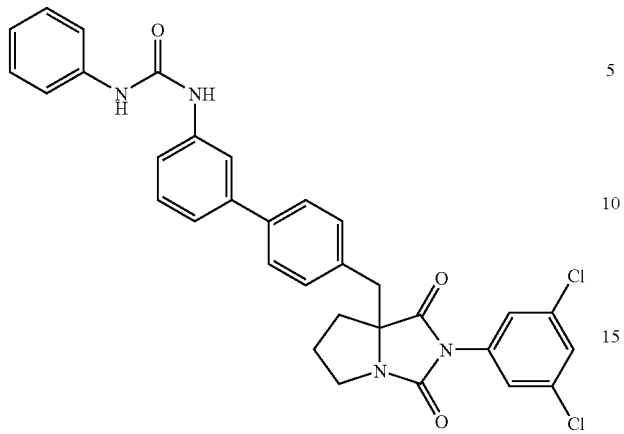

To a solution of the compound from Example 220 (100 mg) in $CH_2Cl_2$ (3 mL) and $Et_3N$ (60 μL) was added PhNCO (29 μL) and the reaction mixture was stirred overnight at room temperature. The mixture was diluted with $CH_2Cl_2$ and then extracted in succession with 1N HCl, brine and $NaHCO_3$. The organic phase was dried over $Na_2SO_4$, filtered and the solvent was evaporated. The residue was purified by chromatography ($SiO_2$, hexanes to 4:1 hexanes/EtOAc gradient elution) to provide the titled compound (95 mg). MS (m/z) 585 (MH+). mp. 150.2° C.

Example 127

5-[4-[3-(2-oxo-1-pyrrolidinyl)phenyl]benzyl]-3-(3,5-dichlorophenyl)-1,3-diazabicyclo[3.3.0]octane-2,4-dione

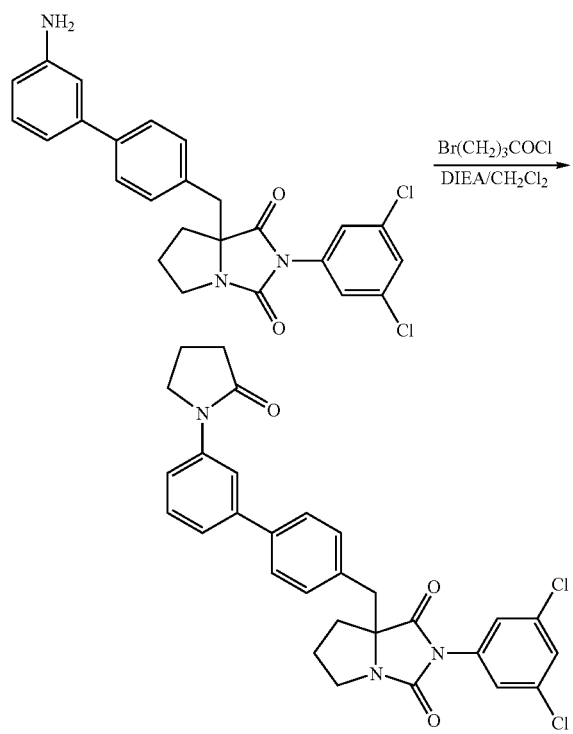

To a solution of the compound from Example 220 (100 mg) in $CH_2Cl_2$ (3 mL) and DIEA (75 μL) was added $Br(CH_2)_3COCl$ (30 μL) and the reaction mixture was stirred for 48 hours at room temperature. The mixture was diluted with $CH_2Cl_2$ and then extracted in succession with 1N HCl, brine and $NaHCO_3$. The organic phase was dried over $Na_2SO_4$, filtered and the solvent was evaporated. The residue was purified by chromatography ($SiO_2$, hexanes to 4:1 hexanes/EtOAc gradient elution) to provide the titled compound (40 mg). MS (m/z) 534 (MH+). mp. 86.5° C.

Example 128

5-[4-(5-tetrazolyl)benzyl]-3-(3,5-dichlorophenyl)-1,3-diazabicyclo[3.3.0]octane-2,4-dione:

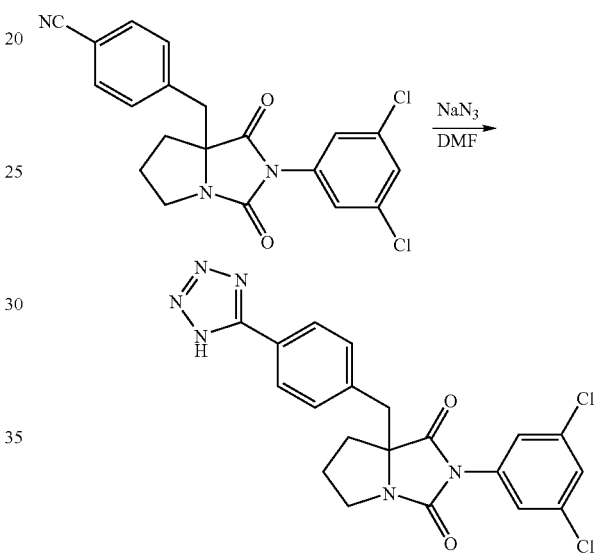

$NaN_3$ (64.5 mg) was added to a solution of Example 21 (137 mg) in DMF (3 mL). The reaction mixture was sealed and heated at 140° C. for 72 hours. The reaction mixture was cooled to room temperature and the solvent removed under reduced pressure. The residue was purified by HPLC ($^{18}$C-Waters 40×210 mm, 1% HOAc/$CH_3CN$ gradient) to provide the titled compound (27 mg). MS (m/z) 457 (MH+). mp. 194.8° C.

Example 129

5-(4-Amidinobenzyl)-3-(3,5-dichlorophenyl)-1,3-diazabicyclo[3.3.0]octane-2,4-dione:

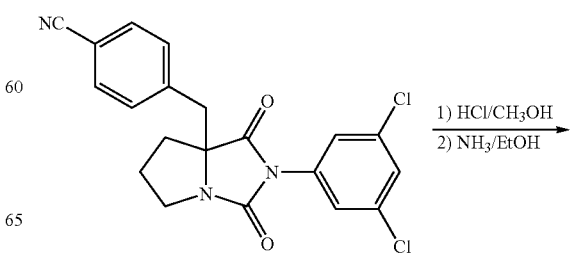

-continued

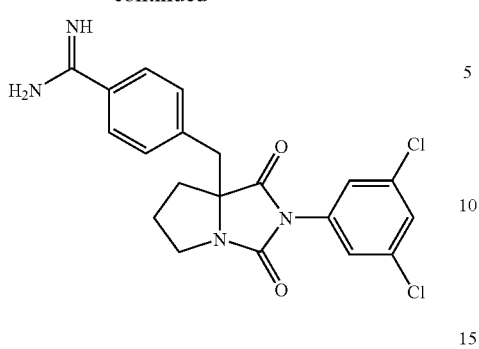

Anhydrous HCl was bubbled through a solution of Example 21 (219 mg) in CH₃OH (10 mL) for 15 minutes at 0° C. The reaction mixture was sealed in a pressure tube and allowed to stir for 48 hours at room temperature. Evaporation of the solvent followed by repeated dissolution and re-evaporation with CH₃OH provided the intermediate imino ether. The imino ether was then treated with NH₃/EtOH (2 M, 20 mL), resealed and stirred for 48 hours. Evaporation of the solvent followed by purification by HPLC ($^{18}$C-Waters 40×210 mm, 1% HOAc/CH₃CN gradient) provided the titled compound (177 mg). MS (m/z) 431 (MH⁺); mp. 187.6° C.

Example 130

5-(4-Cyanobenzyl)-3-(2,6-dichloro-4-pyridyl)-1,3-diazabicyclo[3.3.0]octane-2,4-dione

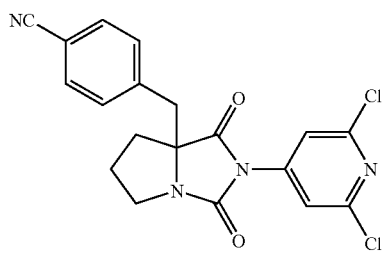

This compound was prepared in a manner similar to Example 21. MS (m/z) 401(M⁺). mp 96 C.

Examples 131-133 were prepared in accordance with the following scheme (Scheme 13):

Scheme 13:

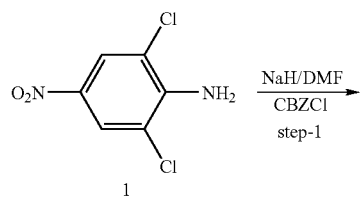

-continued

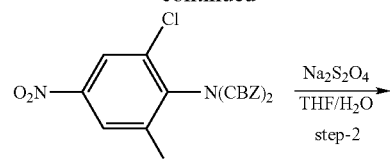

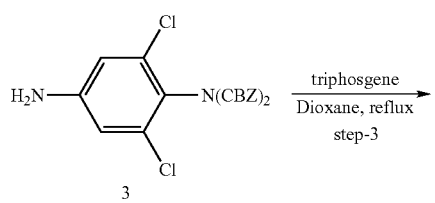

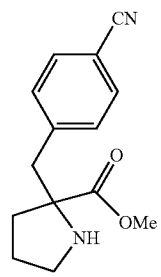

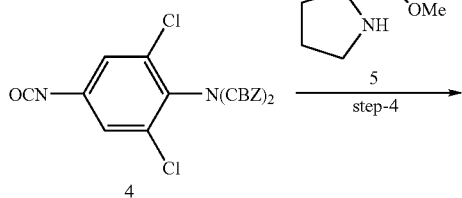

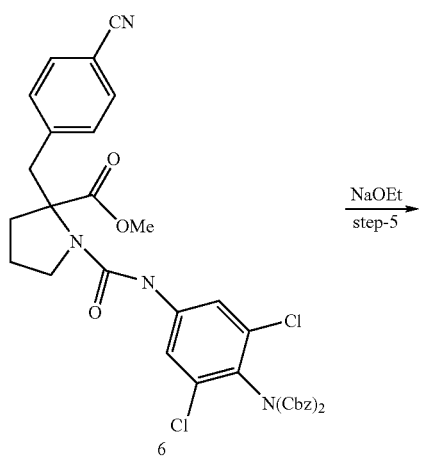

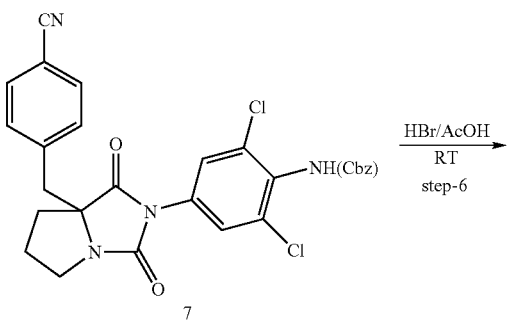

-continued

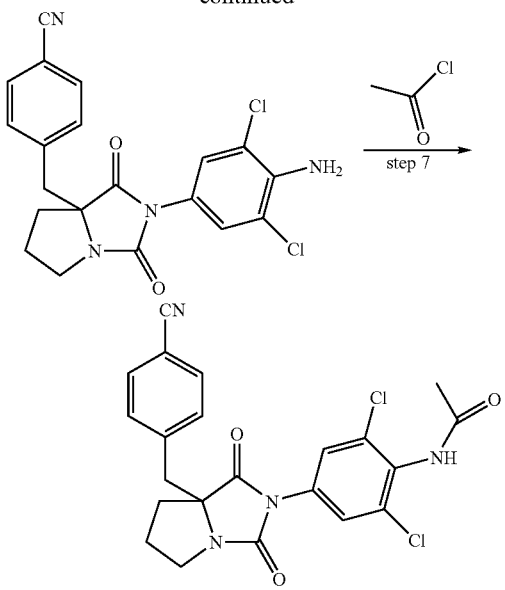

Example 131

5-(4-Cyanobenzyl)-3-(3,5-dichloro-4-benzyloxycarbonylaminophenyl)-1,3-diazabicyclo[3.3.0]octane-2,4-dione Step-1. NaH (0.64 g, 60% in oil) was added to an ice-cold solution of the 2,6-dichloro-4-nitroaniline 1 (3 g) in DMF (20 mL) and the reaction mixture was stirred for 20 minutes. CbzCl (2.72 g) was added slowly and the mixture was allowed to warm up to room temperature and stirred for overnight. The solution was partitioned between EtOAc/H$_2$O. The combined organic layers were dried over Na$_2$SO$_4$, filtered and concentrated. The product was purified by flash chromatography on silica gel to yield the desired compound (2.7 g). MS (m/z) 475 (MH$^+$).

Step-2. The CBZ protected aniline from above (2.7 g) was dissolved in THF/H$_2$O (15/10 mL). The mixture was cooled to 0° C., followed by the addition of Na$_2$S$_2$O$_4$ (2.0 g). The reaction solution was stirred at 0° C. for 3 hours. The solution was extracted with EtOAc. The combined organic layers were dried over Na$_2$SO$_4$, filtered and concentrated. The product was purified by flash chromatography on silica gel to yield the desired compound (2.1 g). MS (m/z) 445 (MH$^+$).

Step-3. Triphosgene (1.34 g) was added to a solution of the compound from step-2 (2 g) in dioxane (20 mL). The reaction solution was heated under reflux for overnight. Solvent was evaporated under vacuum. The product was used for the next step without further purification.

Step-4. The compound from step-3 (1.23 g) was added to an ice-cold solution of the proline derivative (compound 5, 0.58 g) in THF (10 mL) and the reaction mixture was stirred at 0° C. for 30 minutes. It was allowed to warm up to room temperature and stirred overnight. The reaction mixture was partitioned between EtOAc/H$_2$O. The combined organic layers were dried over Na$_2$SO$_4$, filtered and evaporated. The product was purified by flash chromatography on silica gel (1:1 EtOAc/Hexanes) to yield the titled compound (1.34 g). MS (m/z) 715 (MH$^+$).

Step-5. The urea compound from step-4 (260 mg) was cyclized in a manner similar to Example 1, step-4, to yield the titled compound (140 mg). ESMS (m/z) 549 (MH$^+$).

Example 132

5-(4-Cyanobenzyl)-3-(3,5-dichloro-4-aminophenyl)-1,3-diazabicyclo[3.3.0]octane-2,4-dione (Scheme 13, step 6)

The compound from Example 131 (100 mg) was dissolved in HBr (2 mL, 30% in AcOH). The resulting solution was stirred at room temperature for 30 minutes. The solution was extracted with EtOAc/H$_2$O. The combined organic layers were dried over Na$_2$SO$_4$, filtered and evaporated. The product was purified by preparative TLC to yield the titled compound (52 mg). MS (m/z) 415 (MH$^+$). mp. 103° C.

Example 133

5-(4-Cyanobenzyl)-3-(3,5-dichloro-4-acetylaminophenyl)-1,3-diazabicyclo[3.3.0]octane-2,4-dione (Scheme 13, step 7)

Acetyl chloride (10 µL) was added to a solution of the compound of Example 132 (20 mg) and DIEA (2 drops) in THF (1 mL). The resulting solution was stirred at room temperature for 2 hours. The solution was partitioned with EtOAc/H$_2$O. The combined organic layers were dried over Na$_2$SO$_4$, filtered and concentrated. The product was purified by preparative TLC to yield the titled compound (15 mg). MS (m/z) 457 (MH$^+$).

Examples 134-137 were prepared according to the following scheme (Scheme 14):

Scheme 14:

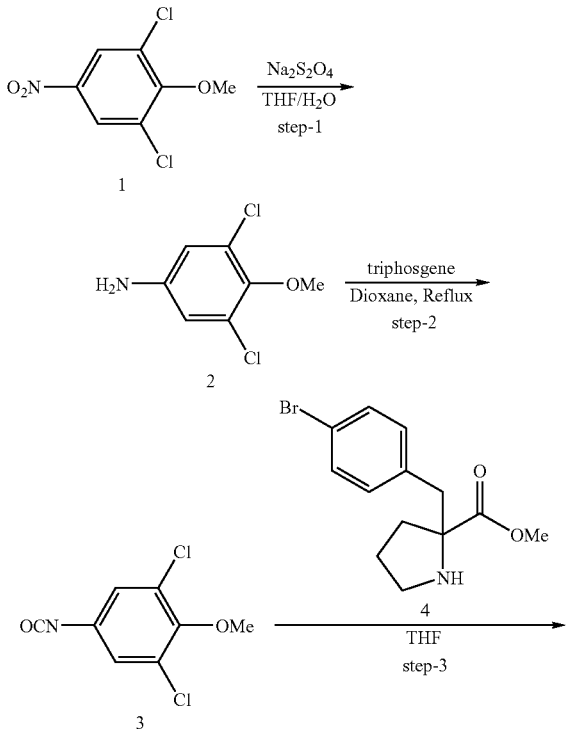

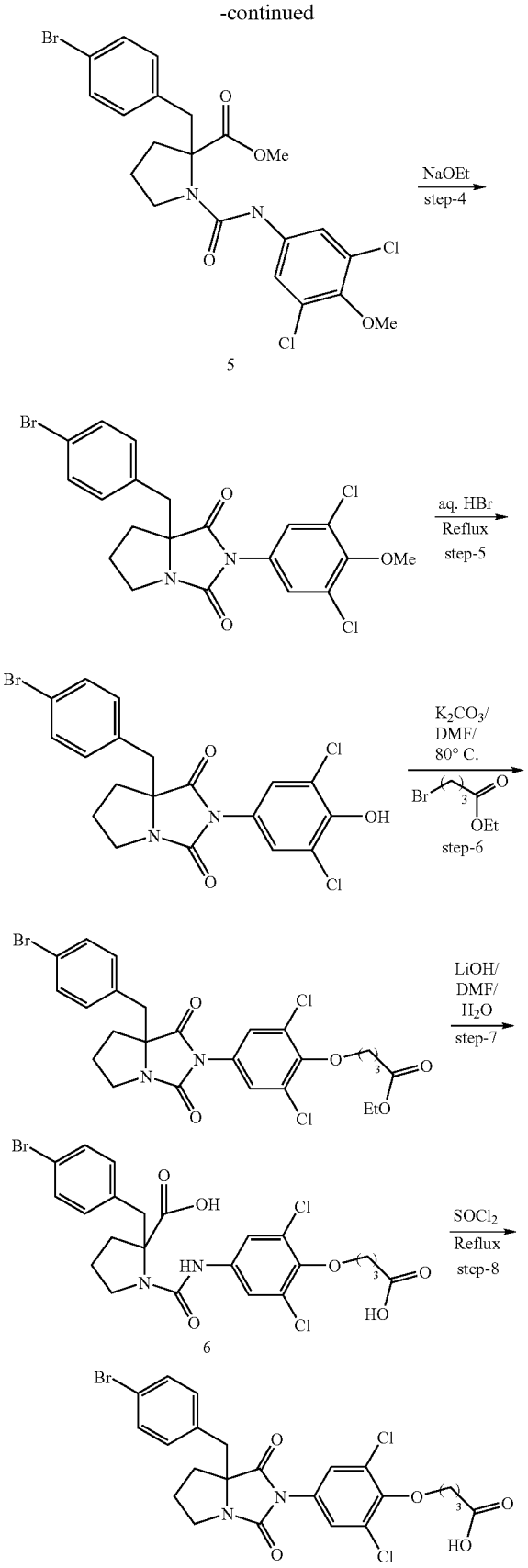

Example 134

5-(4-Bromobenzyl)-3-(3,5-dichloro-4-methoxyphenyl)-1,3-diazabicyclo[3.3.0]octane-2,4-dione Step-1. 2,6-Dichloro-4-nitroanisole (2 g) was reduced to the corresponding aniline (1.5 g) as described in the Example 131. MS (m/z) 192 (MH$^+$).

Step-2. A solution of the above aniline (2.12 g) and triphosgene (3.28 g) in dioxane (20 mL) was refluxed for 24 hours. The solvent was evaporated and the product was used for next step without further purification.

Step-3. The above isocyanate (2.46 g) was added to an ice-cold solution of the proline derivative (3 g) in THF (20 mL). The resulting solution was stirred at 0° C. for 30 minutes and then allowed to warm up to room temperature and stirred overnight. The reaction mixture was partitioned between EtOAc/H$_2$O. The combined organic layers were dried over Na$_2$SO$_4$, filtered and evaporated. The product was purified by flash chromatography on silica gel (1:1 EtOAc/hexanes) to yield the desired compound (3.2 g).

MS (m/z) 515 (MH$^+$).

Step-4. The above urea (1.48 g) was cyclized with NaOEt (0.215 g) to yield the titled compound (1.1 g). MS (m/z) 483 (MH$^+$).

Example 135

5-(4-Bromobenzyl)-3-(3,5-dichloro-4-hydroxyphenyl)-1,3-diazabicyclo[3.3.0]octane-2,4-dione (Schem 14, step 5)

The compound from Example 134 (0.8 g) was taken in aqueous HBr (10 mL) and the solution was refluxed overnight. The aqueous solution was extracted with EtOAc. The combined organic layers were dried over Na$_2$SO$_4$, filtered and evaporated. The residue was purified by flash chromatography on silica gel (1:1 EtOAc/Hexanes) to yield the titled compound (0.65 g). MS (m/z) 469 (MH$^+$).

Example 136

5-(4-Bromobenzyl)-3-[3,5-dichloro-4-(3-ethoxycarbonylpropyloxy)phenyl]-1,3-diazabicyclo[3.3.0]octane-2,4-dione (Scheme 14, step 6)

Ethyl 4-bromobutyrate (28 mg) was added to a mixture of the compound from Example 135 (55 mg) and K$_2$CO$_3$ (18 mg) in 2 mL anhydrous DMF and the resulting mixture was heated at 80° C. for 5 hours. The solution was partitioned between EtOAc/H$_2$O. The combined organic layers were dried over Na$_2$SO$_4$, filtered and concentrated. The residue was purified by preparative TLC to yield the titled compound (61 mg).

MS (m/z) 583 (MH$^+$).

Example 137

5-(4-Bromobenzyl)-3-[3,5-dichloro-4-(3-carboxypropyloxy)phenyl]-1,3-diazabicyclo[3.3.0]octane-2,4-dione (Scheme 14, step 7, 8)

LiOH (15 mg) was added to a solution of the compound from Example 136 (30 mg) in anhydrous DMF (1 mL) and the reaction mixture was stirred at room temperature for overnight. The solution was partitioned with EtOAc/H₂O. The combined organic layers were dried over Na₂SO₄, filtered and concentrated to dryness to give the diacid. MS (m/Z) 573 (MH⁺).

The dried diacid was taken in SOCl₂ (1 mL) and the solution was heated to reflux for 1 hour. SOCl₂ was evaporated. The residue was partitioned between EtOAc/1N HCl. The combined organic layers were dried over Na₂SO₄, filtered and evaporated. The residue was purified by preparative TLC (1:1 EtOAc/Hexanes) to give the titled compound. MS (m/z) 555 (MH⁺).

Example 138

5-(4-Bromobenzyl)-3-[3,5-dichloro-4-(benzyloxy)phenyl]-1,3-diazabicyclo[3.3.0]octane-2,4-dione

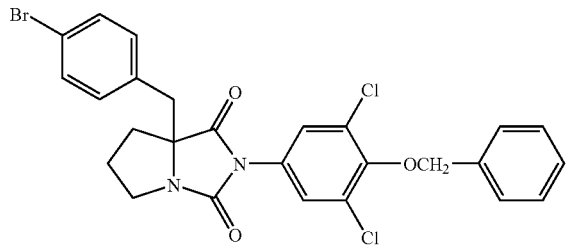

This compound was synthesized from Example 135 in a manner analogous to Example 136. MS (m/z) 559 (MH⁺); mp.62° C.

Example 139

5-(4-Cyanobenzyl)-3-(3,5-dichloro-4-methoxyphenyl)-1,3-diazabicyclo[3.3.0]octane-2,4-dione

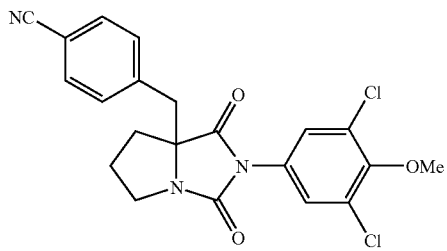

The titled compound was prepared in a manner similar to Example 134. MS m/z 430 (MH⁺). mp. 95.1° C.

Example 140

5-(4-Bromobenzyl)-3-[3,5-dichloro-4-(5-ethoxycarbonylpentyloxy)phenyl]-1,3-diazabicyclo[3.3.0]octane-2,4-dione

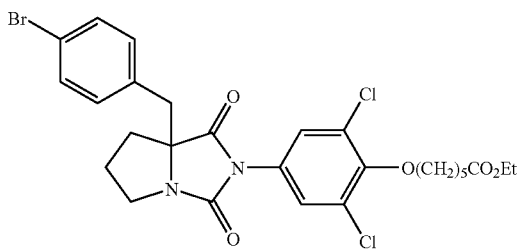

This compound was prepared in a manner similar to Example 136. MS m/z 612 (MH⁺).

Example 141

5-(4-Bromobenzyl)-3-[3,5-chloro-4-(5-carbxypentyloxy)phenyl]-1,3-diazabicyclo[3.3.0]octane-2,4-dione

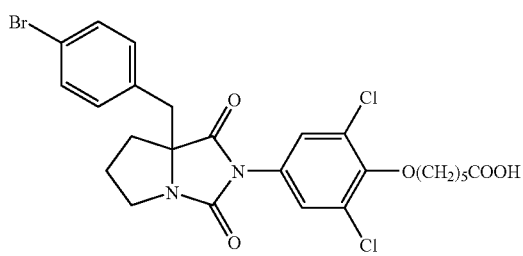

This compound was prepared in a manner similar to Example 137. MS m/z 584 (MH⁺).

Example 142

5-(4-Methoxycarbonylbenzyl)-3-(3,5-dichloro-4-hydroxyphenyl)-1,3-diazabicyclo[3.3.0]octane-2,4-dione

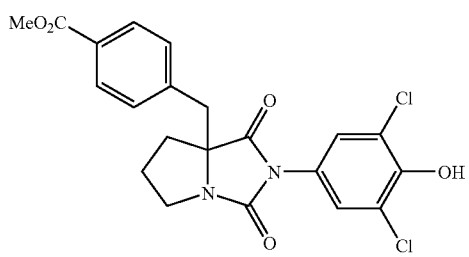

A mixture of the compound from Example 139 (20 mg) and aqueous HBr (5 mL) was heated under reflux for 40 minutes. EtOAc was added and the organic layer was separated. The aqueous layer was extracted with EtOAC. The combined organic layers were dried over Na₂SO₄, filtered and evaporated. The residue was purified by preparative TLC (EtOAc). The obtained material was dissolved in MeOH (2 mL) and few drops of SOCl₂ were added. The reaction mixture was heated under reflux for 1 hour. The residue was partitioned between EtOAc and water. The organic layer was dried over Na₂SO₄, filtered and concentrated. The product was purified via preparative TLC. MS m/z 449 (MH⁺). mp. 105.3° C.

Example 143

5-[4-((L)-N²-asparaginocarbonyl)benzyl]-3-(3,5-dichlorophenyl)-1,3-diazabicyclo[3.3.0]octane-2,4-dione t-butyl ester

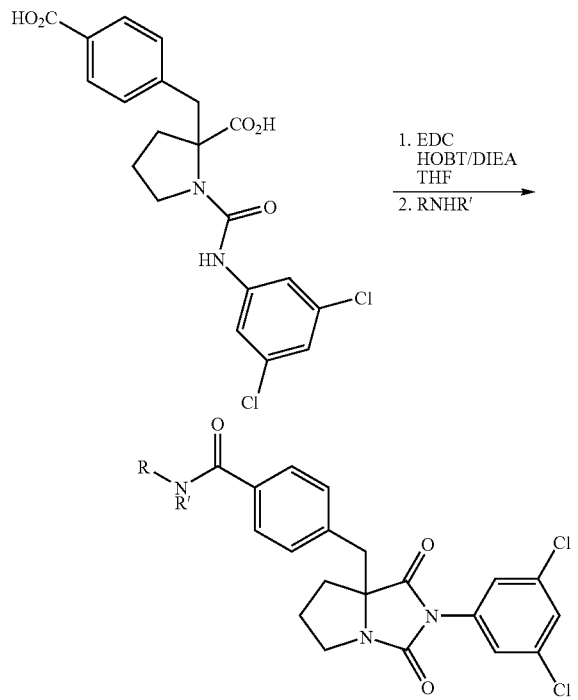

To a solution of the diacid-urea (compound from Example 23, step-1, 145.1 mg) in THF (10 mL) and DMF (1 mL) was added EDC (193 mg), HOBT (130 mg) and N,N-diisopropylethylamine (300 µL). Upon stirring under Ar at room temperature for 8 hours, L-asparagine tert-butyl ester (116 mg) was added. Stirring continued overnight. The solution was partitioned between EtOAc/HCl (0.5 N). The EtOAc layer was separated and washed successively with water, NaHCO₃ (saturated), and brine. It was dried over Na₂SO₄, filtered and concentrated. The residue was purified by chromatography (SiO₂, hexanes/EtOAc gradient elution) to provide the titled compound (177.8 mg). MS m/z 589 (MH⁺). mp. 144.2° C.

The following compounds were prepared in an analogous manner. The free acids were obtained via TFA deprotection of the t-butyl esters.

TABLE 7

| Example | R | Physicochemical Properties |
| --- | --- | --- |
| 144 | —CONHC*H (CH₃) COOtBu (L) | MS m/z 546 (MH⁺) mp. 87.3° C. |
| 145 | —CONHC*H (CH₂Ph) COOtBu (L) | MS m/z 644 (MNa⁺) mp. 78.4° C. |

TABLE 7-continued

| Example | R | Physicochemical Properties |
| --- | --- | --- |
| 146 | —CONHC*H (CH₂COOH) COOH (L) | MS m/z 533 (MH⁺) mp. 183.2° C. |
| 147 | —CONHC*H (CH₃) COOH (L) | MS m/z 490 (MH⁺) mp. 192.1° C. |
| 148 | —CONHC*H (CH₂Ph) COOH (L) | MS m/z 566 (MH⁺) mp. 129.6° C. |
| 149 | —CONH(CH₂)₂—N(morpholine) | MS m/z 531 (MH⁺) mp. 187.6° C. |
| 150 | —CONHCH₂Ph | MS m/z 508 (MH⁺) mp. 128.6° C. |
| 151 | —CON (Me) (CH₂)₂Ph | MS m/z 536 (MH⁺) mp. 202.3° C. |
| 152 | —CONH-CH₂-(2-pyridyl) | MS m/z 509 (MH⁺) mp. 69.7° C. |
| 153 | —CONH-(2-MeO-phenyl) | MS m/z 524 (MH⁺) mp. 103.8° C. |
| 154 | —CONH-(4-Me-3-pyridyl) | MS m/z 509 (MH⁺) |

Example 155

6-(4-Methoxycarbonylbenzyl)-8-(3,5-dichlorophenyl)-1,8-diazabicyclo[4.3.0]nonane-7,9-dione

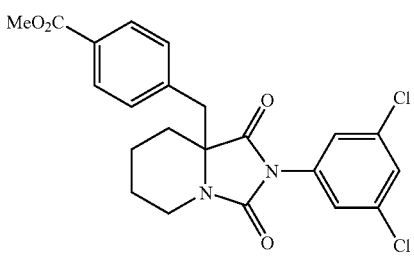

This compound was prepared by a method similar to Example 21 starting from pipecolic acid. MS m/z 447 (MH⁺). mp. 51° C.

The following compounds were prepared starting from Example 155 by following methodology similar to Example 23.

TABLE 8

| Example | R | Physicochemical Properties |
|---|---|---|
| 156 | COOH | MS: m/z 433 (MH+), mp.256.2° C. (dec) |
| 157 | CONHMe | MS: m/z 446 (MH+), mp.78.7° C. (dec) |
| 158 | CONHOH | MS: m/z 448 (MH+), mp.105.6° C. (dec) |

Example 159

6-[4-(4,4-Dimethyl-4,5-dihydro-2-oxazolyl)benzyl]-8-(3,5-dichlorophenyl)-1,8-diazabicyclo[4.3.0]nonane-7,9-dione

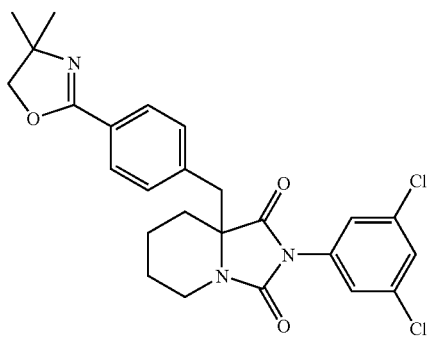

Step-1. Thionyl chloride (2 mL) was added to Example 156 (0.644 g) and the mixture was heated at 100° C. for 2 minutes and stirred overnight at room temperature. The mixture was evaporated and the residue was dried under high vacuum to give the acid chloride. This was used as is for the next step (0.655 g). MS: m/z 451 (MH+).

Step-2. A mixture of the above acid chloride (0.425 g) and 2-amino-2-methyl-1-propanol (0.27 mL) in $CH_2Cl_1$ (5 mL) was stirred at room temperature for 24 hours. The solvent was evaporated and the residue was dried under high vacuum. Thionyl chloride (5 mL) was added and the solution was warmed to 50° C. for 30 minutes. The mixture was evaporated and the residue was purified via HPLC ($CH_3CN$/0.1 N HOAc) to give the desired compound (30 mg). MS: m/z 486 (MH), mp. 87.2° C.

The following compounds (Examples 160-162) were synthesized by following methods similar to Examples 26 and-27.

TABLE 9

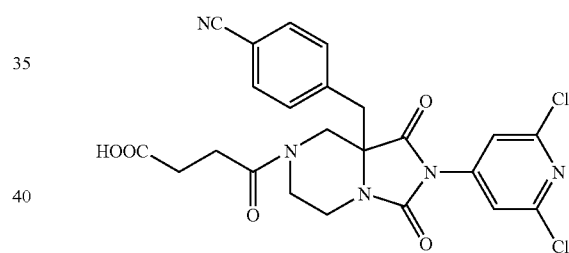

| Example | A | X | Physicochemical Properties |
|---|---|---|---|
| 160 | $CH_2$ | CH | MS 414 (MH+) mp. 57.3° C. |
| 161 | N (COOtBu) | N | MS: m/z 516 (MH+) mp. 80.1° C. (dec) |
| 162 | NH | N | MS: m/z 416 (MH+) mp. 240.6° C. (dec) |

Example 163

6-(4-Cyanobenzyl)-4-(3-carboxypropionyl)-8-(2,6-dichloro-4-pyridyl)-1,4,8-triazabicyclo[4.3.0]nonane-7,9-dione This compound was prepared from Example 162 in a manner similar to Example 64. MS m/z 516 (MH+); mp. 100.9° C. (dec)

The compound from Example 163 was converted to the following compounds in a manner similar to Example 69.

TABLE 10

| Example | A | Physicochemical Properties |
|---|---|---|
| 164 | NCO $(CH_2)_2CONH_2$ | MS m/z 515 (MH+); mp. 79.3° C. (dec) |

TABLE 10-continued

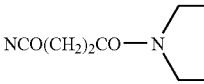

| Example | A | Physicochemical Properties |
|---|---|---|
| 165 | NCO(CH$_2$)$_2$CO—N⌒N—Me | MS m/z 598 (MH$^+$); mp. 165.5° C. (dec) |

Example 166

6-(4-Cyanobenzyl)-4-dimethylaminoacetyl-8-(2,6-dichloro-4-pyridyl)-1,4,8-triazabicyclo[4.3.0]nonane-7,9-dione

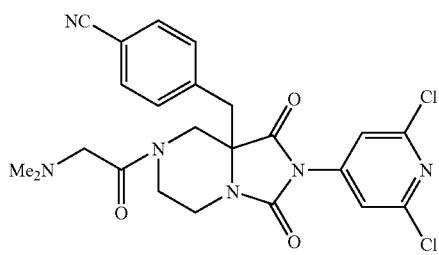

This compound was prepared in a manner similar to Example 31. MS m/z 501 (MH*). HCl salt, mp. 260.8° C. (dec).

Example 167

6-(4-Bromobenzyl)-8-(3,5-dichlorophenyl)-1,8-diaza-4-thiabicyclo[4.3.0]nonane-7,9-dione

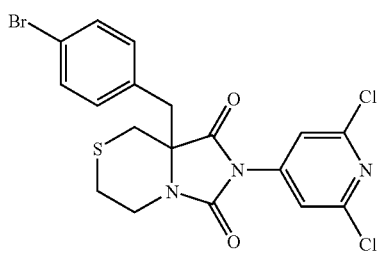

This compound was prepared starting from thiazine 2-carboxylic acid in a manner similar to Example 26.

The following compounds were obtained from Example 167 via oxidation with mCPBA.

TABLE 11

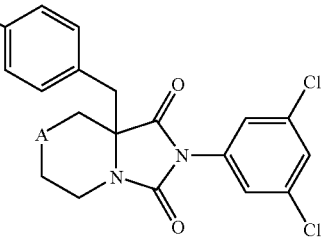

| Example | A | Physicochemical Properties |
|---|---|---|
| 168 | SO | MS m/z 503 (MH$^+$) mp. 208.9° C. (dec) |
| 169 | SO$_2$ | MS m/z 515 (M − H)$^+$ mp. 127.4° C. (dec) |

The compounds in the following tables (Tables 12, 13 and 14) were prepared in a manner similar to Example 21 by following Method B.

TABLE 12

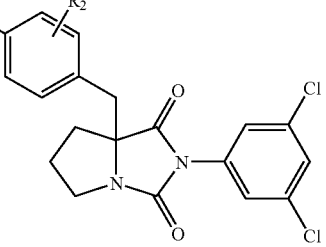

| Examples | R$_1$ | R$_2$ | Physicochemical Properties |
|---|---|---|---|
| 170 | Br | 3-Me | MS m/z 468 (MH$^+$) white foam |
| 171 | H | 3-Br | MS m/z 454 (MH$^+$) white foam |
| 172 | H | 2-Br | MS m/z 454 (MH$^+$) mp. 47.1° C. |
| 173 | Me | H | MS m/z 389 (MH$^+$) mp. 138° C. |
| 174 | CF$_3$ | H | MS m/z 443 (MH$^+$) |
| 175 | CF$_3$ | 2-F | MS m/z 461 (MH$^+$) |
| 176 | CF$_3$ | 3-F | MS m/z 461 (MH$^+$) |
| 177 | OCF$_3$ | H | MS m/z 459 (MH$^+$) |
| 178 | C$_2$H$_5$ | H | MS m/z 403 (MH$^+$) mp. 98.8° C. |
| 179 | SMe | H | MS m/z 421 (MH$^+$) |
| 180 | H | 3-NO$_2$ | MS m/z 420 (MH$^+$) |
| 181 | NH$_2$ | H | MS m/z 390 (MH$^+$) mp. 75.3° C. |
| 182 | —NHCONH—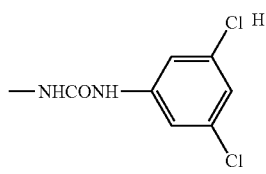 | H | MS m/z 578 (MH$^+$) mp. 214.5° C. |

TABLE 13

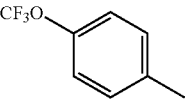

| Example | R | Physicochemical Properties |
|---|---|---|
| 183 | 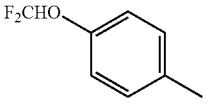 CF₃O— | MS m/z 460 (MH+) mp. 111.4° C. |
| 184 | F₂CHO— | MS m/z 442 (MH+); mp. 120.8° C. |
| 185 | 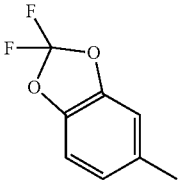 | MS m/z 456 (MH+); mp. 72.8° C. |
| 186 | 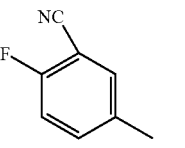 | MS m/z 419 (MH+); mp. 93.7° C. |

TABLE 14

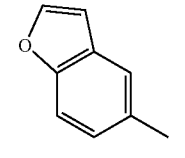

| Example | R | Physicochemical Properties |
|---|---|---|
| 187 | 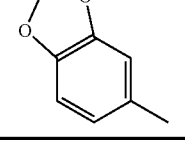 | MS m/z 415 (MH⁺) |
| 188 |  | MS m/z 419 (MH⁺) |

Example 189

5-(4-Methylsulfinylbenzyl)-3-(3,5-dichlorophenyl)-1,3-diazabicyclo[3.3.0]octane-2,4-dione; and

Example 190

5-(4-Methylsulfonylbenzyl)-3-(3,5-dichlorophenyl)-1,3-diazabicyclo[3.3.0]octane-2,4-dione.

MCPBA (95 mg) was added to a solution of Example 179 (0.15 g) in CH₂Cl₂ (10 mL) and the solution was stirred for 15 hours at room temperature. EtOAc was added and the combined solution was washed successively with saturated NaHCO₃, water and brine. The solution was dried and evaporated. The residue was purified via HPLC to yield the titled compounds.

TABLE 15

| Example | R | Physicochemical Properties |
|---|---|---|
| 189 | SOMe | MS m/z 438 (MH⁺) mp. 71.2° C. |
| 190 | SO₂Me | MS m/z 454 (MH⁺) mp. 80.3° C. |

The following compounds were prepared in a manner similar to Example 56, step 4.

TABLE 16

| Example | R | X | Physicochemical properties |
|---|---|---|---|
| 191 | 4-pyridyl | N | MS m/z 377 (MH⁺) mp. 141.4° C. |
| 192 | 2-Me-thiazol-4-yl | N | MS m/z 397 (MH⁺) |
| 193 | 2-naphthyl | CH | MS m/z 425 (MH⁺) mp. 134.6° C. |

TABLE 16-continued

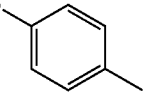

| Example | R | X | Physicochemical properties |
|---|---|---|---|
| 194 | 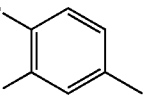 MeO- | N | MS m/z 406 (MH+) mp. 127.3° C. |
| 195 | 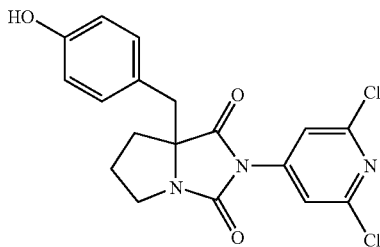 MeO-, NC- | N | MS m/z 431 (MH+) |

Example 196

5-(4-Hydroxybenzyl)-3-(2,6-dichloro-4-pyridyl)-1,3-diazabicyclo[3.3.0]octane-2,4-dione

A solution of BBr$_3$ in CH$_2$Cl$_2$ (1 M, 8 mL) was added dropwise to an ice-cold solution of the compound from Example 194 (1.10 g) in CH$_2$Cl$_2$ (30 mL) with stirring. The slurry was stirred at 0° C. for 30 minutes and at room temperature for an additional 30 minutes. The reaction mixture was quenched with water and diluted with EtOAc. The solution was washed successively with water, saturated NH$_4$Cl, brine, dried and evaporated to give the desired product (0.96 g). mp. 164.9° C. ; MS m/z 393 (MH+).

Example 197

5-(3-Cyano-4-hydroxybenzyl)-3-(2,6-dichloro-4-pyridyl)-1,3-diazabicyclo[3.3.0]octane-2,4-dione

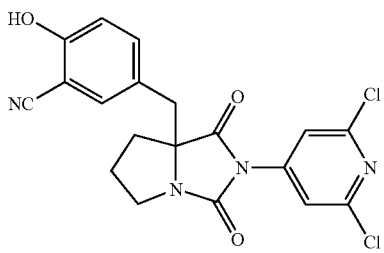

This compound was prepared in a manner similar to Example 196 from the compound of Example 195. MS. 417 (MH+). mp. 113.5° C.

Example 198

5-[4-[2-(4-Pyridyl)ethoxy]benzyl]-3-(2,6-dichloro-4-pyridyl)-1,3-diazabicyclo[3.3.0]octane-2,4-dione

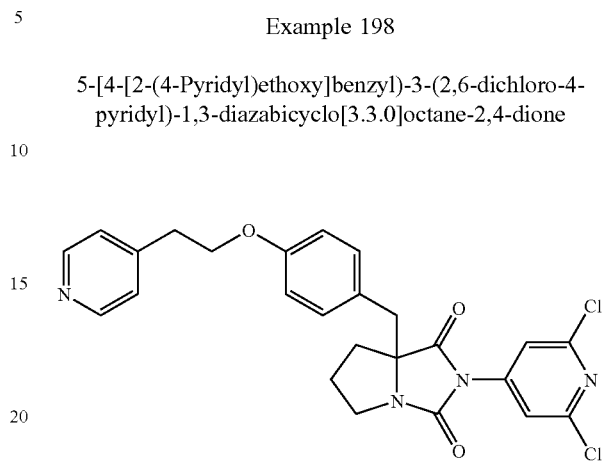

To a mixture of the compound from Example 196 (0.15 g), Ph$_3$P (0.22 g) and 4-hydroxyethylpyridine ((0.070 mL) in anhydrous CH$_2$Cl$_2$ (3 mL) was added DEAD (0.15 mL) under N$_2$. After 30 minutes the reaction mixture was concentrated and the residue was purified via HPLC to give the desired compound (97 mg). MS m/z 498(MH+).

The following compounds were prepared in a manner similar to Example 198 by using requisite hydroxy compounds.

TABLE 17

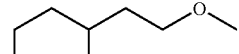

| Example | R | Physicochemical properties |
|---|---|---|
| 199 | 2-pyridyl-CH$_2$CH$_2$-O- | MS m/z 497 (MH+) |
| 200 | 4-piperidyl-CH$_2$CH$_2$-O- | MS m/z 503 (MH+) |
| 201 | Me$_2$N(CH$_2$)$_2$O— | MS m/z 463 (MH+) |
| 202 | CH$_3$CH$_2$O— | MS m/z 420 (MH+) |
| 203 | CH$_3$(CH$_2$)$_2$O— | MS m/z 434 (MH+) |

Example 204

5-(4-i-Propoxybenzyl)-3-(2,6-dichloro-4-pyridyl)-1,3-diazabicyclo[3.3.0]octane-2,4-dione

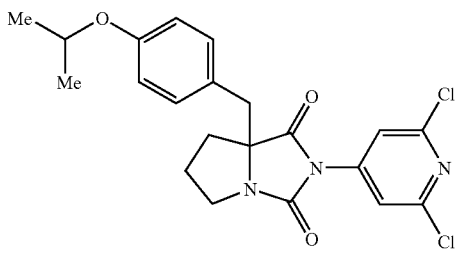

2-Iodopropane (0.5 ml) was added to a suspension of Example 196 (0.17 g) and $Cs_2CO_3$ (0.28 g) in DMF (3 mL) and the mixture was stirred for 4 hours. The mixture was diluted with citric acid and the solution was extracted with EtOAc. EtOAc layer was washed with water and brine, dried and evaporated. The residue was purified via HPLC to yield the titled compound (0.13 g). MS m/z 435(MH$^+$).

Example 205

5-(4-i-Butoxybenzyl)-3-(2,6-dichloro-4-pyridyl)-1,3-diazabicyclo[3.3.0]octane-2,4-dione

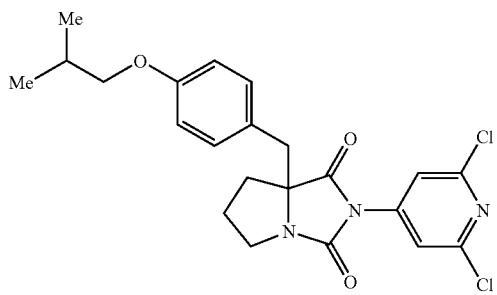

This compound was prepared in an analogous manner to Example 204. MS m/z 447(MH$^+$).

Example 206

5-(4-Ethoxy-3-fluorobenzyl)-3-(2,6-dichloro-4-pyridyl)-1,3-diazabicyclo[3.3.0]octane-2,4-dione

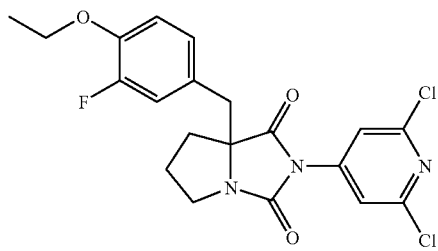

To a solution of the compound from Example 202 (0.24 g) in $CH_3CN$ (15 mL) was added 3,5-dichloro-1-fluoropyridinium triflate (0.38 g) and the mixture was refluxed for 30 hours. The mixture was concentrated and purified by HPLC to give the desired compound (0.094 g). MS m/z 438 (MH$^+$).

The following compounds were prepared in a manner (Suzuki coupling method) similar to Example 7.

TABLE 18

| Example | R$_1$ | R$_2$ | X | Physicochemical properties |
|---|---|---|---|---|
| 207 | phenyl | H | CH | MS m/z 451 (MH$^+$) mp. 57.2° C. |
| 208 | 3,4-dimethylisoxazol-5-yl | H | CH | MS m/z 470 (MH$^+$) |
| 209 | 2-methoxyphenyl | H | CH | MS m/z 481 (MH$^+$) mp. 64° C. |
| 210 | 3-methoxyphenyl (MeO) | H | CH | MS m/z 481 (MH$^+$) mp. 165.2° C. |
| 211 | 3-formylphenyl (OHC) | H | CH | MS m/z 479 (MH$^+$) mp. 220° C. (dec) |
| 212 | 3-cyanophenyl (NC) | H | CH | MS m/z 476 (MH$^+$) mp. 210° C. (dec) |
| 213 | 3-acetylphenyl (COMe) | H | CH | MS m/z 493 (MH$^+$) mp. 80.5° C. |
| 214 | 4-formylphenyl (OHC) | H | CH | MS m/z 479 (MH$^+$) mp. 82.5° C. |
| 215 | 4-cyanophenyl (NC) | H | CH | MS m/z 476 (MH$^+$) mp. 89° C. |

TABLE 18-continued

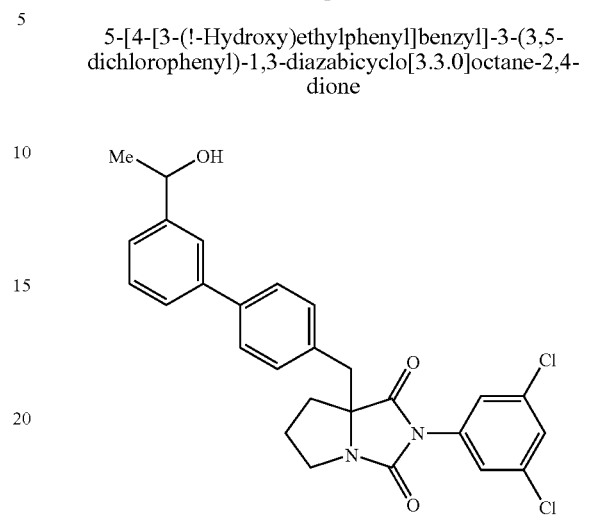

| Example | R₁ | R₂ | X | Physicochemical properties |
|---|---|---|---|---|
| 216 | ![ketone] | H | CH | MS m/z 494 (MH⁺) mp. 68.1° C. |
| 217 | ![3-methylthiophene] | H | CH | MS m/z 457 (MH⁺) mp. 60.5° C. |
| 218 | ![2-methylbenzothiophene] | H | CH | MS m/z 507 (MH⁺) mp. 100.6° C. |
| 219 | ![2-methyl-CN-phenyl] | H | N | MS m/z 477 (MH⁺) mp. 154.3° C. |
| 220 | ![H₂N-methylphenyl] | H | CH | MS m/z 466 (MH⁺) mp. 122.4° C. |
| 221 | ![2-methylthiophene] | H | CH | MS m/z 457 (MH⁺) mp. 83.1° C. |

Example 222

5-[4-(3-Hydroxymethylphenyl)benzyl]-3-(3,5-dichlorophenyl)-1,3-diazabicyclo[3.3.0]octane-l2,4-dione

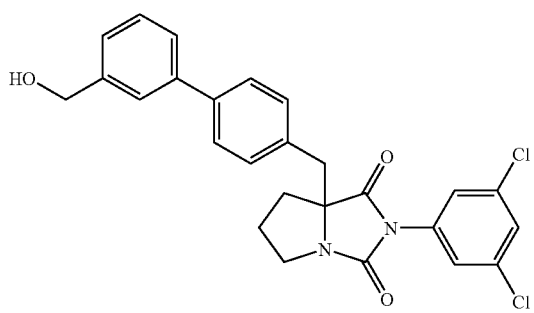

This compound was prepared in a manner similar to Example 12. MS in/z 481 (MH⁺). mp. 77.1° C.

Example 223

5-[4-[3-(!-Hydroxy)ethylphenyl]benzyl]-3-(3,5-dichlorophenyl)-1,3-diazabicyclo[3.3.0]octane-2,4-dione

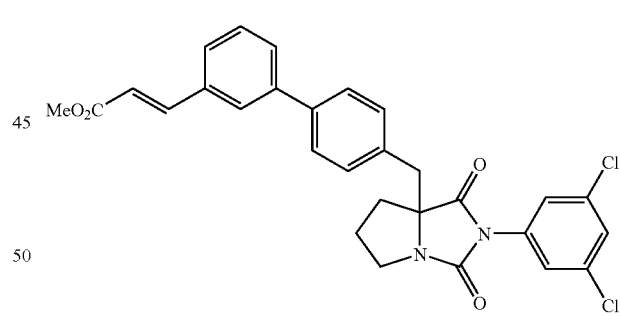

MeMgBr (1.4 M in THF, 0.7 mL) was added to a solution of the compound from Example 211 (0.4 g) in THF (10 mL) at −40° C. and the solution was stirred for 30 minutes. The reaction mixture was warmed to 0° C. and quenched with 1N HCl and extracted with EtOAc. The EtOAc layer was washed with brine, dried (MgSO₄) and evaporated. The residue was purified by chromatography (silica gel; hexanes to 50% EtOAc/hexanes; Chromatotron) and HPLC (CH₃CN/0.1 M HOAc) to give the desired compound (0.3 q). MS: m/z 517 (MNa⁺), mp. 66.5° C.

Example 224

(E)-5-[4-[3-(2-Methoxycarbonyl)vinylphenyl]benzyl]-3-(3,5-dichlorophenyl)-1,3-diazabicyclo[3.3.0]octane-2,4-dione This compound was prepared in a manner similar to Example 17. t-IS m/z 535 (MH⁺). mp. 71.3° C.

Examples 225 and 226 were prepared in accordance with the following scheme (Scheme 15).

Scheme 15:

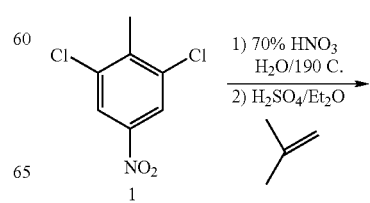

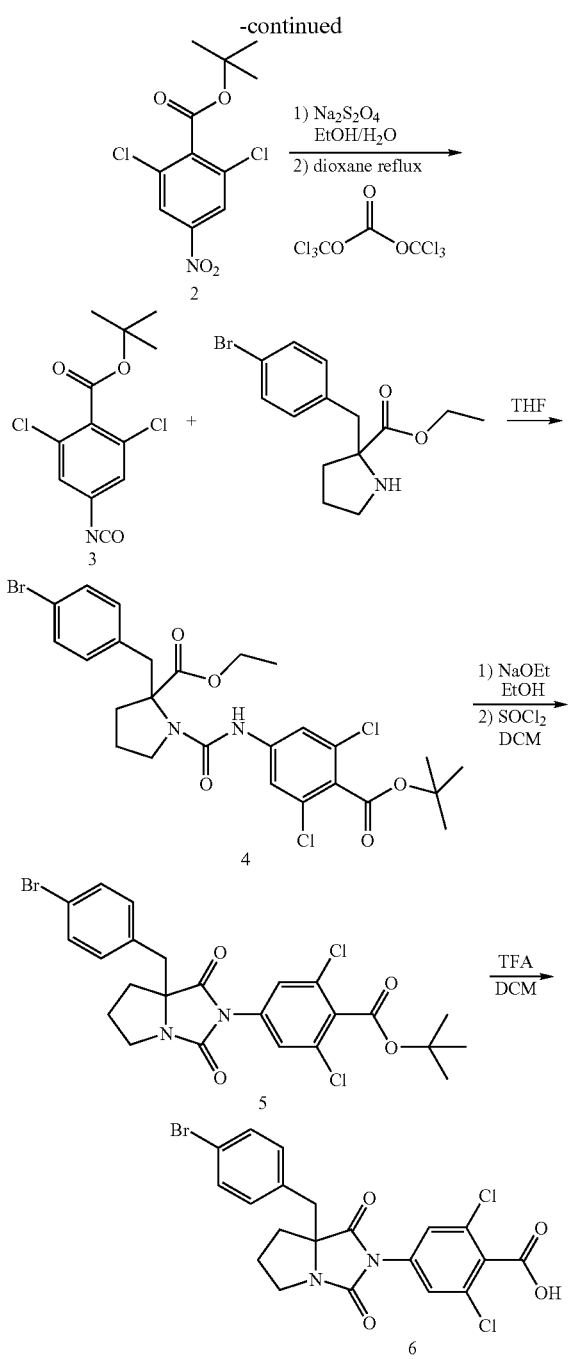

NaHCO₃ solution. The aqueous layer was separated, acidified and re-extracted with EtOAc. It was dried (MgSO₄), filtered, concentrated and dried under high vacuum to yield the desired acid (9.9 g). MS m/z 236 (MH⁺). H₂SO₄ (2 mL) was added to a solution of the above acid (6.21 g) in Et₂O (20 mL). Isobutylene (5 mL) was condensed at −20° C. and added to the above solution. The mixture was placed in a steel bomb and stirred overnight. The bomb was opened and the mixture was taken up in Et₂O (100 mL). It was washed with 1 N NaOH (100 mL). The organic layer was dried (MgSO₄), filtered and evaporated to give the desired ester (6.21 g).

Step 2. The above nitro-ester (5.43 g) was reduced to the corresponding aniline (3.87 g) as described in the Example 131, step-2. ESMS: m/z 262 (MH⁺) A solution of the above amine (2.25 g) and triphosgene (2.6 g) in 20 mL dioxane was refluxed for 24 hours. The solvent was evaporated and the residue was used for next step without further purification.

Step 3. The above isocyanate (2.47 g) was added to an ice-cold solution of the proline derivative (2.23 g) in 50 mL THF. The resulting solution was stirred at 0° C. for 30 minutes and then allowed to warm up to room temperature and stirred overnight. The reaction mixture was partitioned between EtOAc/H₂O. The combined organic layers were dried over Na₂SO₄, filtered and evaporated. The product was purified by chromatography (silica gel, 1:1 EtOAc/hexanes) to yield the desired compound (2.46 g). ESMS: m/z 600 (MH⁺).

Step 4. The above urea (0.5 g) was hydrolyzed with NaOEt (0.06 g) in EtOH at room temperature to yield the desired acid (0.5 g). ESMS: m/z 572 (MH⁺). SOCl₂ was added to a slurry of the acid (0.092 g) in CH₂Cl₂ (10 mL) and the mixture was stirred overnight at room temperature. The mixture was evaporated and the residue was purified by chromatography (silica gel; 3/2 hexane/EtOAc; Chromatotron) to yield the titled compound (0.09 g). MS m/z 554 (MH⁺); mp. 109-110° C.

Example 226

5-(4-Bromobenzyl)-3-(3,5-dichloro-4-carboxyphenyl)-1,3-diazabicyclo[3.3.0]octane-2,4-dione (Scheme 15, compound 6)

The compound from Example 225 was deprotected with TFA/CH₂Cl₂ to give the titled acid. MS m/z 492 (MH⁺); mp. 152° C.

Example 227

5-(4-Bromobenzyl)-3-[3,5-dichloro-4-(carboxymethylcarbamoyl) phenyl]-1,3-diazabicyclo[3.3.0]octane-2,4-dione

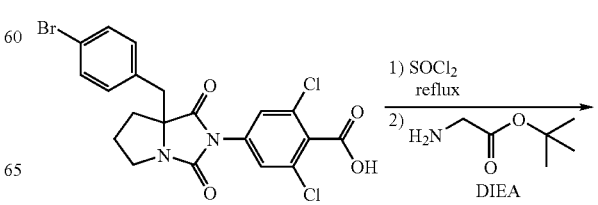

Example 225

5-(4-Bromobenzyl)-3-[3,5-dichloro-4-(t-butoxycarbonyl)phenyl]-1,3-diazabicyclo[3.3.0]octane-2,4-dione (Scheme 15, compound 5)

Step 1. A mixture of 2,6-dichloro-4-nitrotoluene (10 g), 70% HNO₃ (18 mL) and water (20 mL) was sealed in a steel bomb and heated with stirring in a sand bath at 195° C. for 24 hours. Additional HNO₃ (2 mL) was added and the mixture was reheated at 195° C. for 19 hours. The mixture was extracted with EtOAc and slowly treated with saturated -continued

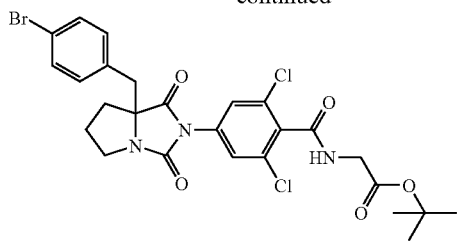

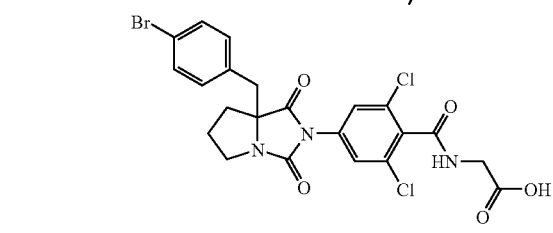

Step-1. A mixture of the compound from Example 226, SOCl₂ and a few drops of water was heated under reflux for 3 days. The mixture was evaporated and dried under high vacuum to give the desired acid chloride, which was used as is for the next step.

Step-2. DIEA (0.13 mL) was added to a solution of glycine t-butyl ester hydrochloride (0.035 g) in THF (3 mL). To this solution was added a solution of the above acid chloride (0.061 g) in THF (2 mL) and the mixture was stirred overnight at room temperature. THF was evaporated and the residue was diluted with EtOAc. The solution was washed successively with 1N HCl, brine and water. It was dried (MgSO₄), filtered and concentrated to an oil which was purified via chromatography (silica gel; 3/2 hexanes/EtOAc; Chromatotron) to give the desired amide (0.061 g). MS m/z 611 (MH⁺).

Step-3. The above ester was dissolved in a mixture of TFA (1 mL) and CH₂Cl₂ (1 mL) and the solution stirred at room temperature for 4 hours. It was concentrated and the residue purified via chromatography (silica gel; CHCl₃-CHCl₃/MeOH 10%) to give the titled compound (0.045 g). MS m/z 555 (MH⁺), mp. 157-158° C.

The following examples were prepared in a similar manner using requisite amino acid derivatives.

Example 228

5-(4-Bromobenzyl)-3-(3,5-dichloro-4-L-alaninocarbonyl)-1,3-diazabicyclo[3.3.0]octane-2,4-dione

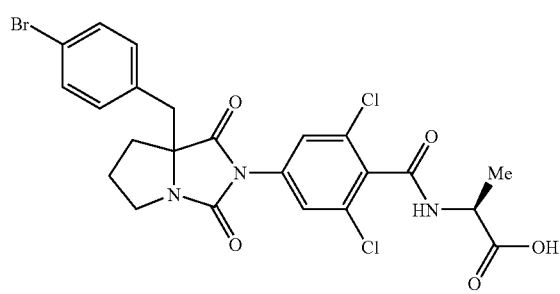

MS m/z 569 (MH⁺); mp. 203° C.

Example 229

5-(4-Bromobenzyl)-3-(3,5-dichloro-4-L-asparaginocarbonylphenyl)-1,3-diazabicyclo[3.3.0]octane-2,4-dione

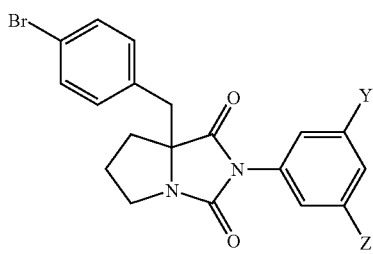

MS m/z 612 (MH⁺); mp. 172° C.

The following compounds were prepared in a manner similar to Example 1 with the exception of the use of LDA in place of KHMDS in step-1.

TABLE 19

| Example | Y | Z | Physicochemical Properties |
|---------|-----|-----|---------------------------|
| 230 | Cl | H | MS (m/z) 419 [MH⁺]. mp 66° C. |
| 231 | SMe | H | MS (m/z) 431 [MH⁺]. mp 84.8° C. |
| 232 | CF₃ | CF₃ | MS (m/z) 521 [MH⁺]. mp 138.0° C. |
| 233 | CF₃ | H | MS (m/z) 453 [MH⁺]. mp 82.6° C. |
| 234 | CN | H | MS (m/z) 410 [MH⁺]. mp 241.0° C. |
| 235 | OMe | OMe | MS (m/z) 445 [MH⁺]. mp 154.8° C. |
| 236 | CO₂H | CO₂H | MS (m/z) 473 [MH⁺]. mp 259° C. (dec) |
| 237 | COMe | H | MS (m/z) 427 [MH⁺]. mp 120.4° C. |
| 238 | F | H | MS (m/z) 403 [MH⁺]. mp 120.9° C. |

Example 239

5-(3-Nitrobenzyl)-3-(2,6-dichloro-4-pyridyl)-1,3-diazacyclo[3.3.0]octane-2,4-dione

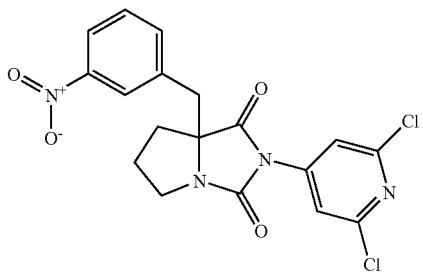

This compound was prepared in an analogous manner. MS m/z 421 (MH$^+$); mp. 182.8° C.

Example 240

5-(4-Cyanobenzyl)-3-(2-amino-3,5-dichlorophenyl)-1,3-diazabicyclo[3.3.0]octane-2,4-dione

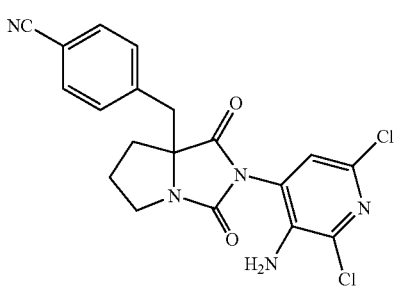

This compound was prepared in a manner similar to Examples 131 and 132 starting from 2,4-dichloro-6-nitroaniline. MS m/z 415 (MH$^+$). mp. 122.2° C.

The following compounds were prepared in a manner similar to Example 67 using the requisite acid.

TABLE 20

| | | | Physicochemical Data | |
|---|---|---|---|---|
| Example | diastereomer | R | mp ° C. | MS (m/z) |
| 241 | 5R, 7S | H₃C-isoxazole-C(=O)NH— | 124.8 | 584 [MH$^+$] |
| 242 | 5R, 7S | 5-methylisoxazole-4-C(=O)NH— | 155.8 | 584 [MH$^+$] |
| 243 | 5R, 7S | pyridine-3-C(=O)NH— | 253 | 580 [MH$^+$] |
| 244 | 5R, 7S | BocNHCH$_2$CONH— | foam | 654 [MNa$^+$] |
| 245 | 5R, 7S | H$_2$N-C(=O)-CH$_2$CH$_2$-C(=O)-NH— | 125.5 | 585 [MNa$^+$] |
| 246 | 5R, 7S | cyclopropyl-C(=O)NH— | 178 | 543 [MH$^+$] |
| 247 | 5R, 7S | thiophene-2-C(=O)NH— | Dec | 585 [MNa$^+$] |
| 248 | 5R, 7S | thiophene-3-C(=O)NH— | 190.8 | 585 [MH$^+$] |
| 249 | 5R, 7S | H$_2$N-C(=O)-CH(NHBoc)-CH$_2$-C(=O)-NH— | | 689 [MH$^+$] |

Example 250

(5R, 7S)-5-[4-(Trifluoromethoxy)benzyl]-3-(2,6-dichloro-4-pyridyl)-7-methoxycarbonylamino-1,3-diazabicyclo[3.3.0]octane-2,4-dione To a solution of the compound from Example 63 (0.075 g) in THF (4 mL) was added DIEA (0.10 mL) and methyl chloroformate (0.020 mL). After 3 hours, the reaction was concentrated and purified by chromatography (silica gel; 98:2 CH$_2$Cl$_2$/methanol, Chromatotron) to afford the titled compound (0.0715 g): MS (m/z) 533 [MH$^+$]. mp 119.8° C.

Example 251

(5R, 7S)-5-[4-(Trifluoromethoxy)benzyl]-3-(2,6-dichloro-4-pyridyl)-7-(1-pyrrolyl)-1,3-diazabicyclo[3.3.0]octane-2,4-dione

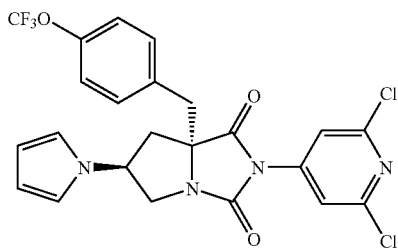

To a solution of the compound from Example 63 (0.25 g) in acetic acid (5 mL) was added sodium acetate (0.26 g) and 2,5-dimethoxyfuran (0.14 mL). After 20 minutes at reflux, the reaction was cooled, diluted with EtOAc, neutralized with solid $NaHCO_3$. The organic solution was collected, washed with saturated $NaHCO_3$ and brine, dried ($Na_2SO_4$), filtered, concentrated and purified by chromatography (silica gel; 95:5 $CH_2Cl_2$/methanol, Chromatotron) to afford the titled compound (0.145 g): MS (m/z) 525 [MH+]. mp 129.5° C.

Example 252

(5R, 7S)-5-[4-(Trifluoromethoxy)benzyl]-3-(2,6-dichloro-4-pyridyl)-7-aminoacetylamino-1,3-diazabicyclo[3.3.0]octane-2,4-dione The titled compound was prepared from Example 244 by treatment with TFA in the usual manner. MS (m/z) 532 [MH+]. mp 114° C.

Example 253

(5R, 7S)-5-[4-(Trifluoromethoxy)benzyl]-3-(2,6-dichloro-4-pyridyl)-7-[(methansulfonylaminoacetyl)amino]-1,3-diazabicyclo[3.3.0]octane-2,4-dione The titled compound was prepared from Example 252 in a manner similar to Example 33: MS (m/z) 632 [MNa+]. mp 104.9° C.

Example 254

(5R, 7S)-5-[4-(Trifluoromethoxy)benzyl]-3-(2,6-dichloro-4-pyridyl)-7-methanesulfonylamino-1,3-diazabicyclo[3.3.0]octane-2,4-dione The titled compound was prepared from the compound from Example 63 in a manner similar to Example 33: MS (m/z) 575 [MNa+]. mp 207.2° C.

Example 255

(5R, 7S)-5-[4-(Trifluoromethoxy)benzyl]-3-(2,6-dichloro-4-pyridyl)-7-[(3-carbamoyl-3-aminopropanoyl)amino]-1,3-diazabicyclo[3.3.0]octane-2,4-dione The titled compound was prepared from Example 249 by treatment with TFA in usual manner: MS (m/z) 589 [MH+]. mp 107.8° C.

Example 256

(5R, 7S)-5-[4-(Trifluoromethoxy)benzyl]-3-(2,6-dichloro-4-pyridyl)-7-[(3-carbamoyl-3-acetylaminopropanoyl)amino]-1,3-diazabicyclo[3.3.0]octane-2,4-dione The titled compound was prepared from Example 255 in a manner similar to Example 48. MS (m/z) 653 [MNa+]. mp 152.8° C.

Example 257

(5R, 7R)-5-[4-(Trifluoromethoxy)benzyl]-3-(2,6-dichloro-4-pyridyl)-7-dimethylcarbamoyl-1,3-diazabicyclo[3.3.0]octane-2,4-dione

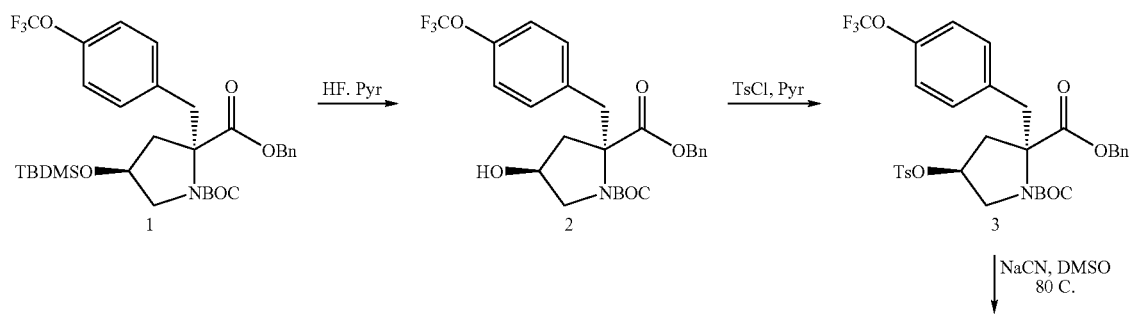

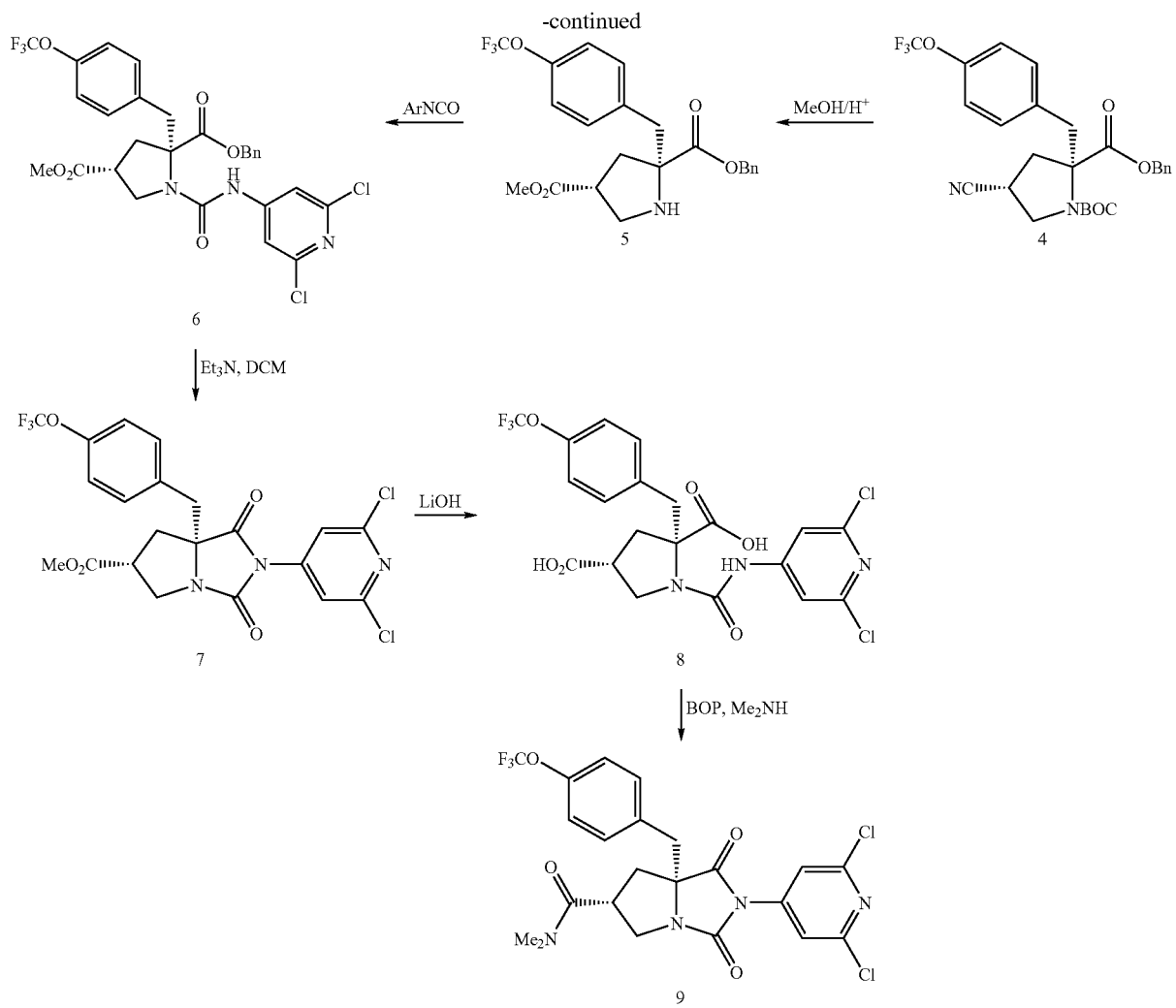

Step 1. The mixture of diastereoisomers of structure 1 (5.5g) were dissolved in THF (150 mL) and HF pyridine (10 mL) was added. The reaction mixture was stirred at room temperature for 1 hour whereupon saturated NaHCO$_3$ was added until no further effervescence. The aqueous phase was then separated and extracted with EtOAc. The combined organics were washed with HCl (5%), saturated NaHCO$_3$, then dried over Na$_2$SO$_4$, filtered and concentrated in vacuo. The residue was purified by liquid chromatography (SiO$_2$, EtOAc/Hexane=25/75) gave 2 as a single diastereoisomer (2.9 g). MS (m/z) 496 (MH$^+$).

Step 2. A mixture of the compound 2 (2.9 g), TsCl (2.23 g), pyridine (1.4 mL) and DCM (10 mL) was stirred at room temperature. After 3 days, EtOAc was added and the mixture was washed with HCl (5%). The aqueous phase was then separated and extracted with EtOAc. The combined organics were washed with NaHCO$_3$, then brine, dried over Na$_2$SO$_4$, filtered and concentrated in vacuo. The residue was purified by liquid chromatography (SiO$_2$, EtOAc/Hexane=1/9) to give 3 (3.5 g).

MS (m/z) 650 (MH$^+$)

Step 3. The compound 3 (2.47 g) was dissolved in dry DMSO (8 mL) and powdered NaCN (340 mg) was added. The reaction mixture was heated at 80° C. for 30 hours with more NaCN (2×100 mg) being added at 9 and 22 hours. EtOAc and brine were added and the reaction mixture was shaken. The aqueous phase was then separated and extracted with EtOAc. The combined organics were dried over Na$_2$SO$_4$, filtered and concentrated in vacuo. The residue was purified by liquid chromatography (SiO$_2$, EtOAc/Hexane=1/9) gave 4 (0.9 g). MS (m/z) 504 (MH$^+$).

Step 4. The compound 4 (0.9g) was dissolved in dry MeOH (6 mL) and HCl (1M in Et$_2$O, 12 mL) was added and the reaction mixture was stirred at room temperature. After 18 hours, EtOAc and saturated NaHCO$_3$ were added until no further effervescence. The aqueous phase was then separated and extracted with EtOAc. The combined organics were dried over Na$_2$SO$_4$, filtered and concentrated in vacuo. The residue was purified by liquid chromatography (SiO$_2$, EtOAc/Hexane=3/7) to give 5 (730 mg)

MS (m/z) 438 (MH$^4$).

Step 5. Amine 5 (720 mg) was dissolved in DCM (10 mL) and 3,5-dichloro-4-pyridyl isocyanate (343 mg) was added directly. The mixture was stirred at room temperature for 5 hours whereupon it was concentrated and purified by liquid chromatography (SiO$_2$, EtOAc/Hexane=2/8) to give 6 (900 mg). MS (m/z) 626 (M$^+$)

Step 6. Urea 6 (880 mg) was dissolved in DCM (16 mL) and Et$_3$N (0.59 mL) was added. The reaction mixture was then heated at 43° C. for 18 hours, concentrated in vacuo and purified by liquid chromatography (SiO$_2$, EtOAc/Hexane=2/8) to give 7 (508 mg). MS (m/z) 518 (M$^+$).

Step 7. The compound 7 (280 mg) was dissolved in THF/MeOH and LiOH (50 mg) in H$_2$O (1 mL) was added. The reaction mixture was stirred at room temperature for 24 hours. HCl (5%) was added to pH=2 and the reaction mixture concentrated. The aqueous layer was extracted with EtOAc and DCM and the combined organic layers dried over Na$_2$SO$_4$ and concentrated to give the desired product 8 (305 mg). MS (m/z) 522 (M$^+$).

Step 8. To a solution of the above diacid 8 (53 mg) in dry DCM (2 mL) and diisopropylethylamine (0.044 mL) was added BOP reagent (99 mg) and the solution stirred at room temperature for 2.5 hours. Dimethylamine (2M in THF, 0.066 mL) was then added. After 4 h, further BOP reagent (0.1 mmol) and dimethylamine (0.05 mmol) were added. After a total of 20 hours, EtOAc and HCl (5%) were added and the reaction mixture shaken. The aqueous phase was separated and extracted with EtOAc. The combined organics were washed with saturated NaHCO$_3$, brine, dried over Na$_2$SO$_4$, filtered and concentrated in vacuo. The residue was purified by liquid chromatography (SiO$_2$, EtOAc/DCM=1/9) to give the titled compound (47 mg).

MS (m/z) 531 (M$^+$).

The following compounds were prepared in an analogous manner to Example 257.

TABLE 21

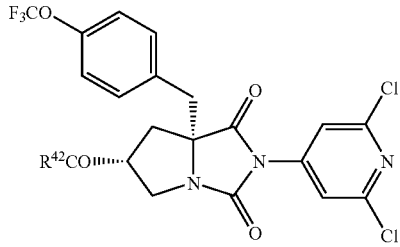

| Example | diastereo-isomer | R$^{41}$ | Physico-chemical Properties |
|---|---|---|---|
| 258 | 5R, 7R | MeNH— | MS (m/z) 517 (M$^+$) mp. 75° C. |
| 259 | 5R, 7R | cyclopropyl-NH— | MS (m/z) 543 (M$^+$) mp. 77° C. |
| 260 | 5R, 7R | morpholino— | MS (m/z) 573 (M$^+$) |
| 261 | 5R, 7R | morpholino-ethyl-NH(Me)— | MS (m/z) 616 (M$^+$) |

TABLE 21-continued

| Example | diastereo-isomer | R$^{41}$ | Physico-chemical Properties |
|---|---|---|---|
| 262 | 5R, 7R | benzyl-N(H)Me | MS (m/z) 593 (M$^+$) |
| 263 | 5R, 7R | thienylmethyl-N(H)Me | MS (m/z) 599 (M$^+$) |
| 264 | 5R, 7R | 2-oxopyrrolidinyl-propyl-N(H)Me | MS (m/z) 626 (M$^+$) |

Example 265

(5R, 7R)-5-[4-(Trifluoromethoxy)benzyl]-3-(2,6-dichloro-4-pyridyl)-7-carbamoyl-1,3-diazabicyclo[3.3.0]octane-2,4-dione

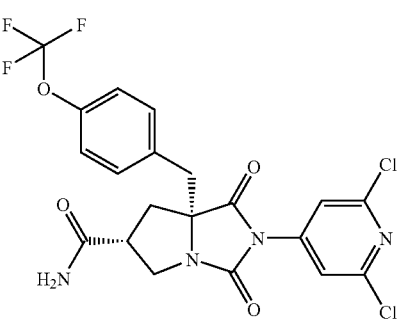

The title compound was prepared in a manner similar to Example 257 but replacing dimethyl amine with ammonium chloride in step 8. MS (m/z) 503 (M$^+$)

Example 266

(5R,7R)-5-benzyl-3-(3,5-dichlorophenyl)-7-hydroxy-1,3-diazabicyclo[3.3.0]octane-2,4-dione

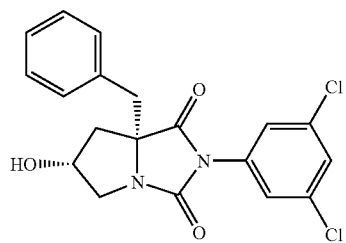

This compound was prepared in a manner similar to the compound described in Example 58. MS (m/z) 391 (MH$^+$)

Example 267

5-Benzyl-3-(3,5-dichlorophenyl-1,3-diazabicyclo[3.3.0]octane-2,4-dione

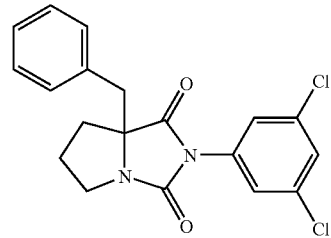

This compound was prepared in a manner similar to the compound described in Example 21. MS (m/z) 375 (MH$^+$); mp. 173.8° C.

Example 268

(5R, 7R)-5-[4-(Trifluoromethoxy)benzyl]-3-(3,5-dichlorophenyl)-7-hydroxy-1,3-diazabicyclo[3.3.0]octane-2,4-dione

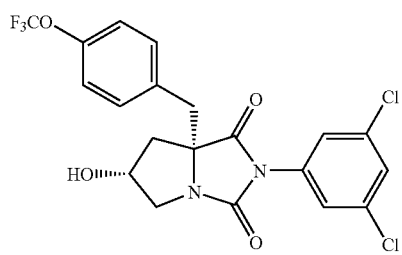

This compound was prepared in a manner similar to the compound described in Example 58. MS (m/z) 475 (MH$^+$); mp. 50.4° C.

Example 269

6-Bromobenzyl-8-(2,6-dichloro-4-pyridyl)-1,4,8-triazabicyclo[4.3.0]nonane-3,7,9-trione.

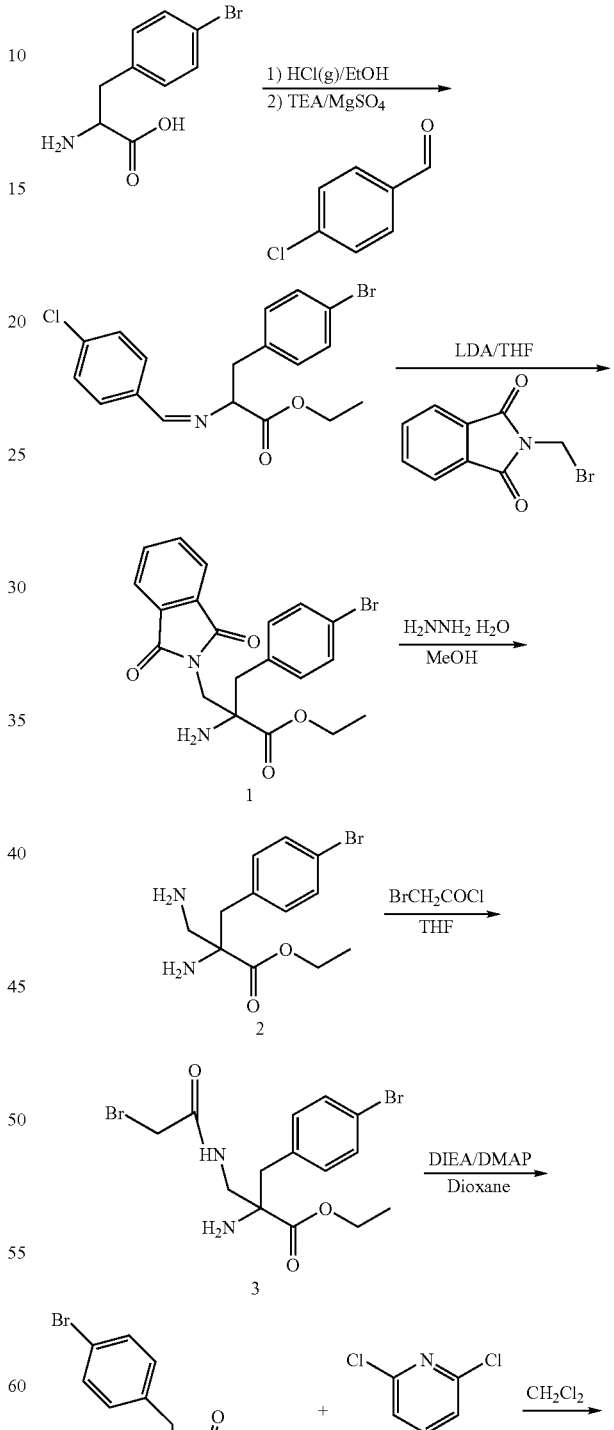

-continued

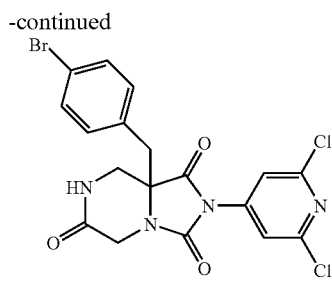

Steps 1 and 2. Compound 1 was prepared from 4-brmophenylalanine ethyl ester according to the methodology described in WO 98/39303. MS(m/z): 431(MH$^+$).

Step 3. A mixture of the compound 1 and hydrazine hydrate in MeOH was heated under reflux for 24 hours. MeOH was evaporated and the compound was purified via chromatography to give the diamine. MS(m/z): 301(MH$^+$).

Steps 4 and 5. THF (15 mL) was added to the above diamine (1.1 g) and the solution was cooled in ice. Bromoacetyl chloride (0.35 mL) was added dropwise and the solution was warmed slowly to room temperature. The mixture was stirred for hours and concentrated to half the volume. Et$_2$O was added and the mixture stirred at room temperature until precipitation was complete. The solid was filtered and dissolved in EtOAc. The solution was washed with saturated NaHCO$_3$ followed by brine, dried (MgSO$_4$), filtered and evaporated. The residue (1.09 g) was used as is for the next step.

A mixture of the above compound (0.480 mg), DIEA (0.59 mL) and DMAP (7 mg) in dioxan (20 mL) was heated at 70° C. for 24 hours. The mixture was diluted with EtOAc/water and the EtOAc layer was separated. The aqueous solution was extracted with EtOAc and the combined organic layer was dried (Na$_2$SO$_4$), filtered and concentrated. The residue was purified via HPLC (AcOH 0.1M/ CH$_3$CN 75/25 to 0/100) to give the desired compound (0.52 mg). MS(m/z): 341(MH$^+$).

Step 6. To a solution of the above compound (50 mg) in dry DCM (2 mL) was added 2,6-dichloropyridyl-4-isocyanate (36 mg) and the solution stirred at room temperature for 5 hours. The solution was concentrated in vacuo and the residue purified by chromatography (silica gel; Chromatotron) to give the titled compound (0.47 mg). mp. 226° C. MS(m/z): 484(MH$^+$).

The following compounds were prepared in a manner similar to one of the above Examples.

TABLE 22

| Example | Diastereomer | R | Method similar to Example | MS m/z (MH$^+$) | mp (° C.) |
|---|---|---|---|---|---|
| 270 | 5R, 7S | —HN-C(O)-(2-pyridyl) | 243 | 580 | 89.1 |
| 271 | 5R, 7S | —HN-C(O)-(3-furyl) | 243 | 569 | 259 |
| 272 | 5R, 7S | —HN-C(O)-(2-furyl) | 243 | 569 | 249 |
| 273 | 5R, 7S | —NH-C(O)-CH$_2$-(3-pyridyl) | 243 | 594 | 92.6 |

TABLE 22-continued

| Example | Diastereomer | R | Method similar to Example | MS m/z (MH+) | mp (° C.) |
|---|---|---|---|---|---|
| 274 | 5R, 7S | —NHCOO(i-Pr) | 250 | 560 | 146.7 |
| 275 | 5R, 7S | —NHCOOPh | 250 | 560 | 146.7 |
| 276 | 5R, 7S | (N-methylcarbamoyl pyrrolidine) | 250 | 572 | 172.7 |
| 277 | 5R, 7S | —HN-C(O)-NH-CH2CH2-Me | 65 | 560 | 146.7 |
| 278 | 5R, 7S | —HN-C(S)-NH-CH2CH2-Me | 65 | 560 | 146.7 |
| 279 | 5R, 7S | —NH-β-Asp(N-Ac)—NH2 | 67 | 631 | 152.8 |
| 280 | 5R, 7S | —NH-β-AspNH2 | 67 | 589 | 107.8 |
| 281 | 5R, 7R | —NH2 | 63 | 475 | 123.5 |
| 282 | 5R, 7R | —NHCO(c-Pr) | 64 | 543 | 136.8 |
| 283 | 5R, 7R | —NHCOMe | 64 | 517 | 122.7 |
| 284 | 5R, 7R | —HN-C(O)-(3-pyridyl) | 243 | 580 | 102.3 |
| 285 | 5R, 7R | (N-methylcarbamoyl pyrrolidine) | 250 | 572 | 86.2 |

Example 286

(5R, 7S)-5-[4-(Trifluoromethoxy)benzyl]-3-(2,6-dichloro-4-pyridyl)-7-valerylamino-1,3-diazabicyclo[3.3.0]octane-2,4-dione Valeryl chloride (0.031g) was added to a solution of the compound from Example 63 (0.1 g) and DIEA (0.84 g) in THF (5 mL) and the reaction mixture was stirred at room temperature for 24 hours. The mixture was concentrated and the residue was purified via HPLC (CH₃CN/0.1 M AcOH) to yield 0.075 g of the titled compound. MS (m/z) 559 (MH+) and 581 (MNa+). mp 66.8° C.

Example 287

(5R, 7S)-5-[4-(Trifluoromethoxy)benzyl]-3-(2,6-dichloro-4-pyridyl)-7-ureido-1,3-diazabicyclo[3.3.0]octane-2,4-dione A solution of the compound from Example 63 (0.114 g) in diethyl ether (5 mL) was added dropwise to a solution of N-chlorosulfonylisocyanate (30 μL) in diethyl ether (5 mL) at −15° C. After 1 hour, the reaction mixture was concentrated.

The residue was stirred with 0.5 N HCl for 30 minutes. The reaction mixture was diluted with DMSO and purified

Example 288

(5R, 7S)-5-[4-(Trifluoromethoxy)benzyl]-3-(2,6-dichloro-4-pyridyl)-7-(2,5-dimethylpyrrolyl)-1,3-diazabicyclo[3.3.0]octane-2,4-dione A mixture of the compound from Example 63 (0.1 g), 2,5-hexanedione (0.028 g), AcOH (5 mL) in EtOH (5 mL) was refluxed for 4 hours. The mixture was concentrated and the residue was purified via HPLC (CH$_3$CN/0.1 M AcOH) to yield 0.065 g of the titled compound. MS (m/z) 553 (MH$^+$). mp 112.4° C.

by HPLC (CH$_3$CN/0.1 M AcOH). The desired fraction was collected, concentrated, neutralized, extracted with EtOAc, dried (Na$_2$SO$_4$), filtered and concentrated to afford the titled compound (0.077 g). MS (m/z) 518 (MH$^+$). mp 141.7° C.

Example 289

(5R, 7S)-5-[4-(Trifluoromethoxy)benzyl]-3-(2,6-dichloro-4-pyridyl)-7-[2-(trifluoroacetyl)pyrrolyl]-1,3-diazabicyclo[3.3.0]octane-2,4-dione To a solution of the compound from Example 251 (0.078 g) in CH$_2$Cl$_2$ (10 mL) was added trifluoroacetic anhydride (0.084 g) and the mixture was stirred under N$_2$ overnight. The reaction mixture was concentrated and the residue was purified via HPLC (CH$_3$CN/0.1 M AcOH) to yield 0.060 g of the titled compound.

MS (m/z) 621 (MH$^+$). mp 166.6° C.

The following compounds (5R,7S diastereomers) were prepared in a manner similar to one of the above Examples.

TABLE 23

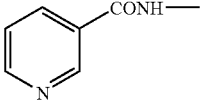

| Example | Diastereomer | R | Method similar to Example | MS m/z (MH$^+$) | mp (° C.) |
|---|---|---|---|---|---|
| 290 | 5R, 7S | N$_3$ | 62 | 500 | |
| 291 | 5R, 7S | AcNH | 64 | 516 | 61.2 |
| 292 | 5R, 7S | cPrCONH | 67 | 542 | 97.6 |
| 293 | 5R, 7S | 3-pyridyl-CONH— | 67 | 579 | 100.5 |
| 294 | 5R, 7S | 6-Me-pyridyl-3-CO— | 67 | 593 | 87.1 |
| 295 | 5R, 7S | pyroglutamyl-NHMe | 67 | 585 | 174.8 |
| 296 | 5R, 7S | H$_2$N-CO-CH$_2$CH$_2$-CONHMe | 67 | 573 | 68.4 |
| 297 | 5R, 7S | 4-Me-piperazinyl-CO-CH$_2$CH$_2$-CONHMe | 67 | 656 | 72.9 |
| 298 | 5R, 7S | EtOCONH | 250 | 546 | 64 |

TABLE 23-continued

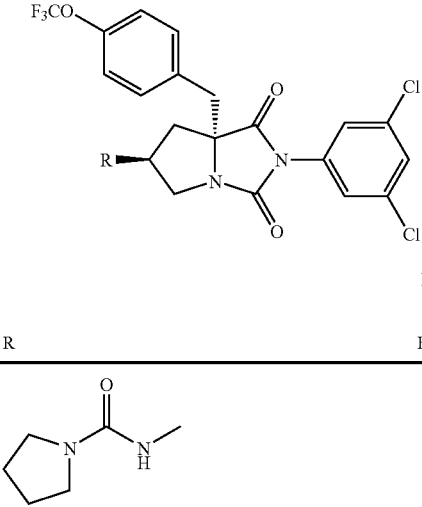

| Example | Diastereomer | R | Method similar to Example | MS m/z (MH+) | mp (° C.) |
|---|---|---|---|---|---|
| 299 | 5R, 7S | (pyrrolidine-N-C(O)-NHMe) | 250 | 571 | 151.2 |

Example 300

(5R, 7S)-5-[4-(Trifluoromethoxy)benzyl]-3-(3,5-dichlorophenyl)-7-amino-1,3-diazabicyclo[3.3.0]octane-2,4-dione Hydrogen (gas) was bubbled through a solution of the compound from Example 288 (0.274 g) in EtOAc (20 mL) in presence of Pd—C (5%, 20 mg) for 10 minutes and the mixture was stirred for 2 hours. The mixture was filtered through celite and the celite washed with additional EtOAc. The combined EtOAc was evaporated and the residue was purified via chromatography (hexanes-EtOAc) to yield 0.161 g of the titled compound. MS (m/z) 474 (MH+). mp 43.3° C.

Example 301

(5R, 7S)-5-[4-(Trifluoromethoxy)benzyl]-3-(3,5-dichlorophenyl)-7-(N-acety-N-methylamino)-1,3-diazabicyclo[3.3.0]octane-2,4-dione LDA (0.34 M in THF; 0.045 g) was added to a solution of the compound from Example 64 (0.18 g) in THF at −80° C. and the mixture was stirred for 20 minutes at that temperature. MeI (0.65 g) was added and the reaction mixture was stirred for 10 minutes. The mixture was warmed to room temperature and stirred for additional 20 minutes. It was quenched with aqueous NH4Cl solution and the mixture was evaporated. The residue was purified via HPLC (CH3CN/0.1 M AcOH) to yield 0.012 g of the titled compound. MS (m/z) 531 (MH+) and 553 (MNa+). mp 74.7° C.

Example 302

(5R, 7S)-5-[4-(Trifluoromethoxy)benzyl]-3-(3,5-dichlorophenyl)-7-[[4-(dimethylamino)butyryl]amino]-1,3-diazabicyclo[3.3.0]octane-2,4-dione This compound was prepared similar to Example 67. MS (m/z) 587 (MH+). mp 57.9° C.

The following compounds were prepared in a manner similar to one of the above Examples.

TABLE 24

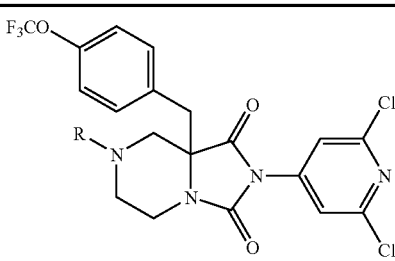

| Example | R | Method similar to Example | MS m/z (MH+) | mp (° C.) |
|---|---|---|---|---|
| 303 | t-BOC | 161 | 575 | 185 |
| 304 | H | 162 | 511 | 155.9 |

TABLE 24-continued

![structure with R-N piperazine, trifluoromethoxybenzyl, dichloropyridyl imidazolidinedione]

| Example | R | Method similar to Example | MS m/z (MH+) | mp (° C.) |
|---|---|---|---|---|
| 305 | ![Me-N piperazine-N-C(O)CH2CH2C(O)CH3] | 67 | 657 | 71 |
| 306 | ![H2N-C(O)-CH2CH2-C(O)-CH3] | 67 | 574 | 99.7 |
| 307 | ![Et-C(O)-] | 64 | 531 | 166.9 |
| 308 | H2NCH2CO— | 244 | 582 | 209.4 |
| 309 | H2N(CH2)2CO— | 244 | 582 | 196.7 |

The following compounds were prepared in a manner similar to Examples 189 and 190.

TABLE 25

![structure with R-benzyl, pyrrolidine fused imidazolidinedione, 3,5-dichlorophenyl]

| Example | R | MS m/z (MH+) | mp (° C.) |
|---|---|---|---|
| 310 | SOCF3 | 491 | 63.5 |
| 311 | SO2CF3 | 507 | 72.5 |

Example 312

(5R, 7R)-5-[4-(Trifluoromethoxy)benzyl]-3-(3,5-dichlorophenyl)-7-carbamoyl-1,3-diazabicyclo[3.3.0]octane-2,4-dione

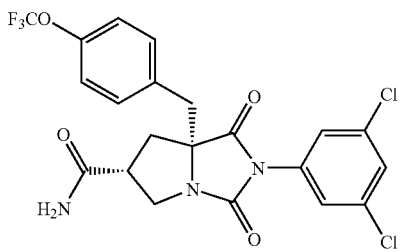

The compound from Example 257, step-7 (diacid compound 8, 0.153 g) was treated with thionyl chloride (2 mL) and heated to reflux. After 1 hour, the reaction mixture was concentrated and evaporated with toluene. The residue was dissolved in THF (3 mL) and the mixture was added to NH$_4$OH (0.5 mL) in THF (5 mL) chilled with an ice bath. After 15 minutes, the mixture was added to 3N HCl (10 mL). The mixture was extracted with EtOAc. The extract was washed with brine, dried (Na$_2$SO$_4$), filtered and concentrated. Purification by HPLC afforded the titled compound (0.108 g): MS (m/z) 502 (MH+); mp 122.7° C.

The following compounds were prepared in a manner similar to the Example 257 replacing BOP reagent with SOCl$_2$ in step-8 as described in Example 310.

TABLE 26

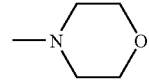

| Example | Diastereomer | R | MS m/z (MH$^+$) | mp (° C.) |
|---|---|---|---|---|
| 313 | 5R, 7R | —NMe$_2$ | 530 | 106.1 |
| 314 | 5R, 7R | —NHMe | 516 | 212.6 |
| 315 | 5R, 7R | —N(morpholine) | 572 | |
| 316 | 5R, 7R | —HN—N(morpholine) | 587 | 174.8 |
| 317 | 5R, 7S | —NH$_2$ | 502 | 140.3 |
| 318 | 5R, 7S | —N(morpholine) | 572 | 129.1 |
| 319 | 5R, 7S | —NHMe | 516 | 122.7 |

REFERENCE EXAMPLES

Preparation of the Substituted benzylbromide Intermediate: Prototype Example

Synthesis of 5-bromomethyl-2,2-difluorobenzodioxole

BH$_3$-THF (1M, 10 mL) was added to a solution of 2,2-difluorobenzodioxole-5-carboxylic acid (0.52 g) in THF (10 mL) and the resulting mixture was stirred at room temperature for 14 hours. The reaction mixture was quenched with 2 N HCl and extracted with EtOAc. The EtOAc solution was washed with brine, dried (Na$_2$SO$_4$) and concentrated to yield the alcohol (0.42 g) that was used as is for the next step.

The above compound was dissolved in dry CH$_2$Cl$_2$ (10 mL) and Ph$_3$P (1.86 g) was added with stirring. After about 15 minutes a solution of CBr$_4$ (4.06 g) in CH$_2$Cl$_2$ was added dropwise with stirring. After 20 hours the reaction mixture was concentrated and the residue was purified via chromatography (silica gel; hexanes-20% EtOAc/hexanes) to yield the desired bromide (0.48 g).

All benzyl bromides were prepared in an analogous manner starting from the requisite acid.

Cell Adhesion Protocol

Cell Adhesion—The recombinant protein ICAM-1·Fc was constructed from the 5 extracellular domains of human ICAM-1 and fusion with the constant region of human IgG. ICAM-1Fc was purified by Protein A affinity chromatography and stored in aliquots at −20° C. Immobilized ICAM-1·Fc was prepared by dilution of the protein in PBS pH 7.5, transfer of 100 μl/well to Falcon Probind III plates and overnight incubation at 4° C. Wells coated with BSA served as a measure of non specific background adhesion. Washed plates were blocked with a solution of 0.25% ovalbumin in PBS for 1 h at 37° C. HBSS washed Jurkat cells were suspended to a final concentration of 2.5×10$^6$/ml in TBSg adhesion buffer (24 mM Tris pH 7.4, 0.14 M NaCl, 2.7 mM KCl, 2 mM glucose, 0.1% HSA). A 100 μl volume of cells was added to the blocked and washed ICAM-1·Fc coated plates that contained 100 μl of plate buffer (TBSg, 10 mM MgCl$_2$, 2% DMSO). Adhesion was for 1 h at 37° C. Non adherent cells were removed using the EL404 plate washer (BioTek Instruments; Highland Park, Vt.). The number of adherent cells was quantified by measuring enzymatic activity of endogenous N-acetyl-hexosaminidase using the enzyme substrate p-nitrophenol-N-acetyl-b-D-glucoseaminide, pNAG. The amount of liberated p-nitrophenol was measured by reading the optical density at 405 nm using a vertical pathway spectrophotometer to quantify cell attachment (VMAX Kinetic Microplate Reader, Molecular Devices, Menlo Park, Calif.). For competition studies the compounds from 100% DMSO stock solutions were diluted in plate buffer at 2-fold the required testing concentration prior to transfer to the ICAM-1·Fc coated plate and serial dilution.

The compound of the present invention has an IC$_{50}$ from low nM to μM in the Jurkat/ICAM-1 adhesion assay.

The invention claimed is:

1. A compound of the formula (I):

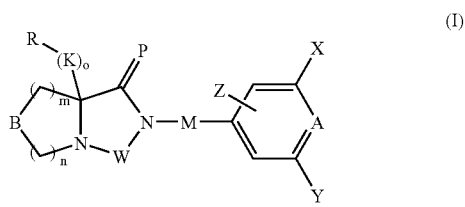

or a pharmaceutically acceptable salt thereof; wherein

A is =C(Z$^1$)—, or =N—;
B is —N(R$^3$)—, —N(COR$^{41}$)—, —N(CSR$^{41}$)—, or —N(SO$_2$R$^5$)—;
K is —CH$_2$—, —CH(OH)—, —C(=O)—, or —CF$_2$—;
M is a single bond, —(CH$_2$)$_p$—, —C(=O)— or —NH—;
W is the following group:

X and Y are independently
1) H,
2) halogen,
3) $NO_2$,
4) CN,
5) $C_{1-6}$ alkylthio,
6) $NR^3R^6$,
7) $C_{1-6}$ alkyl optionally substituted with halogen,
8) $C_{1-6}$ alkoxy,
9) $COR^{42}$,
10) aryl which may be substituted, or
11) heteroaryl which may be substituted;

Z and $Z^1$ are independently
1) H,
2) OH,
3) halogen,
4) $NO_2$,
5) $CF_3$,
6) $NR^3R^6$,
7) $NHCOR^{41}$,
8) $C_{1-6}$ alkoxy optionally substituted with:
  a) carboxyl,
  b) $C_{1-6}$ alkoxycarbonyl, or
  c) phenyl, or
9) $COR^{42}$;

P and Q are independently O;

R is aryl or heteroaryl, and said aryl and heteroaryl may be substituted with a group selected from:
1) halogen,
2) OH,
3) CN,
4) $C_{1-6}$ alkyl optionally substituted with a group selected from:
  a) halogen
  b) $OR^6$,
  c) $COR^{41}$,
  d) aryl which may be substituted, or
  e) $NR^3R^6$,
5) $C_{1-6}$ alkoxy optionally substituted with a group selected from:
  a) halogen
  b) $NR^3R^6$,
  c) aryl which may be substituted,
  d) heteroaryl which may be substituted, and
  e) non-aromatic heterocyclic group,
6) $NO_2$,
7) $NR^3R^6$,
8) $NHCOR^{41}$,
9) $NHSO_2R^5$,
10) $COR^{42}$,
11) $C(=NH)NH_2$,
12) CONHOH,
13) $C_{1-6}$ alkylthio which may be substituted with halogen,
14) $C_{1-6}$ alkylsulfinyl which may be substituted with halogen,
15) $C_{1-6}$ alkylsulfonyl which may be substituted with halogen,
16) $C_{1-3}$ alkylenedioxy optionally substituted with:
  a) $C_{1-6}$ alkyl,
  b) halogen,
  c) aryl which may be substituted, or
  d) heteroaryl which may be substituted,
17) —C(=O)-(natural α-amino acid residue) wherein said natural α-amino acid residue may be esterified with $C_{1-6}$ alkyl group,
18) aryl which may be substituted, and
19) heteroaryl which may be substituted;

$R^1$ and $R^2$ are independently
1) H,
2) halogen,
3) $OR^3$,
4) $OCOR^5$,
5) $SO_2R^5$
6) $NR^3R^6$,
7) $NR^6COR^{41}$,
8) $NR^6CSR^{41}$,
9) $NR^6SO_2R^5$,
10) $OCONR^3R^3$,
11) $N_3$,
12) $C_{1-6}$ alkyl which may be substituted,
13) CN,
14) $COR^{42}$,
15) aryl which may be substituted, or
16) heteroaryl which may be substituted;

or $R^1$ and $R^2$ combine with each other at the terminal thereof to form:
1) oxo,
2) methylene substituted with carboxyl, $C_{2-7}$ alkoxycarbonyl, or $CONR^aR^b$, or
3) $C_{2-3}$ alkylenedioxy;

$R^a$ and $R^b$ combine with each other at the terminals thereof to form a 3-7 membered ring together with the nitrogen atom to which they are attached, where said 3-7 membered ring may include additional heteroatoms selected from the group consisting of oxygen, nitrogen and sulfur and may be substituted with $C_{1-6}$ alkyl, oxo, hydroxy, $C_{1-6}$ alkoxy or $NR^6R^6$;

$R^3$ is
1) H,
2) $C_{1-6}$ alkyl which may be substituted,
3) $C_{3-6}$ cycloalkyl,
4) aryl which may be substituted,
5) heteroaryl which may be substituted, or
6) non-aromatic heterocyclic group;

$R^{41}$ is
1) $C_{1-6}$ alkyl which may be substituted,
2) $C_{1-6}$ alkoxy which may be substituted,
3) aryl which may be substituted,
4) heteroaryl which may be substituted,
5) non-aromatic heterocyclic group which may be substituted,
6) $C_{3-6}$ cycloalkyl, or
7) $NR^3R^6$;

$R^{42}$ is
1) H,
2) OH,
3) $C_{1-6}$ alkyl which may be substituted,
4) $C_{1-6}$ alkoxy which may be substituted,
5) aryl which may be substituted,
6) $NR^3R^6$, or
7) non-aromatic heterocyclic group which may be substituted;

$R^5$ is
1) $C_{1-6}$ alkyl which may be substituted, or
2) aryl which may be substituted;

$R^6$ is
1) H, or
2) $C_{1-6}$ alkyl which may be substituted;

m is 1;
n is 2;
o is 1 or 2; and
p is 1 or 2.

2. The compound according to claim 1, wherein
X and Y are independently selected from:
  1) halogen,
  2) $NO_2$,
  3) $C_{1-6}$ alkyl optionally substituted with halogen,
  4) $C_{1-6}$ alkoxy group,
  5) $C_{1-7}$ alkanoyl group,
  6) CN,
  7) carboxyl,
  8) $C_{1-6}$ alkylthio,
  9) $NR^3R^6$,
  10) phenyl optionally substituted with:
    a) $C_{1-6}$ alkyl optionally substituted with halogen,
    b) $C_{1-6}$ alkoxy optionally substituted with halogen, or
    c) CN,
  11) isoxazolyl optionally substituted with $C_{1-6}$ alkyl,
  12) pyrrolyl optionally substituted with $C_{1-6}$ alkoxycarbonyl or formyl,
  13) pyridyl,
R is phenyl, naphthyl, pyridyl, benzofuryl or thiazolyl, wherein said phenyl, naphthyl, pyridyl, benzofuryl and thiazolyl may be substituted with a group selected from:
  1) halogen,
  2) OH,
  3) CN,
  4) $C_{1-6}$ alkyl optionally substituted with a group selected from:
    a) halogen,
    b) $OR^6$, or
    c) $COR^{41}$,
  5) $C_{1-6}$ alkoxy optionally substituted with a group selected from:
    a) halogen,
    b) $NR^3R^6$,
    c) pyridyl, or
    d) piperidinyl,
  6) $NO_2$,
  7) $NR^3R^6$,
  8) $NHCOR^{41}$,
  9) $NHSO_2R^5$,
  10) $COR^{42}$,
  11) $C(=NH)NH_2$,
  12) CONHOH,
  13) $C_{1-6}$ alkylthio which may be substituted with halogen,
  14) $C_{1-6}$ alkylsulfinyl which may be substituted with halogen,
  15) $C_{1-6}$ alkylsulfonyl which may be substituted with halogen,
  16) $C_{1-3}$ alkylenedioxy optionally substituted with:
    a) $C_{1-6}$ alkyl, or
    b) halogen,
  17) —C(=O)-(natural α-amino acid residue), wherein said natural α-amino acid is selected from aspartic acid, alanine, phenylalanine, and asparagine and said natural α-amino acid residue may be esterified with $C_{1-6}$ alkyl group,
  18) phenyl optionally substituted with:
    a) $C_{1-6}$ alkoxy,
    b) $C_{1-6}$ alkyl optionally substituted with $OR^6$, $N(C_{1-6}$ alkyl$)_2$ or $COR^{42}$,
    c) CN,
    d) $COR^{42}$,
    e) $C_{2-7}$ alkenyl optionally substituted with $COOR^5$,
    f) $NR^6R^6$,
    g) $NO_2$,
    h) $NHCOR^{41}$,
    i) $NHSO_2R^5$,
    j) $N(SO_2R^5)_2$,
    k) $NHCONHR^5$,
    l) $N(CONHR^5)_2$,
    m) $NHCSNHR^5$, or
    n) pyrrolidinyl which may be substituted with $C_{1-6}$ alkyl,
  19) furyl optionally substituted with CHO,
  20) thienyl optionally substituted with CHO,
  21) pyrrolyl optionally substituted with CHO and $C_{1-6}$ alkoxycarbonyl,
  21) dihydroxazolyl optionally substituted with $C_{1-6}$ alkyl,
  22) isoxazolyl optionally substituted with $C_{1-6}$ alkyl,
  23) benzothienyl,
  24) pyridyl,
  25) tetrazolyl, and
  26) thiazolyl which may be substituted with $C_{1-6}$ alkyl;
$R^1$ and $R^2$ are independently selected from:
  1) H,
  2) halogen,
  3) $OR^3$,
  4) $OCOR^5$,
  5) $NR^3R^6$,
  6) $NR^6COR^{41}$,
  7) $NHCSR^{41}$,
  8) $NHSO_2R^5$,
  9) $N_3$,
  10) $COR^{42}$, or
  11) phenyl;
or $R^1$ and $R^2$ combine with each other at the terminal thereof to form oxo;
$R^3$ is
  1) hydrogen;
  2) $C_{1-6}$ alkyl optionally substituted with:
    a) OH,
    b) phenyl optionally substituted with halogen or $C_{1-6}$ alkoxy,
    c) carboxyl,
    d) carbamoyl,
    e) $NR^6R^6$,
    f) $C_{1-6}$ alkoxycarbonyl,
    g) morpholinyl,
    h) pyridyl,
    i) thienyl, or
    j) pyrrolidinyl optionally substituted with oxo,
  3) $C_{3-6}$ cycloalkyl,
  4) phenyl optionally substituted with halogen,
  5) pyridyl optionally substituted with $C_{1-6}$ alkyl, or
  6) morpholinyl;
$R^{41}$ is
  1) $C_{1-6}$ alkyl optionally substituted with a group selected from:
    a) $NR^6R^6$,
    b) carboxyl,
    c) —$CONR^cR^d$ where $R^c$ and $R^d$ are independently selected from hydrogen and $C_{1-6}$ alkyl, or $R^c$ and $R^d$ combine with each other at the terminals thereof to form a 3-7 membered ring together with the nitrogen atom to which they are attached, and said 3-7 membered ring may include additional 1-3 heteroatoms selected from the group consisting of oxygen, nitrogen and sulfur and may be substituted with $C_{1-6}$ alkyl, oxo, hydroxy, $C_{1-6}$ alkoxy or $NR^6R^6$, d) $C_{1-6}$ alkoxycarbonylamino,
e) $C_{1-6}$ alkylsulfonylamino,
f) $C_{2-7}$ alkanoylamino, and
g) pyridyl;
2) $C_{1-6}$ alkoxy optionally substituted with $NR^6R^6$ or phenyl,
3) $NR^3R^6$,
4) phenyl optionally substituted with:
  a) carboxyl,
  b) $C_{1-6}$ alkoxycarbonyl, or
  c) $NR^6R^6$,
5) $C_{3-6}$ cycloalkyl,
6) isoxazolyl optionally substituted with $C_{1-6}$ alkyl,
7) pyridyl,
8) thienyl,
9) furyl, or
10) $NR^aR^b$;
$R^{42}$ is
1) H
2) OH;
3) $C_{1-6}$ alkyl optionally substituted with $NR^6R^6$ or phenyl,
4) $C_{1-6}$ alkoxy optionally substituted with $NR^6R^6$,
5) $NR^3R^6$,
6) $NR^aR^b$, or
7) pyridyl which may be substituted with $C_{1-6}$ alkyl;
$R^5$ is
1) $C_{1-6}$ alkyl optionally substituted with $COR^{42}$, or
2) aryl;
$R^6$ is
1) hydrogen, or
2) $C_{1-6}$ alkyl optionally substituted with $-N(C_{1-6}\text{alkyl})_2$.

3. The compound according to claim 2, wherein the chemical structure is the following:

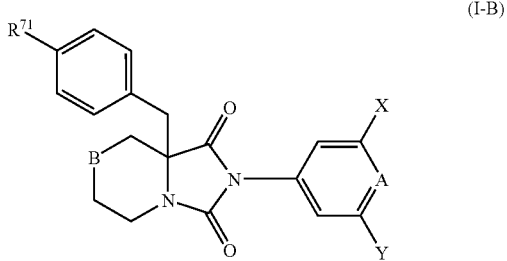

(I-B)

wherein A is =CH— or =N—;
B is $-N(R^3)-$, $-N(COR^{41})-$, $-N(CSR^{41})-$ or $-N(SO_2R^5)-$;
X and Y are independently H, halogen, $NO_2$, or $C_{1-6}$ alkyl;
$R^{71}$ a group selected from:
1) H,
2) halogen,
3) CN,
4) $C_{1-6}$ alkyl optionally substituted with halogen,
5) $C_{1-6}$ alkoxy optionally substituted with halogen,
6) $COR^{42}$,
7) $C_{1-6}$ alkylthio,
8) phenyl,
9) thienyl,
10) furyl,
11) pyrrolyl,
12) isoxazolyl substituted with $C_{1-6}$ alkyl, wherein said phenyl may be substituted with a group selected from a) $C_{2-7}$ alkenyl substituted with $COOR^5$, b) $COR^{42}$, c) $C_{1-6}$ alkyl optionally substituted with $OR^6$, d) $C_{1-6}$ alkoxy, and e) CN, and said thienyl, furyl and pyrrolyl may be substituted with CHO.

4. The compound according to claim 3, wherein
B is $-N(COR^{41})-$;
X and Y are independently halogen;
$R^{41}$ is
1) $C_{1-6}$ alkyl optionally substituted with a group selected from:
  a) $NR^6R^6$,
  b) carbamoyl, and
  c) piperazinylcarbonyl optionally substituted with $C_{1-6}$ alkyl;
2) $C_{1-6}$ alkoxy, or
3) $NR^3R^6$;
$R^{71}$ is
1) halogen, or
2) $C_{1-6}$ alkoxy optionally substituted with halogen.

5. A pharmaceutical composition which comprises a therapeutically effective amount of the compound as set forth in claim 1 in admixture with a therapeutically acceptable carrier or diluent.

6. A method for treatment of $\alpha_L\beta_2$ adhesion mediated condition selected from rheumatoid arthritis, asthma, allergy conditions, adult respiratory distress syndrome, AIDS, thrombosis or harmful platelet aggregation, reocclusion following thrombolysis, allograft rejection, reperfusion injury, skin inflammatory diseases, osteoporosis, osteoarthritis, atherosclerosis, Type I diabetes, multiple sclerosis, systemic lupus erythematosus (SLE), ophthalmic inflammatory conditions, inflammatory bowel diseases, regional enteritis, Sjogren's Syndrome, pancreatitis, delayed graft function, intimal hyperplasia; myocardial reinfarction or restenosis after surgery, rejection after transplantation, and host vs. graft or graft vs. host diseases in a mammal comprising administering a therapeutically effective amount of the compound as set forth in claim 1.

7. The method according to claim 6, wherein said $\alpha_L\beta_2$ adhesion mediated condition is selected from psoriasis, rheumatoid arthritis, inflammatory bowel diseases, systemic lupus erythematosus, atopic dermatitis, Sjogren's Syndrome, rejection after transplantation, and graft vs. host disease.

8. The method according to claim 6, wherein
said skin inflammatory disease is contact dermatitis or atopic dermatitis;
said atherosclerosis is graft atherosclerosis after transplantation;
said myocardial reinfarction or restenosis after surgery is myocardial reinfarction or restenosis after percutaneous transluminal coronary angioplasty;
said inflammatory bowel disease is Crohn's disease or ulcerative colitis; and
said rejection after transplantation is chronic rejection after transplantation or acute rejection after transplantation.

* * * * *